(12) United States Patent
Rahbar et al.

(10) Patent No.: US 10,029,991 B2
(45) Date of Patent: Jul. 24, 2018

(54) MODULATORS OF DEVELOPMENT OF ADIPOCYTE AND CANCER CELLS

(71) Applicant: CITY OF HOPE, Duarte, CA (US)

(72) Inventors: Samuel Rahbar, Beverly Hills, CA (US); James L. Figarola, West Covina, CA (US); Christopher Lincoln, La Canada, CA (US); David Horne, Altadena, CA (US); Rachael Mooney, Duarte, CA (US); Monika Polewski, Duarte, CA (US); George Somlo, Seal Beach, CA (US); Lixin Yang, Arcadia, CA (US); Sanjay Awasthi, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 13/953,013

(22) Filed: Jul. 29, 2013

(65) Prior Publication Data
US 2014/0162996 A1 Jun. 12, 2014

Related U.S. Application Data

(63) Continuation of application No. PCT/US2012/023034, filed on Jan. 27, 2012.
(Continued)

(51) Int. Cl.
*C07C 69/12* (2006.01)
*A61K 31/192* (2006.01)
(Continued)

(52) U.S. Cl.
CPC ............ *C07D 239/42* (2013.01); *A61K 31/17* (2013.01); *A61K 31/192* (2013.01);
(Continued)

(58) Field of Classification Search
CPC .... A61K 31/192; A61K 31/197; A61K 31/44; C07C 69/12
See application file for complete search history.

(56) References Cited

U.S. PATENT DOCUMENTS 4,233,450 A 11/1980 Scholz
5,773,459 A 6/1998 Tang et al.
(Continued)

FOREIGN PATENT DOCUMENTS

CA 2 436 886 * 6/2002
WO WO2004/031122 * 4/2004
(Continued)

OTHER PUBLICATIONS

Physical Activity and Obesity, edited by Claude Bouchard and Peter T. Katzmarkzyk, copyright 2000, ISBN-10:0-7360-7635-2.*
(Continued)

*Primary Examiner* — San-Ming Hui
(74) *Attorney, Agent, or Firm* — Perkins Coie LLP; Yingli Wang

(57) ABSTRACT

One aspect of the disclosure relates to derivatives of aryl and heterocyclic ureido aryl and heterocyclic carboxamido isobutyric acids, dichlorophenyl urea, curcumin, and 1,3-diazetidine-2,4-dione, and pharmaceutical compositions thereof. The derivatives disclosed herein can modulate development of adipocytes and various cancer cells, including resistant cancer cells and cancer stem cells. Another aspect of the disclosure relates to the use of the derivatives and pharmaceutical compositions disclosed herein in treatment of obesity and various cancers.

6 Claims, 81 Drawing Sheets

Related U.S. Application Data

(60) Provisional application No. 61/436,958, filed on Jan. 27, 2011.

(51) Int. Cl.

| | | |
|---|---|---|
| *A61K 31/197* | (2006.01) | |
| *C07D 239/42* | (2006.01) | |
| *C07C 275/30* | (2006.01) | |
| *C07C 275/34* | (2006.01) | |
| *C07C 275/42* | (2006.01) | |
| *C07D 229/00* | (2006.01) | |
| *A61K 31/17* | (2006.01) | |
| *A61K 31/222* | (2006.01) | |
| *A61K 31/397* | (2006.01) | |
| *A61K 31/44* | (2006.01) | |
| *A61K 31/505* | (2006.01) | |
| *A61K 45/06* | (2006.01) | |
| *C07D 213/75* | (2006.01) | |

(52) U.S. Cl.
CPC .......... *A61K 31/197* (2013.01); *A61K 31/222* (2013.01); *A61K 31/397* (2013.01); *A61K 31/44* (2013.01); *A61K 31/505* (2013.01); *A61K 45/06* (2013.01); *C07C 69/12* (2013.01); *C07C 275/30* (2013.01); *C07C 275/34* (2013.01); *C07C 275/42* (2013.01); *C07D 213/75* (2013.01); *C07D 229/00* (2013.01); *C07C 2601/14* (2017.05)

(56) References Cited

U.S. PATENT DOCUMENTS

| | | |
|---|---|---|
| 6,337,350 B1 | 1/2002 | Rahbar et al. |
| 6,589,944 B1 * | 7/2003 | Rahbar .................. 514/166 |
| 6,589,994 B1 | 7/2003 | Artman et al. |
| 6,605,642 B2 | 8/2003 | Rahbar et al. |
| 6,693,106 B2 | 2/2004 | Rahbar et al. |
| 6,787,566 B2 | 9/2004 | Rahbar et al. |
| 7,030,133 B2 | 4/2006 | Rahbar et al. |
| 7,320,988 B2 | 1/2008 | Rahbar et al. |
| 7,652,037 B2 | 1/2010 | Rahbar et al. |
| 2009/0202529 A1 | 8/2009 | Threadgill et al. |
| 2010/0196389 A1 * | 8/2010 | Evans-Freke ............ 424/145.1 |

FOREIGN PATENT DOCUMENTS

| | | | | |
|---|---|---|---|---|
| WO | WO 2007/055966 | * | 5/2007 | ............ A61K 48/00 |
| WO | 2008/101030 A1 | | 8/2008 | |
| WO | WO 2008101030 A1 | * | 8/2008 | ............ C07H 21/04 |
| WO | WO 2010/138820 | * | 12/2010 | ......... A61K 31/5377 |

OTHER PUBLICATIONS

Guarnieri, et al., J. Ren. Nutr., Jan. 19, 2009, (1):20-4, Insulin Resistance in Chronic Uremia.*
Kantor, P. et al, Circ. Res. 2000;86:580-588.*
Kahn, et al., Obesity and Insulin Resistance, The Journal of Clinical INvestigation, Aug. 2000, vol. 4, p. 473.*
English translation of the claims and description of WO2004/031122.*
Lopez-Bergami, P., et al., "Re-Wired ERK-JNK Signaling Pathways in Melanoma," Cancer Cell 11(5):447-460 (2007).
Lowe, S. W., et al., "Apoptosis in Cancer," Carcinogenesis 21(3):485-495 (2000).
Lyon, R. P., et al., "Novel Class of Bivalent Glutathione S-Transferase Inhibitors," Biochem. 42:10418-10428 (2003).
Mannervik, B., et al., "Expression of Class Pi Glutathione Transferase in Human Malignant Melanoma Cells," Carcinogenesis 8(12):1929-1932 (1987).
Meikle, S. R., et al., "Pharmacokinetic Assessment of Novel Anti-Cancer Drugs Using Spectral Analysis and Positron Emission Tomography: A Feasibility Study," Cancer Chemother. Pharmacol. 42:183-193 (1998).
Nowak, D., et al., "Differentiation Therapy of Leukemia: 3 Decades of Development," Blood 113:3655-3665 (2009).
Pardridge, W. M., "The Blood-Brain Barrier: Bottleneck in Brain Drug Development," J. Amer. Soc. Exp. NeuroTher. 2:3-14 (2005).
Petrie, K., et al., "Differentiation Therapy of Acute Myeloid Leukemia: Past, Present and Future," Curr. Top. Hematol. 16:84-91 (2009).
Pilch, P. F., et al., "Pharmacological Targeting of Adipocytes/Fat Metabolism for Treatment of Obesity and Diabetes," Mol. Pharmacol. 70(3):779-785 (2006).
Prat, A., et al., "Deconstructing the Molecular Portraits of Breast Cancer," Mol. Oncol. 5:5-23 (2011).
Proctor, R. A., et al., "Two Diarylurea Electron Transport Inhibitors Reduce *Staphylococcus aureus* Hemolytic Activity and Protect Cultured Endothelial Cells from Lysis," Antimicrobial Agents and Chemotherapy 46(8):2333-2336 (2002).
Pubchem Compound, CID 10994120 Compound Summary, http://pubchem.ncbi.nlm.nih.gov/summary/summary.cgi?cid=10994120, accessed Jul. 24, 2012.
Quartu, M., et al., "Polysialylated-Neural Cell Adhesion Molecule (PSA-NCAM) in the Human Trigeminal Ganglion and Brainstem at Prenatal and Adult Ages," BMC Neurosci. 9:108 (2008) (doi:10.1186/1471-2202-9-108).
Rahbar, S., et al., "Novel Inhibitors of Advanced Glycation Endproducts," Arch. Biochem. Biophys. 419:63-79 (2003).
Rathmell, J. C., et al., "Biochemistry. A Glucose-to-Gene Link," Science 324(5930):1021-1022 (2009).
Ricci, A., et al., "Effect of Cl-Substitution on Rooting- or Cytokinin-Like Activity of Diphenylurea Derivatives," J. Plant Growth Regul. 23:261-268 (2005).
Ricci, A., et al., "Urea Derivatives on the Move: Cytokinin-Like Activity and Adventitious Rooting Enhancement Depend on Chemical Structure," Plant Biol. 11:262-272 (2009).
Riester, D., et al., "Histone Deacetylase Inhibitors—Turning Epigenic Mechanisms of Gene Regulation Into Tools of Therapeutic Intervention in Malignant and Other Diseases," Appl. Microbiol. Biotechnol. 75:499-534 (2007).
Roy, R., et al., "Differentiation Therapy: Targeting Breast Cancer Stem Cells to Reduce Resistance to Radiotherapy and Chemotherapy," Breast Cancer Res. 12(Suppl. 1):O5 (2010) (doi.10.1186/bcr2496).
Sell, S., "Stem Cell Origin of Cancer and Differentiation Therapy," Crit. Rev. Oncol. Hematol. 51:1-28 (2004).
Shea, T. C., et al., "Identification of an Anionic Form of Glutathione Transferase Present in Many Human Tumors and Human Tumor Cell Lines," Cancer Res. 48:527-533 (1998).
Storz, P., "Reactive Oxygen Species in Tumor Progression," Frontiers in Bioscience 10:1881-1896 (2005).
Stupp, R., et al., "Radiotherapy Plus Concomitant and Adjuvant Temozolomide for Glioblastoma," N. Engl. J. Med. 352:987-996 (2005).
Tew, K. D., et al., "Glutathione-Associated Enzymes in the Human Cell Lines of the National Cancer Institute Drug Screening Program," Mol. Pharmacol. 50:149-159 (1996).
Thangasamy, T., et al., "Quercetin Selectively Inhibits Bioreduction and Enhances Apoptosis in Melanoma Cells That Overexpress Tyrosinase," Nutrition and Cancer 59(2):258-268 (2007).
United States Patent and Trademark Office, International Search Report and Written Opinion dated Jul. 17, 2012 for PCT/US2012/023034.
Van Lenten, L., et al., "Chemistry and Metabolism of Macromolecules: Studies on the Chemical and Enzymatic Modification of Glycoproteins: A General Method for the Tritiation of Sialic Acid-Containing Glycoproteins," J. Biol. Chem. 246:1889-1894 (1971).
Wald, D. N., et al., "Identification of 6-Benzylthioinosine as a Myeloid Leukemia Differentiation-Inducing Compound," Cancer Res. 68:4369-4376 (2008).
Wang, W., et al., "AMP-Activated Protein Kinase and Cancer," Acta Physiol. 196:55-63 (2009).

(56) References Cited

OTHER PUBLICATIONS

Waxman, D. J., "Glutathione S-Transferases: Role in Alkylating Agent Resistance and Possible Target for Modulation Chemotherapy—A Review," Cancer Res. 50:6449-6454 (1990).
Wellen, K, E., et al., "ATP-Citrate Lyase Links Cellular Metabolism to Histone Acetylation," Science 324 (5930):1076-1080 (2009).
Yu, L.F., et al., "AMPK Activators as Novel Therapeutics for Type 2 Diabetes," Curr. Top. Med. Chem. 10:397-410 (2010).
Yun, H., et al., "AMP-Activated Protein Kinase Modulators: A Patent Review (2006-2010)," Expert Opin. Ther. Patents 21(7):983-1005 (2011).
Zhuang, Y., et al., "Cell Cycle Arrest in Metformin Treated Breast Cancer Cells Involves Activation of AMPK, Downregulation of Cyclin D1, and Requires p27Kip1 or p21Cip1," J. Mol. Signaling 3:18 (2008) (doi:10.1186/1750-2187-3-18).
Adler, V., et al., "Regulation of JNK Signaling by GSTp," EMBO Journal 18(5):1321-1334 (1999).
Al-Hajj, M., et al., "Prospective Identification of Tumorigenic Breast Cancer Cells," PNAS 100(7):3983-3988 (2003).
Ali-Osman, F., et al., "Prognostic Significance of Glutathione S-Transferase Pi Expression and Subcellular Localization in Human Gliomas," Clin. Cancer Res. 3:2253-2261 (1997).
Auld, C. A., et al., "Skp2-Mediated p27(Kip1) Degradation During S/G2 Phase Progression of Adipocyte Hyperplasia," J. Cell. Physiol. 211:101-111 (2007).
Awasthi, Y.C., et al., "Enzymatic Conjugation of Erythrocyte Glutathione with 1-Chloro-2,4-Dinitrobenzene: The Fate of Glutathione Conjugate in Erythrocytes and the Effect of Glutathione Depletion on Hemoglobin," Blood 58:733-738 (1981).
Badva, S., et al., "Basal-Like and Triple-Negative Breast Cancers: A Critical Review with an Emphasis on the Implications for Pathologists and Oncologists," Modern Pathology 24:157-167 (2011).
Benny, O., et al., "Novel Technologies for Antiangiogenic Drug Delivery in the Brain," Cell Adhesion and Migration 3 (2):224-229 (2009).
Berwick, M., et al., "The Current Epidemiology of Cutaneous Malignant Melanoma," Frontiers in Bioscience 11:1244-1254 (2006).
Bosch, A., et al., "Triple-Negative Breast Cancer: Molecular Features, Pathogenesis, Treatment and Current Lines of Research," Cancer Treat. Rev. 36:206-215(2010).
Boyle, J. G., et al., "AMP-Activated Protein Kinase is Activated in Adipose Tissue of Individuals with Type 2 Diabetes Treated with Metformin: A Randomised Glycaemia-Controlled Crossover Study," Diabetologia 54:1799-1809 (2011).
Bray, G. A., et al., "Epidemiology, Trends, and Morbidities of Obesity and the Metabolic Syndrome," Endocrine 29 (1):109-117 (2006).
Bray, G. A., et al., "Medicinal Strategies in the Treatment of Obesity," Nature 404:672-677 (2000).
Bruserud, O., et al., "Induction of Differentiation and Apoptosis—A Possible Strategy in the Treatment of Adult Acute Myelogenous Leukemia," The Oncologist 5:454-462 (2000).
Carra, A., et al., "Diphenylurea Derivatives Induce Somatic Embryogenesis in Citrus," Plant Cell Tiss. Organ Cult. 87:41-48 (2006).
Cho, R. W., et al., "Isolation and Molecular Characterization of Cancer Stem Cells in MMTV-Wnt-1 Murine Breast Tumors," Stem Cells 26:364-371 (2008).
Chou, T.C., "Theoretical Basis, Experimental Design, and Computerized Simulation of Synergism and Antagonism in Drug Combination Studies," Pharmacol. Rev. 58:621-681 (2006).
Cool, B., et al., "Identification and Characterization of a Small Molecule AMPK Activator that Treats Key Components of Type 2 Diabetes and the Metabolic Syndrome," Cell Metabolism 3:403-416 (2006).
Davies, G.F., et al., "Troglitazone Inhibits Histone Deacetylase Activity in Breast Cancer Cells," Cancer Letters 288:236-250 (2010).
De Ferranti, S., et al., "The Perfect Storm: Obesity, Adipocyte Dysfunction, and Metabolic Consequences," Clinical Chemistry 54(6):945-955 (2008).
DeAngelis, L. M., "Brain Tumors," N. Engl. J. Med. 344(2):114-123 (2001).
Doyle, B. T. et al. "Differentiation-Induced HL-60 Cell Apoptosis: A Mechanism Independent of Mitochondrial Disruption?" Apoptosis 9:345-352 (2004).
Fernandes, K. M., et al., "Helenalin-Mediated Post-Transcriptional Regulation of p21(Cip1) Inhibits 3T3-L1 Preadipocyte Proliferation," J. Cell. Biochem. 105(3):913-921 (2008).
Fischer, H., et al., "Blood-Brain Barrier Permeation: Molecular Parameters Governing Passive Diffusion," J. Membrane Biol. 165:201-211 (1998).
Fogarty, S., et al., "Development of Protein Kinase Activators: AMPK as a Target in Metabolic Disorders and Cancer," Biochim. Biophys. Acta 1804:581-591 (2010).
Fryer, L. G. D., et al., "The Anti-Diabetic Drugs Rosiglitazone and Metformin Stimulate AMP-Activated Protein Kinase Through Distinct Signaling Pathways," J. Biol. Chem. 277:25226-25232 (2002).
Furukawa, S., et al., "Increased Oxidative Stress in Obesity and Its Impact on Metabolic Syndrome," J. Clin. Invest. 114(12):1752-1761 (2004).
Green, C. J., et al. "Elevated NF-kB Activation Is Conserved in Human Myocytes Cultured From Obese Type 2 Diabetic Patients and Attenuated by AMP-Activated Protein Kinase," Diabetes 60:2810-2819 (2011).
Gribble, A. D., et al., "ATP-Citrate Lyase as a Target for Hypolipidemic Intervention. Design and Synthesis of 2-Substituted Butanedioic Acids as Novel, Potent Inhibitors of the Enzyme," J. Med. Chem. 39:3569-3584 (1996).
Gupta, P. B., et al., "Cancer Stem Cells: Mirage or Reality?" Nat. Med. 15(9):1010-1012 (2009).
Gupta, P. B., et al., "Identification of Selective Inhibitors of Cancer Stem Cells by High-Throughput Screening," Cell 138:645-659 (2009).
Hansen, L. A., et al., "Retinoids in Chemoprevention and Differentiation Therapy," Carcinogenesis 21(7):1271-1279 (2000).
Hardie, D. G., "AMP-Activated Protein Kinase—an Energy Sensor that Regulates All Aspects of Cell Function," Genes Dev. 25:1895-1908 (2011).
Hatzivassiliou, G., et al., "ATP Citrate Lyase Inhibition Can Suppress Tumor Cell Growth," Cancer Cell 8:311-321 (2005).
Hayes, J. D., et al., "The Glutathione S-Transferase Supergene Family: Regulation of GST* and the Contribution of the Isoenzymes to Cancer Chemoprotection and Drug Resistance," Cult. Rev. Biochem. Mol. Biol. 30(6):445-600 (1995).
Hayes, J. D., et al., "Glutathione Transferases," Annu. Rev. Pharmacol. Toxicol. 45:51-88 (2005).
Heintz, D., et al., "Rapid Alteration of the Phosphoproteome in the Moss Physcomitrella Patens After Cytokinin Treatment," J. Proteome Res. 5:2283-2293 (2006).
Huang, G., et al., "Solid Lipid Nanoparticles of Temozolomide: Potential Reduction of Cardial and Nephric Toxicity," Int. J. Pharm. 355:314-320 (2008).
Hurt, E. M., et al., "Cancer Stem Cells: The Seeds of Metastasis?" Mol. Interv. 8:140-142 (2008).
Jakoby, W. B., "The Glutathione S-Transferases: A Group of Multifunctional Detoxification Proteins," Adv. Enzymol. Relat. Areas Mol. Biol. 46:383-414 (1978).
Kim, G.Y., et al., "Mechanisms of Signal Transduction: The Stress-Activated Protein Kinases p38alpha and JNK1 Stabilize p21 CIP1 by Phosphorylation," J. Biol. Chem. 277:29792-29802 (2002).
Kim, S.H. et al. "Vitisin A Inhibits Adipocyte Differentiation Through Cell Cycle Arrest in 3T3-L1 Cells," Biochem. Biophys. Res. Commun. 372:108-113 (2008).
Kim, S.N., et al., "Regulation of Adipocyte Differentiation by Histone Deacetylase Inhibitors," Arch. Pharm. Res. 32 (4):535-541 (2009).
Kitange, G. J., et al., "Induction of MGMT Expression is Associated with Temozolomide Resistance in Glioblastoma Xenografts," Neuro-Oncology 11:281-291 (2009).

(56) References Cited

OTHER PUBLICATIONS

LaBorde, E., "Glutathione Transferases as Mediators of Signaling Pathways Involved in Cell Proliferation and Cell Death," Cell Death and Differentiation 17:1373-1380 (2010).

Lapidot, T., et al., "A Cell Initiating Human Acute Myeloid Leukaemia After Transplantation into SCID Mice," Nature 367:645-648 (1994).

Leszczyniecka, M., et al., "Differentiation Therapy of Human Cancer: Basic Science and Clinical Applications," Pharmacol. Ther. 90:105-156 (2001).

Li, J. J., et al., "2-Hydroxy-N-Arylbenzenesulfonamides as ATP-Citrate Lyase Inhibitors," Bioorg. Med. Chem. Letters 17:3208-3211 (2007).

Linos, E., et al., "Increasing Burden of Melanoma in the United States," J. Invest. Dermatol. 129(7):1666-1674 (2009).

Liu, H., et al., "Cancer Stem Cells from Human Breast Tumors are Involved in Spontaneous Metastases in Orthotopic Mouse Models," PNAS 107(42):18115-18120 (2010).

\* cited by examiner

Fig. 2
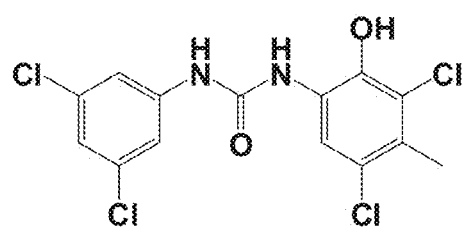
COH-SR9
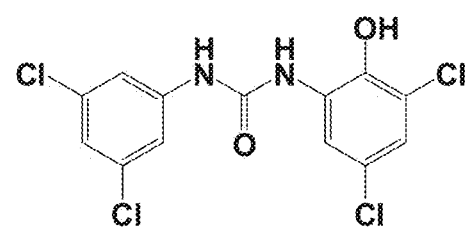
COH-SR10
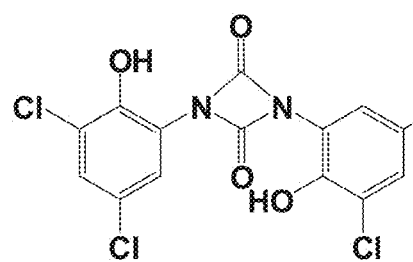
COH-SR11
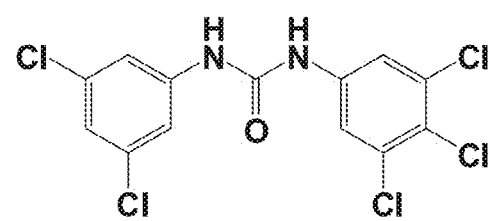
COH-SR12
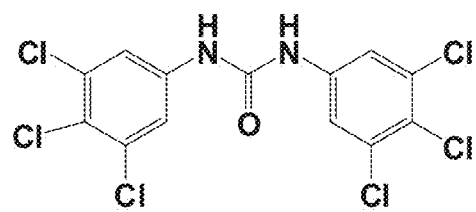
COH-SR13
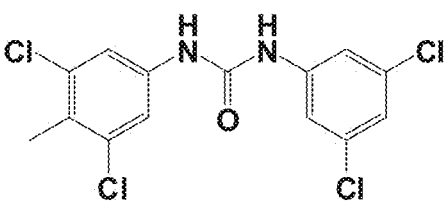
COH-SR14
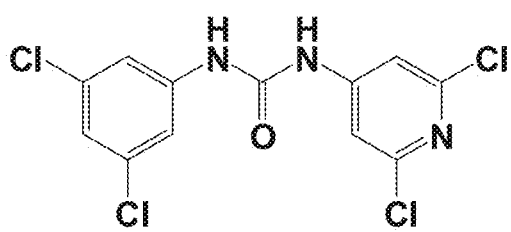
COH-SR16
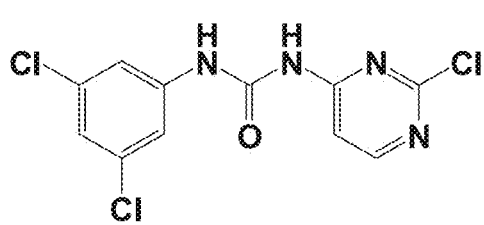
COH-SR18

Fig. 3
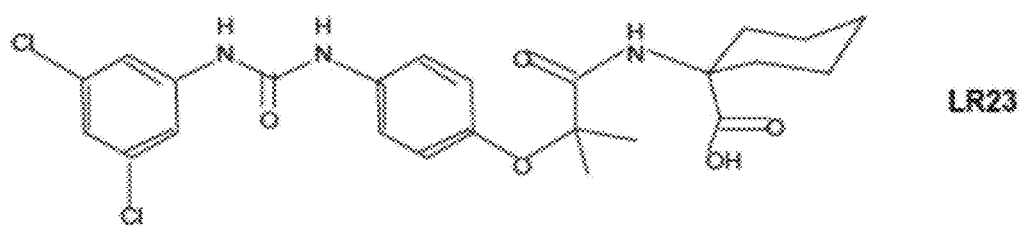
LR23
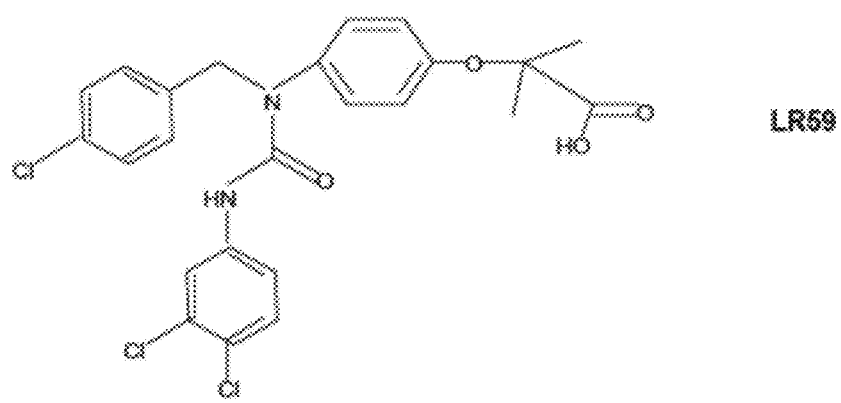
LR59
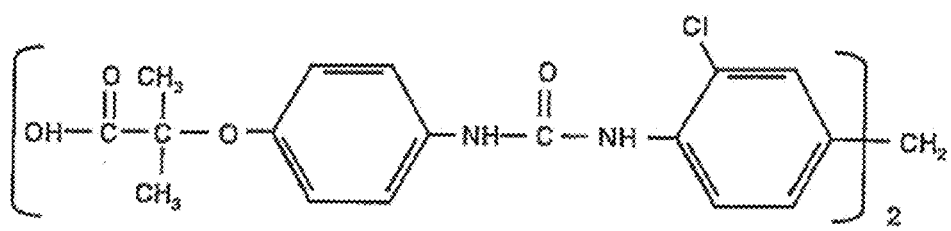
LR-90
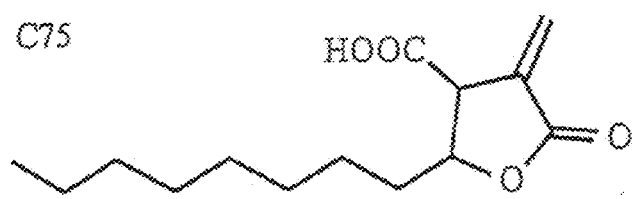
C75

Fig. 9
A)
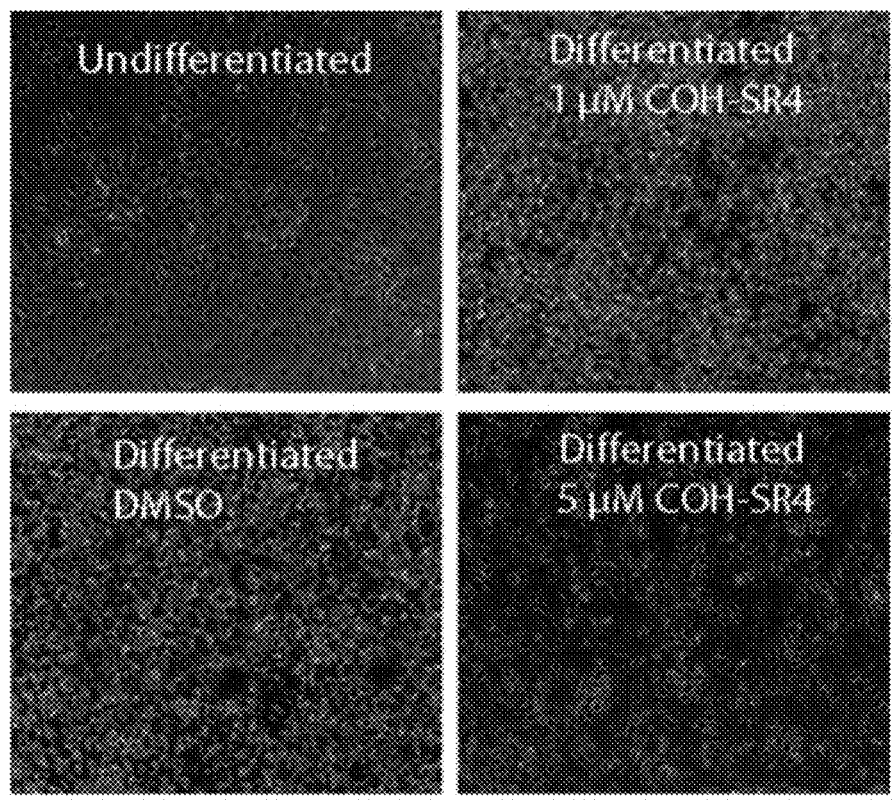
B)
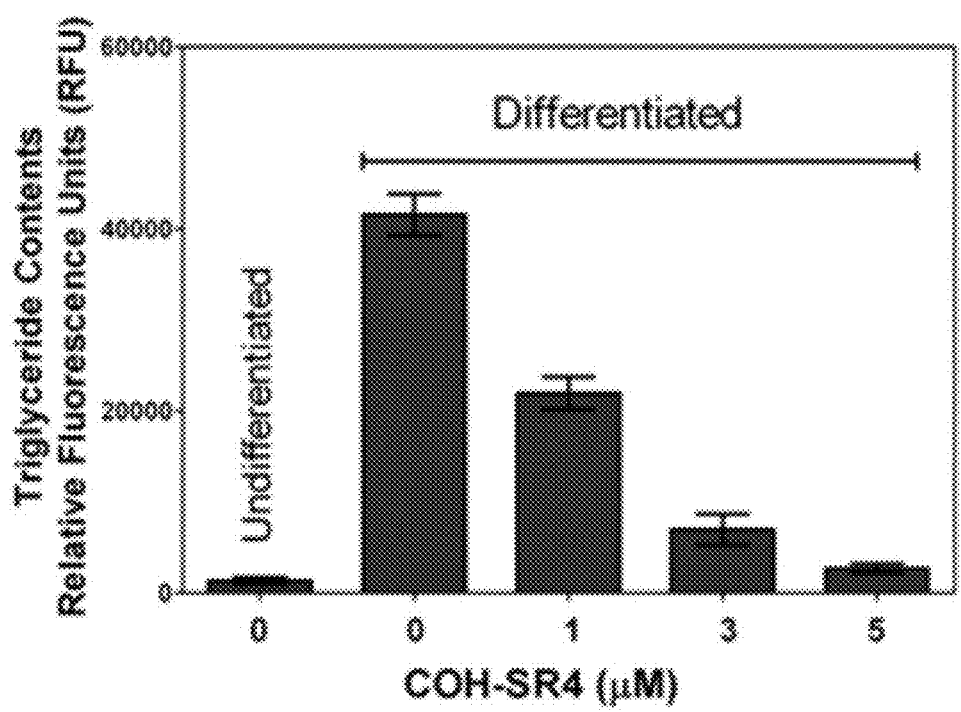

c)

Fig. 10
(A)
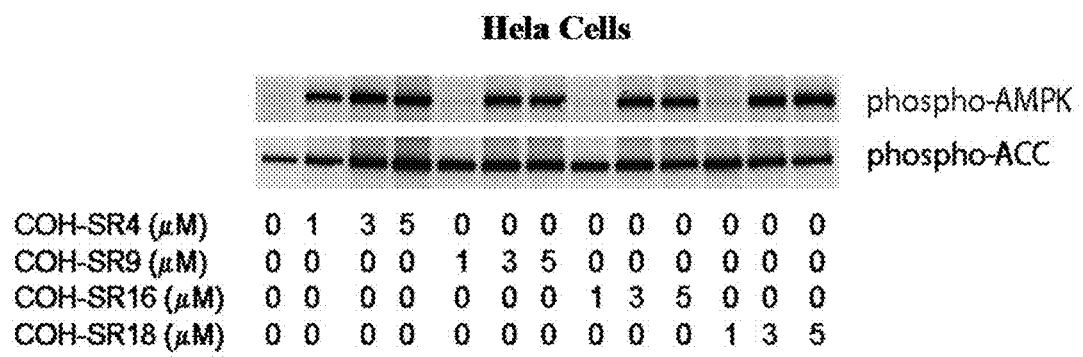
(B)
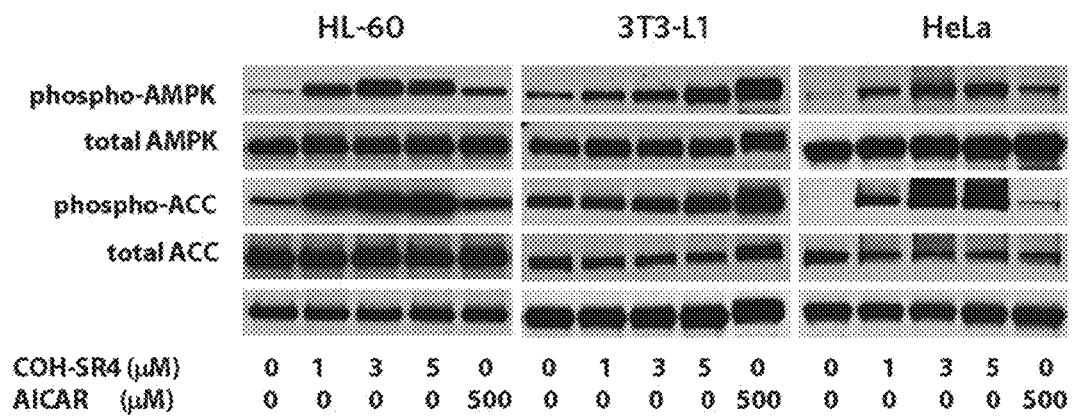

Fig. 11
(A)
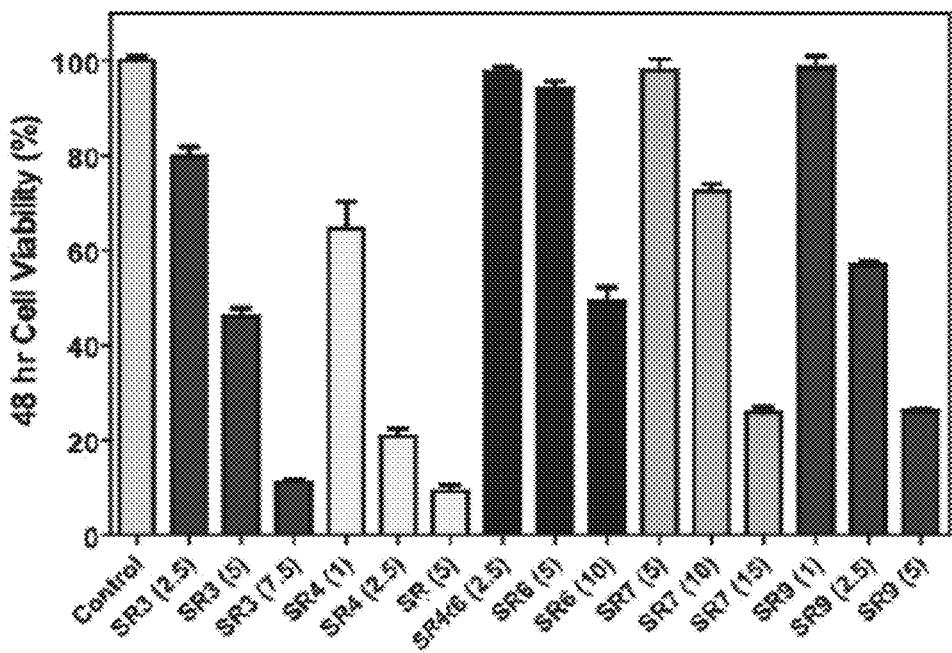
(B)
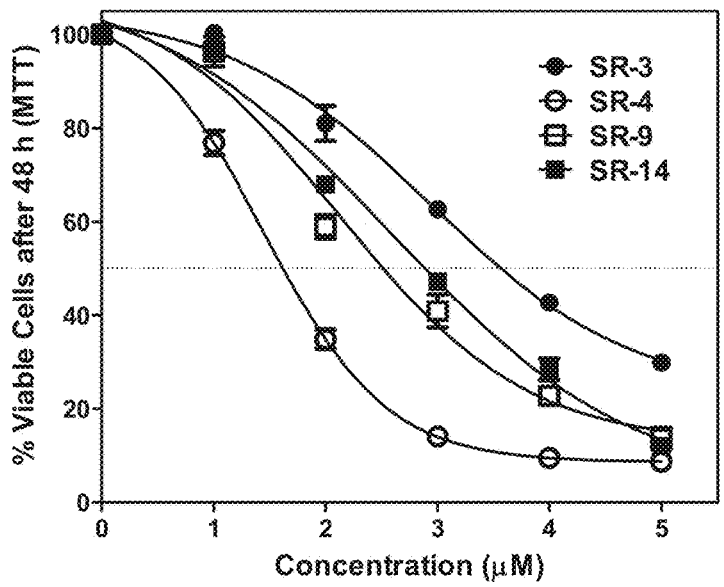

Fig. 12
(A)
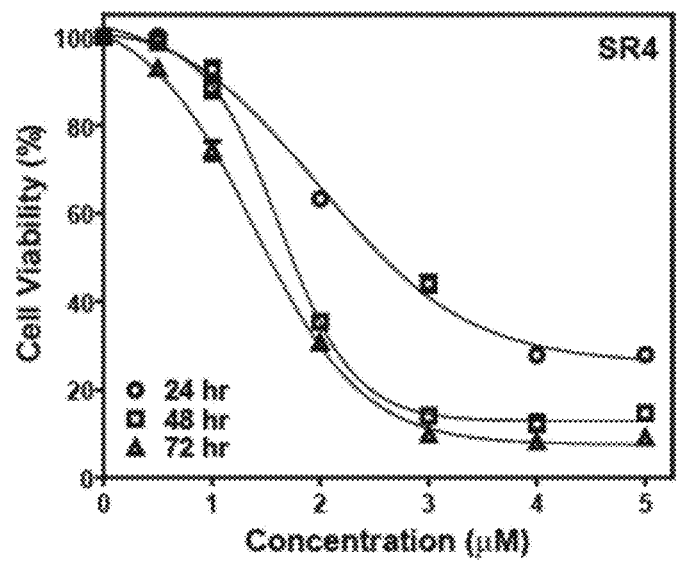
(B)
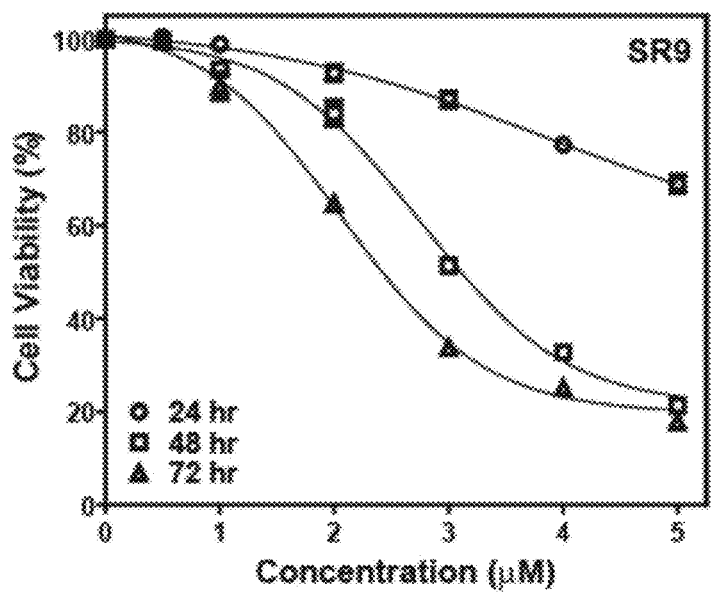

Fig. 14
A)
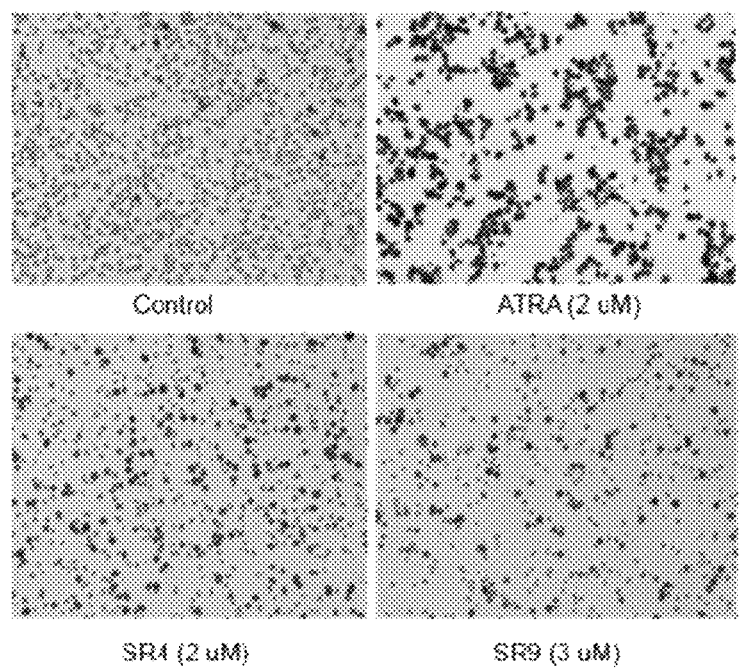
B)
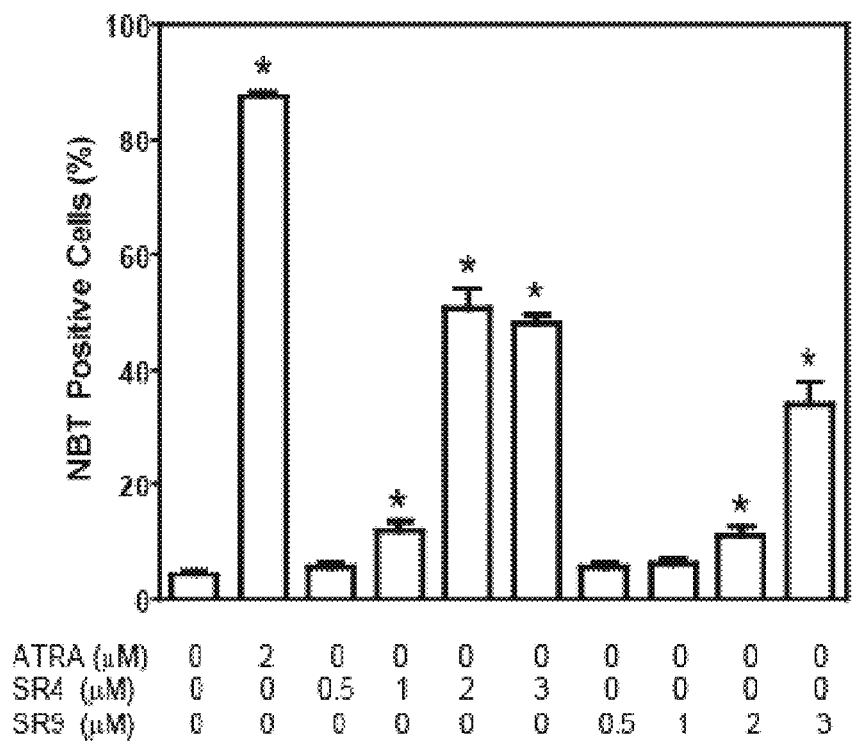

Fig. 14 (cont.)
C)
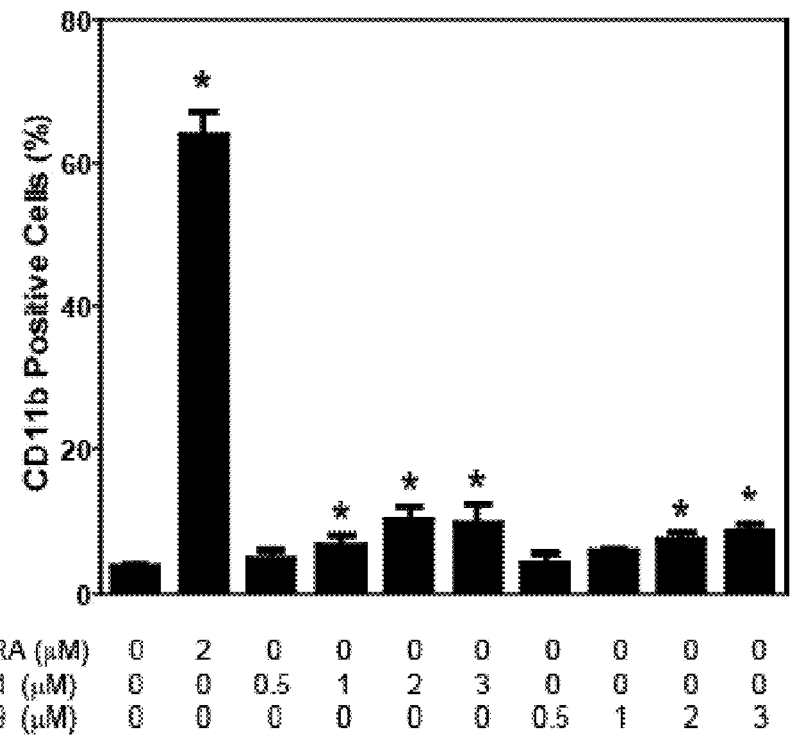
D)
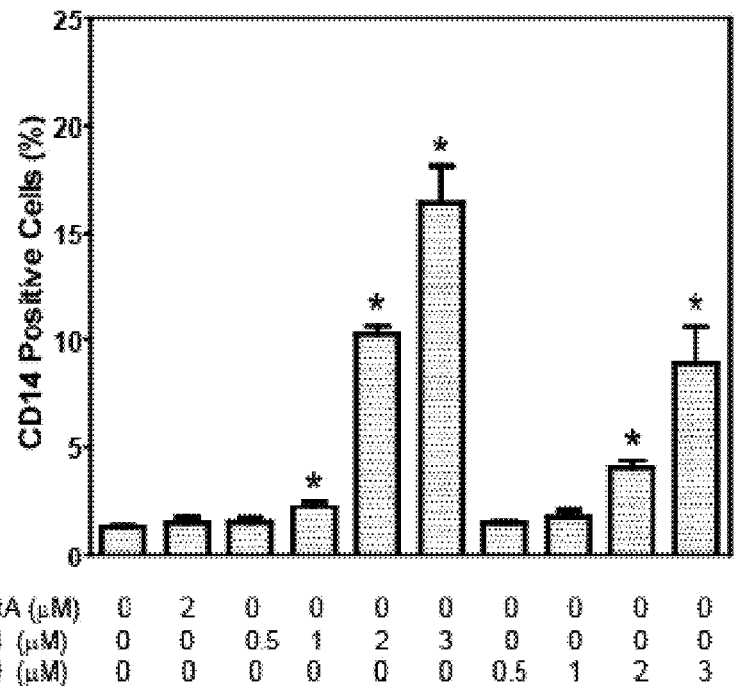

Fig. 15
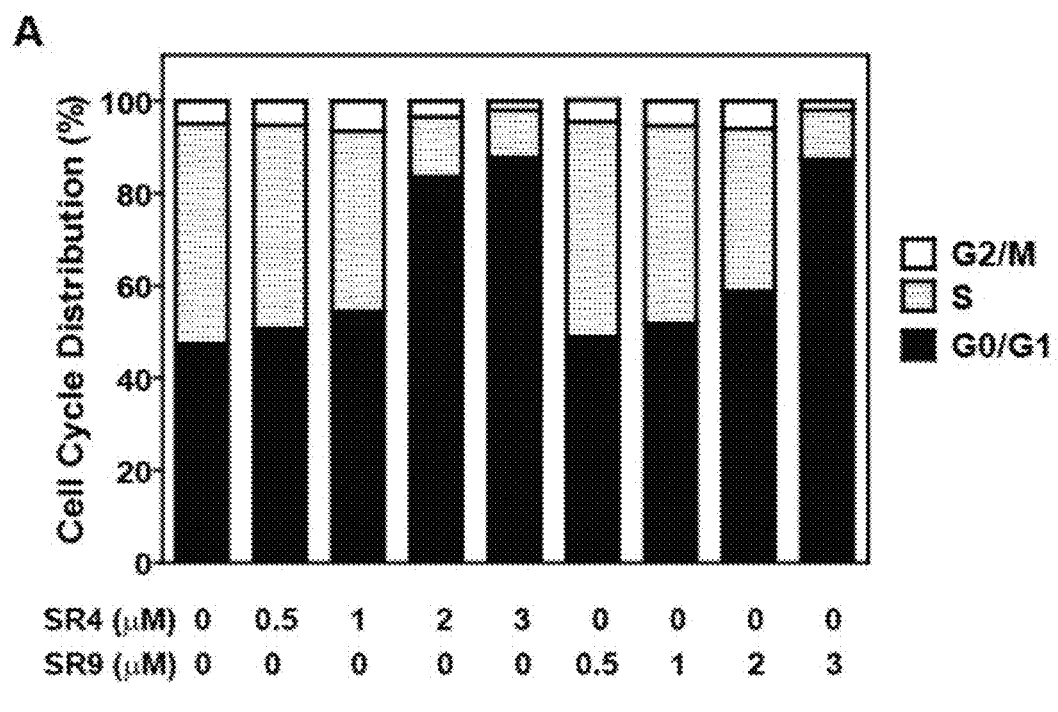
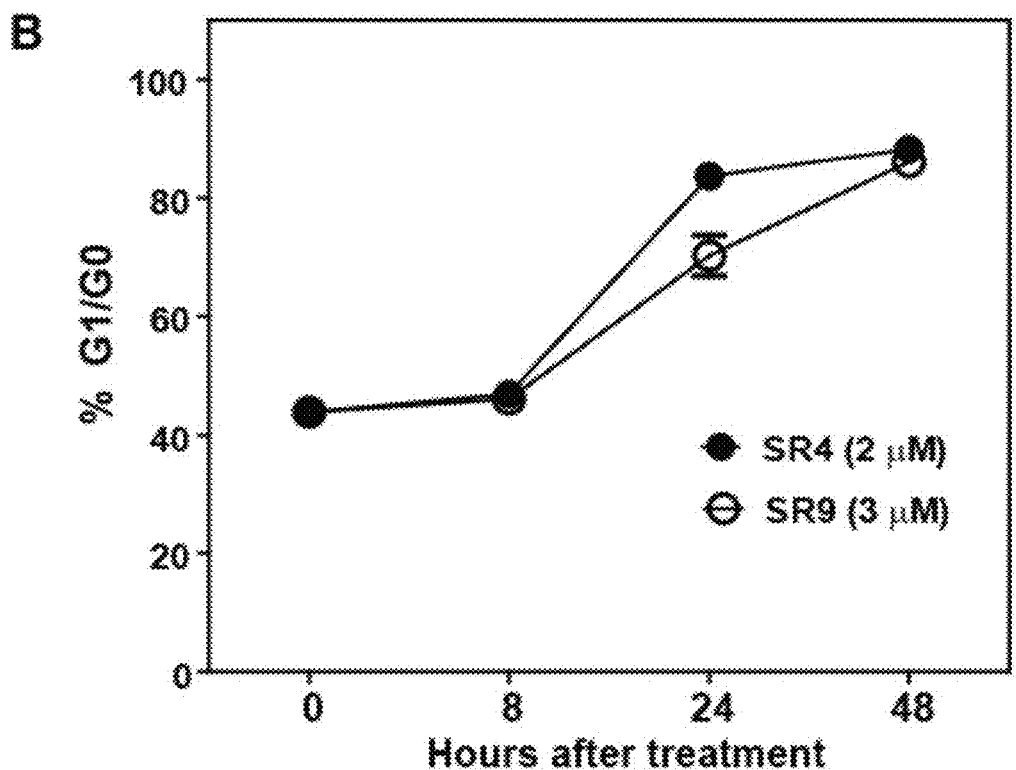

A)

B)

C)

E)

Annexin-FITC Log
SR4 2 uM

F)

G)

H)

Fig. 17
A)
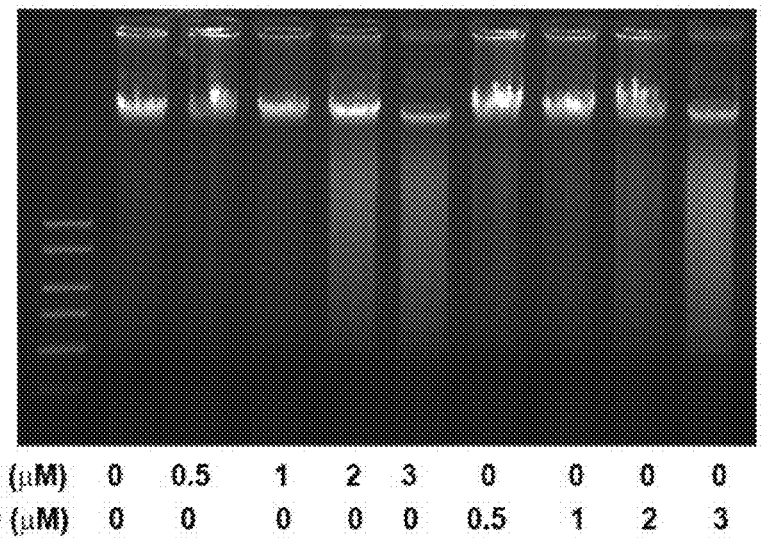
B)
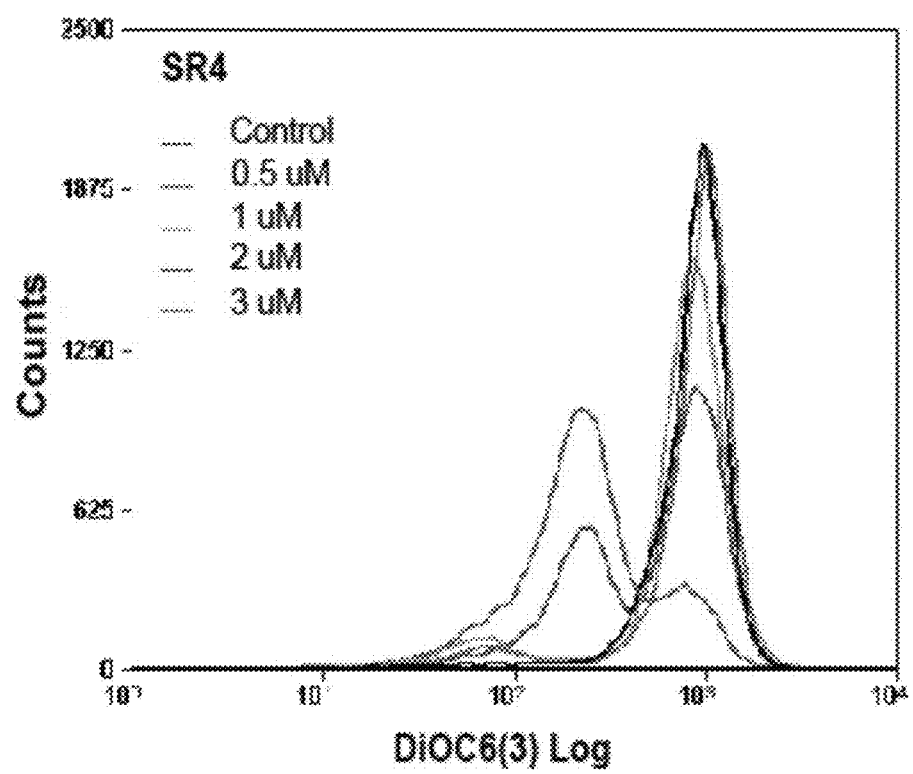

C)

Fig. 18
(A)
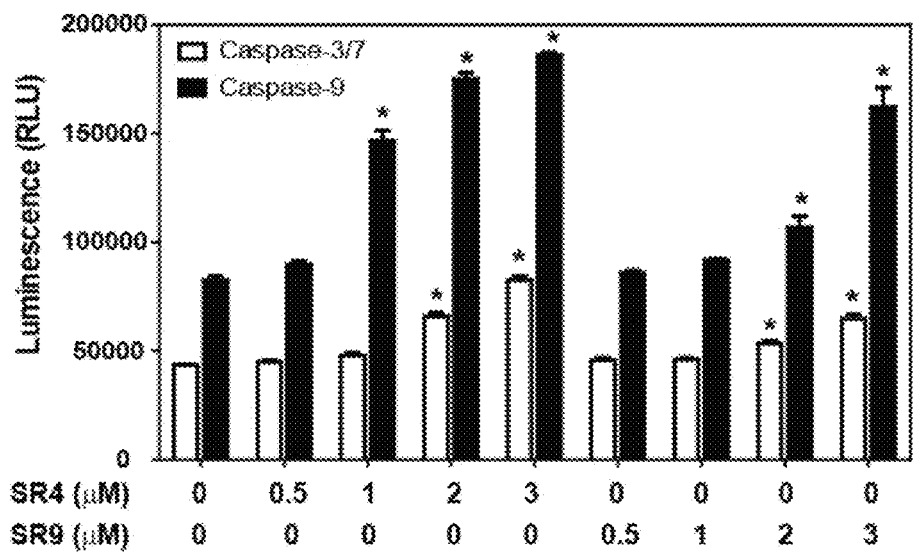
(B)
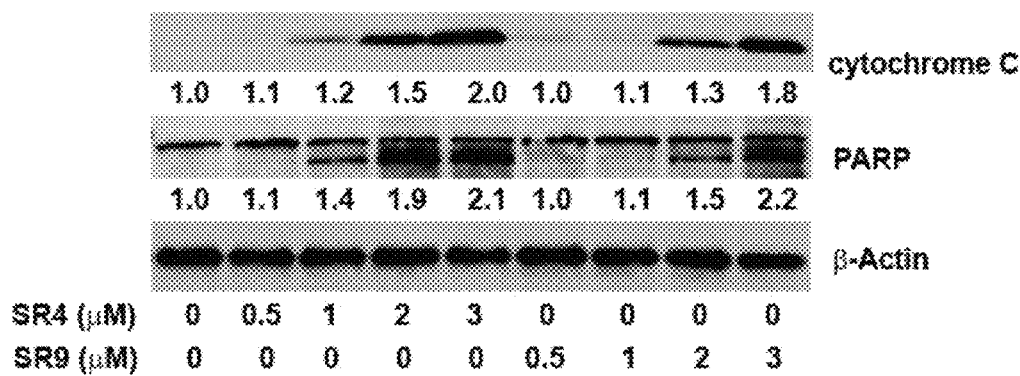

Fig. 20
MCF-7
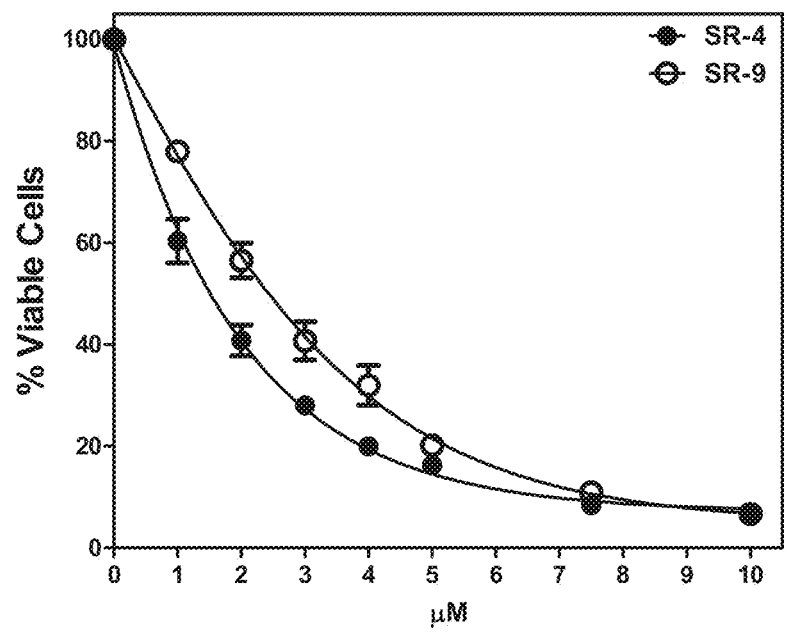
MDA-MB-231
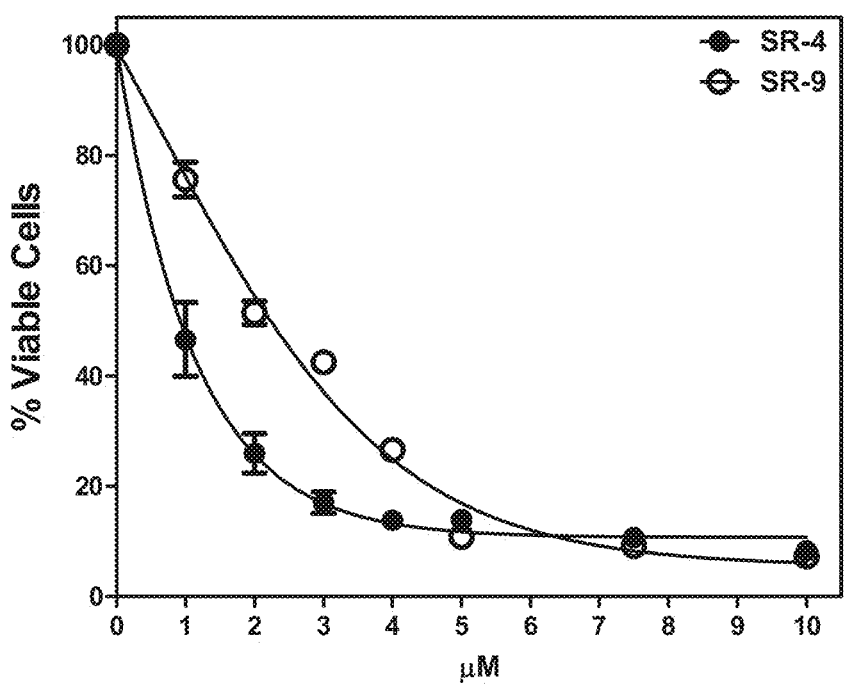

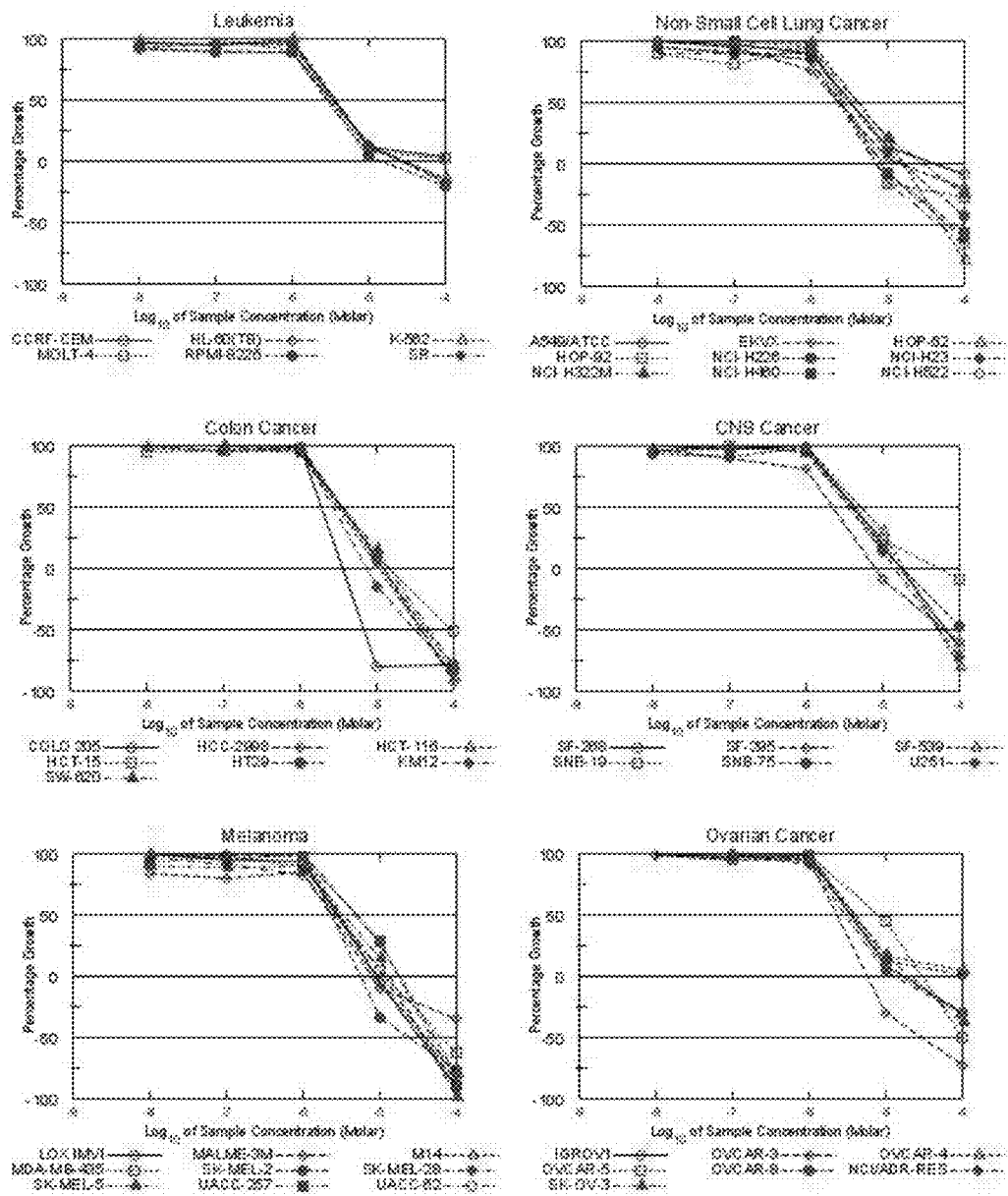

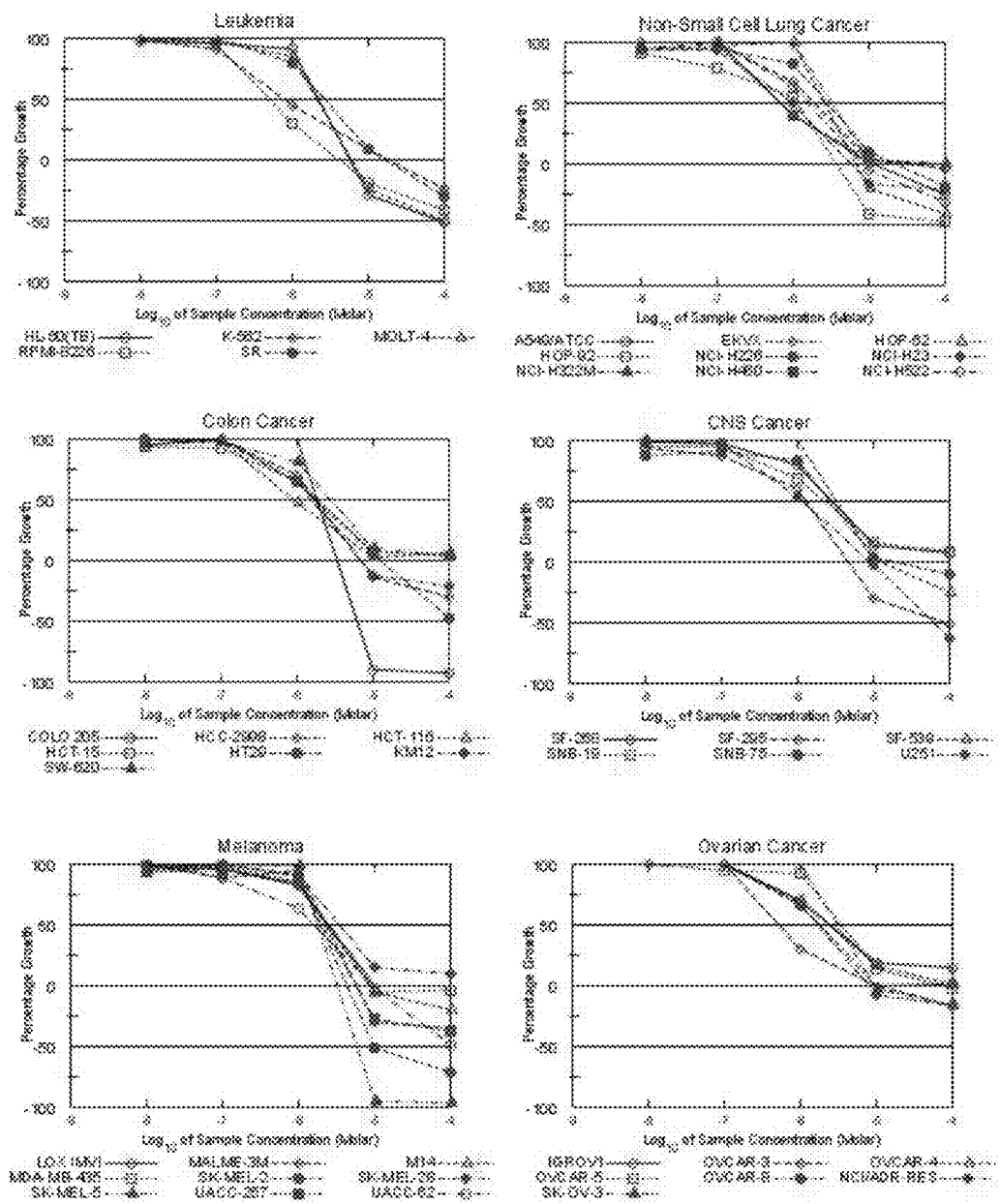

Fig. 29
(A)
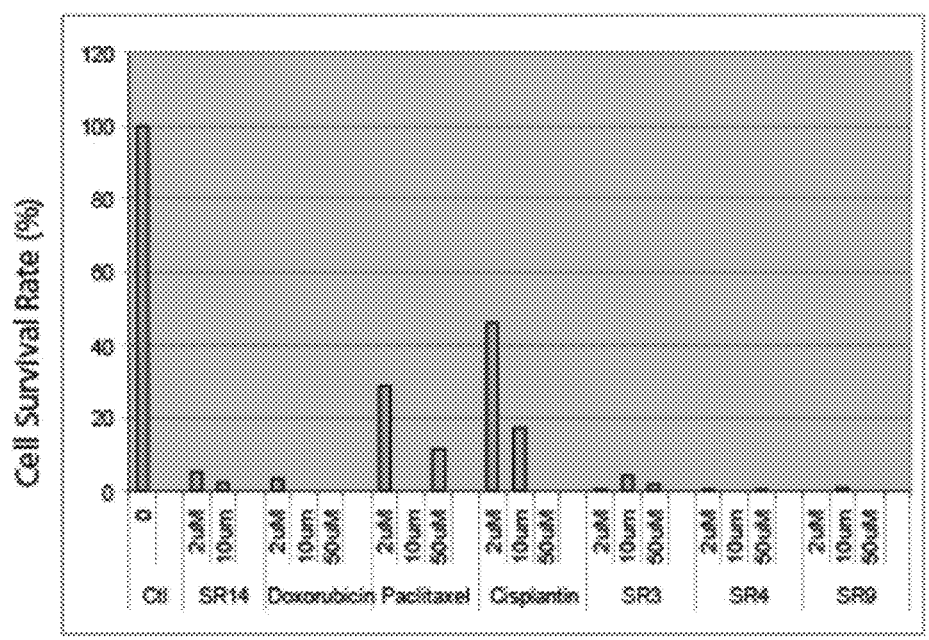
(B)
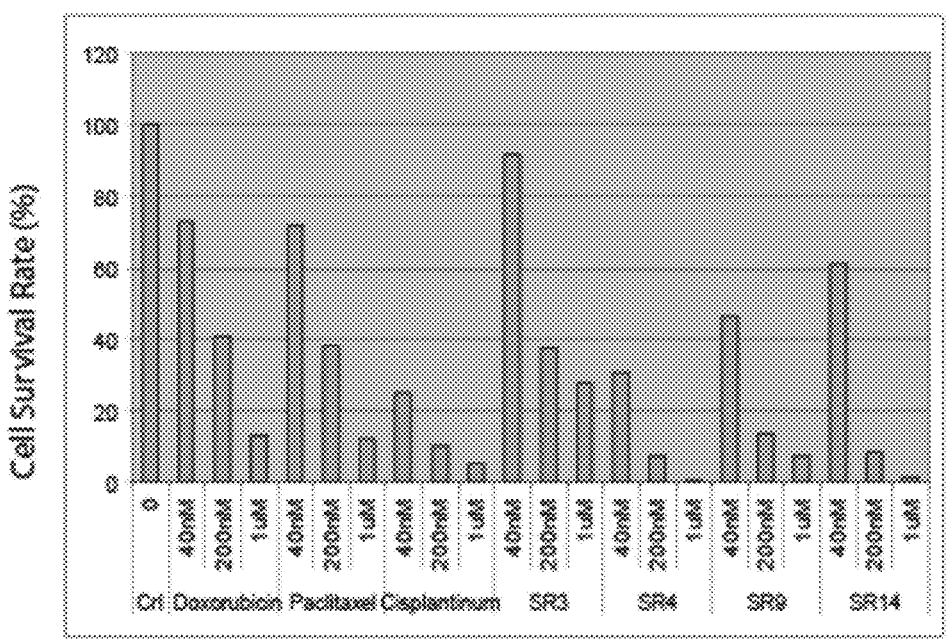

Fig. 32
(A)
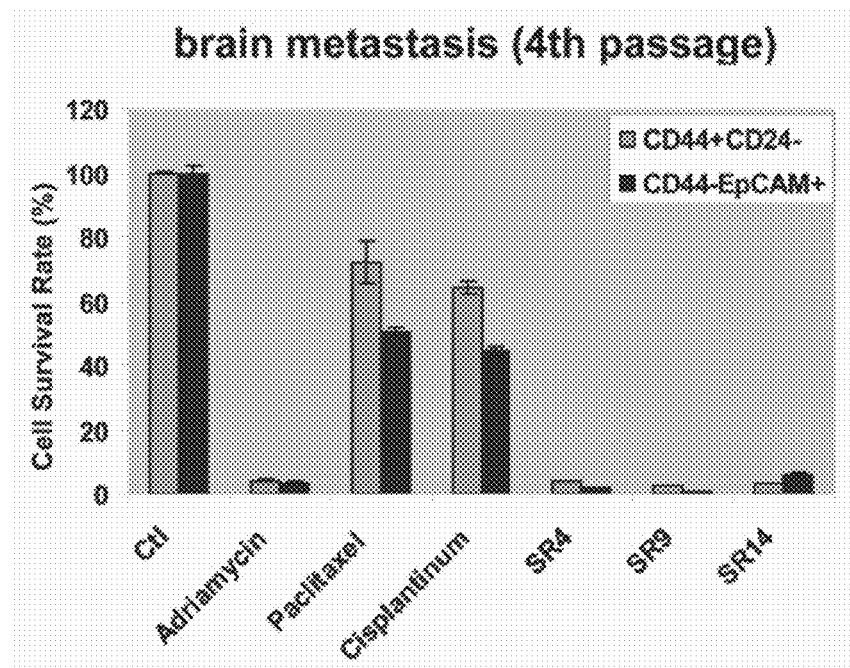
(B)
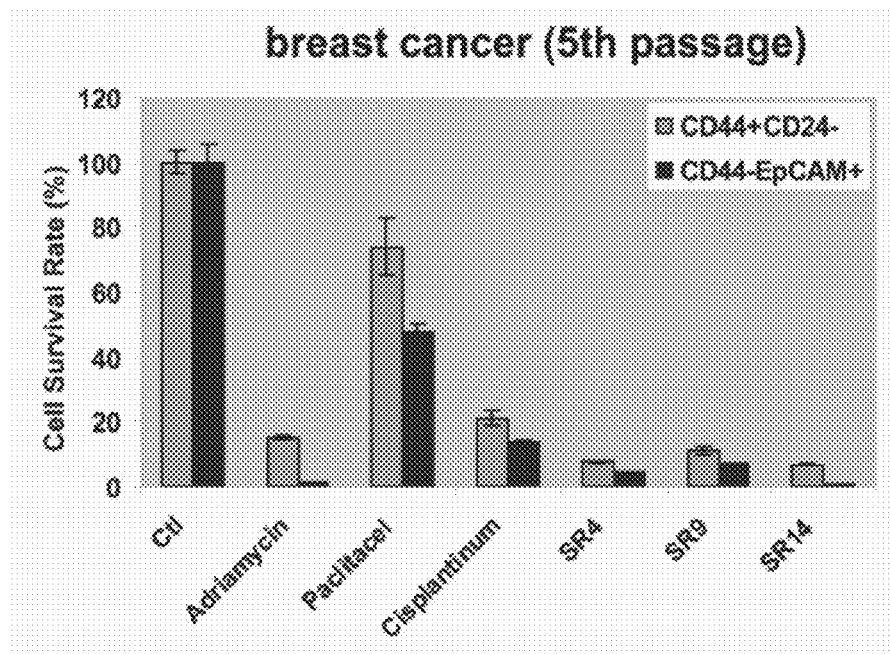

Fig. 33
(A)
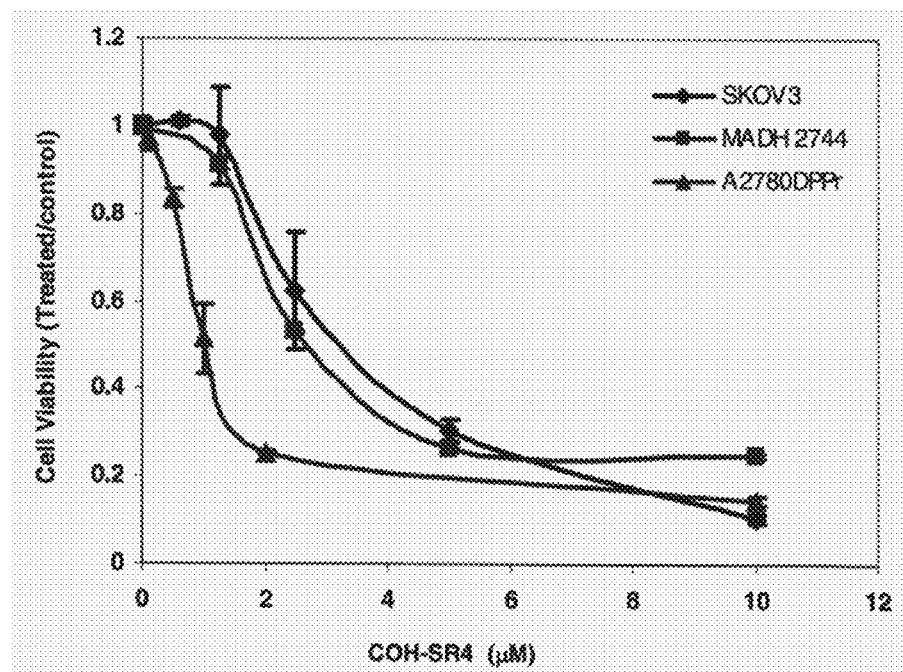
(B)
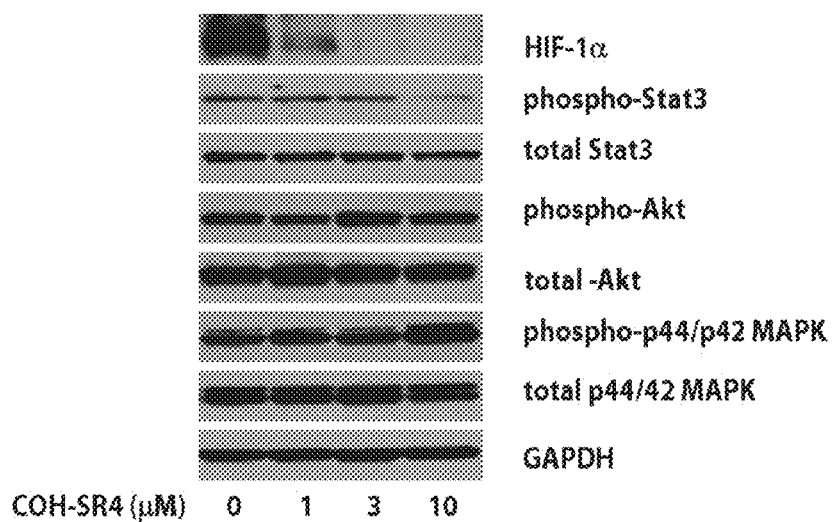

Fig. 34
(A)
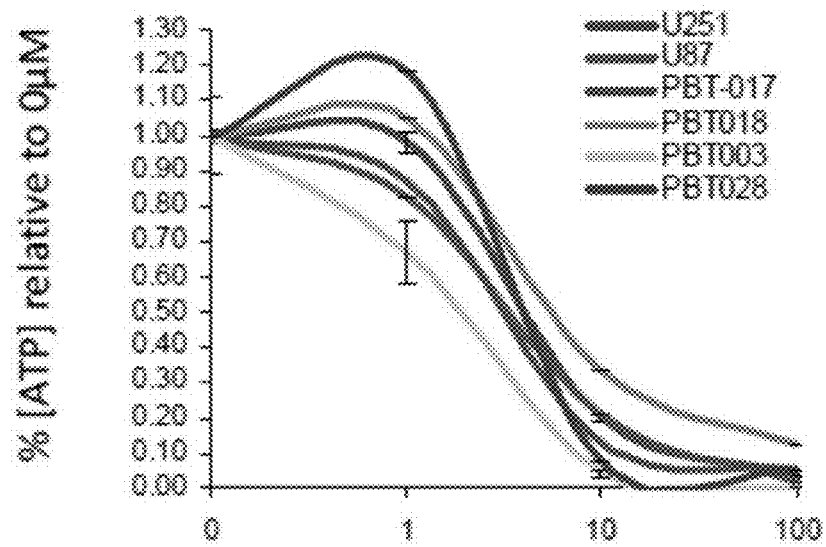
(B)
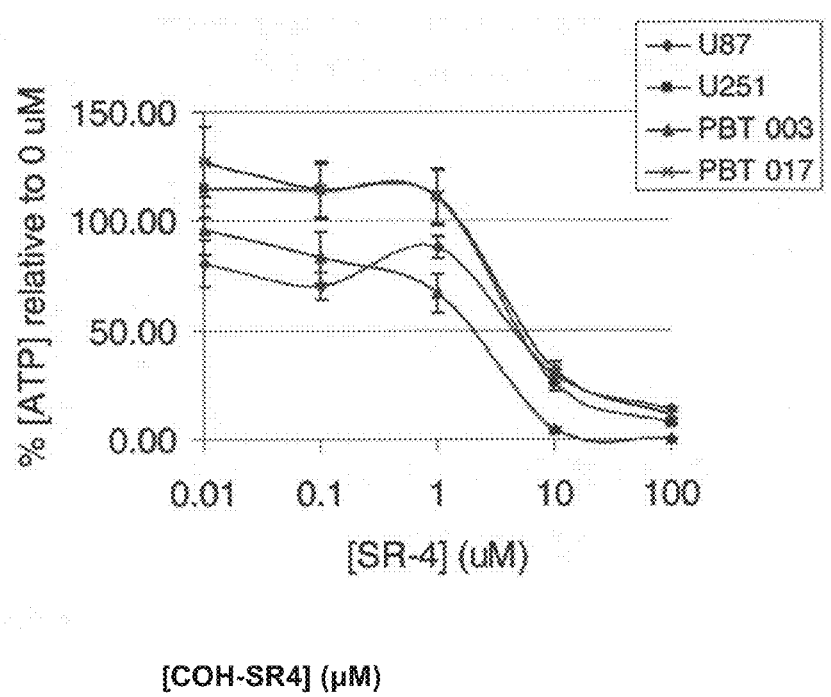
[COH-SR4] (μM)

Fig. 35
(A)
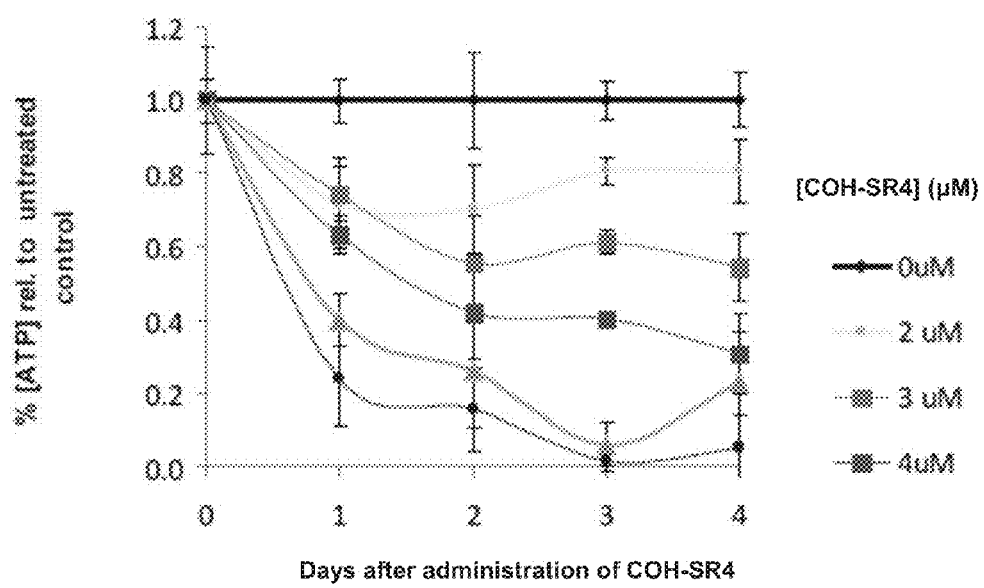
(B)
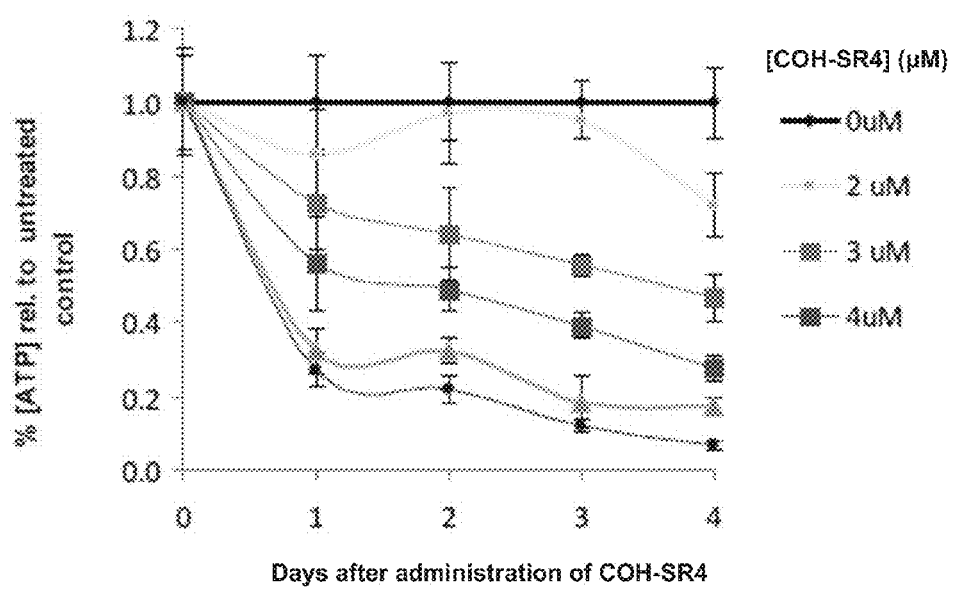

Fig. 37
(A)
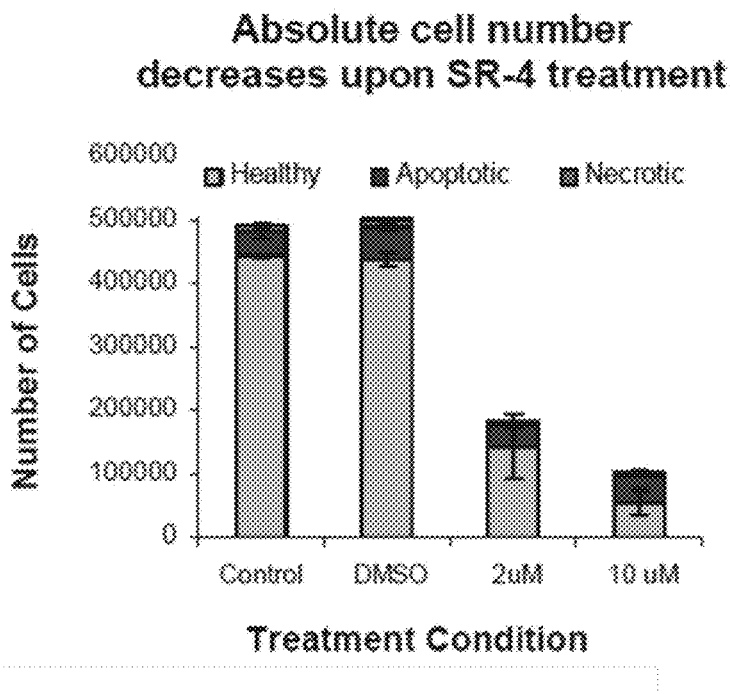
(B)
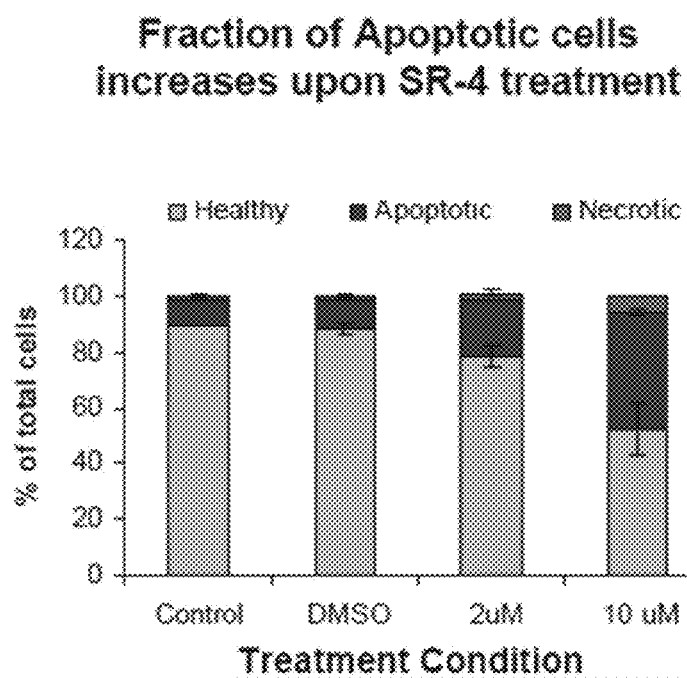

Fig. 39
(A)
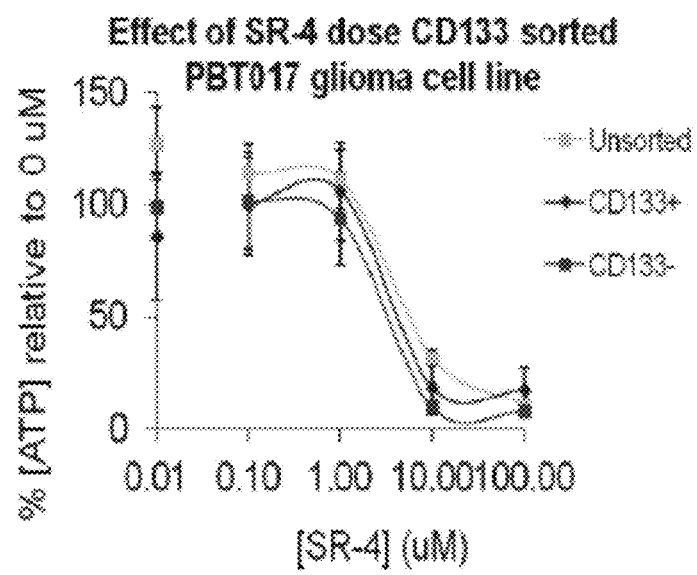
(B)
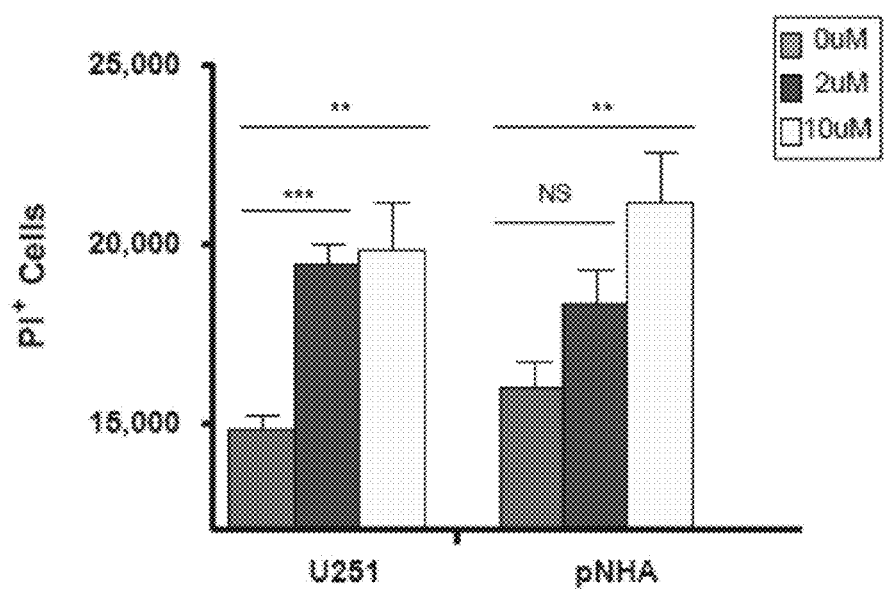

Fig. 43
(A) [COH-SR4] (μM)
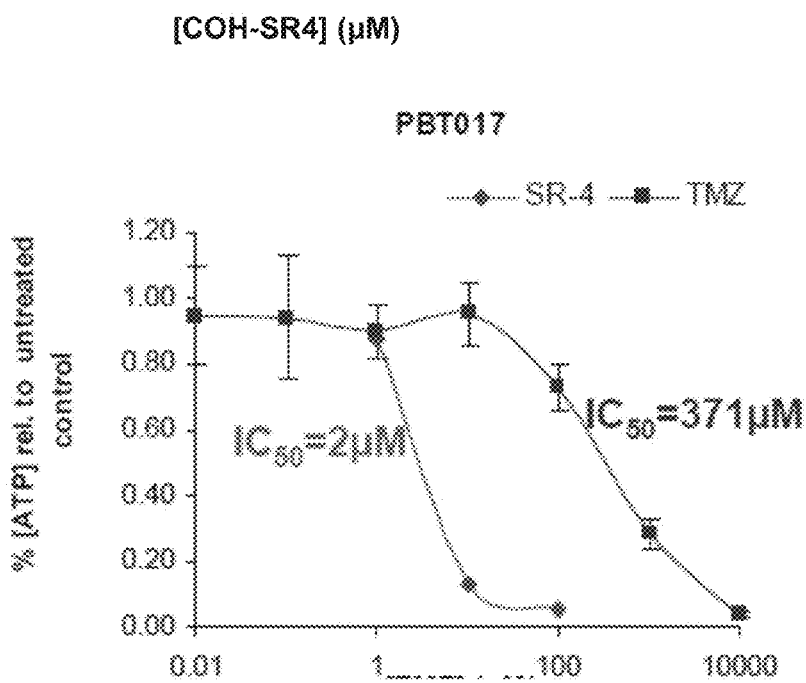
(B) [COH-SR4] (μM)
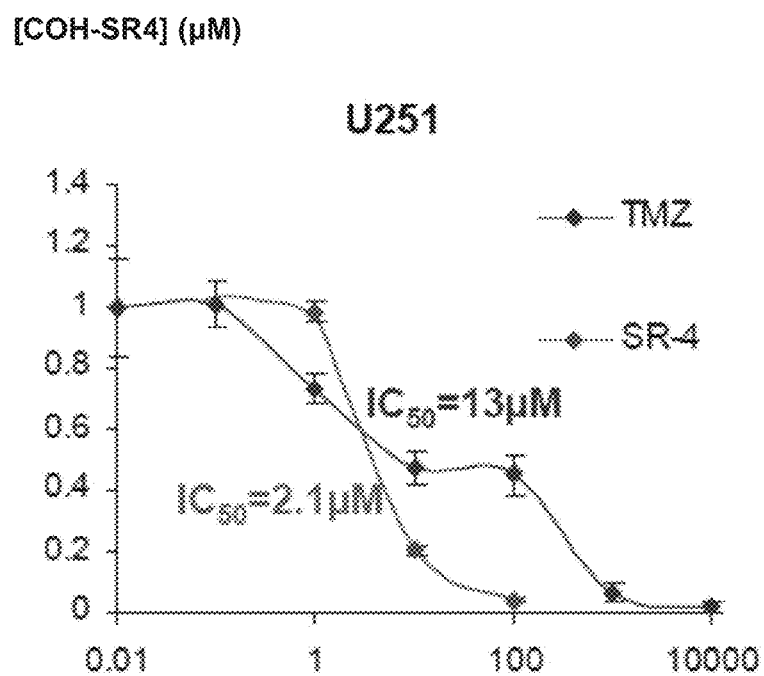

Fig. 44
(A) 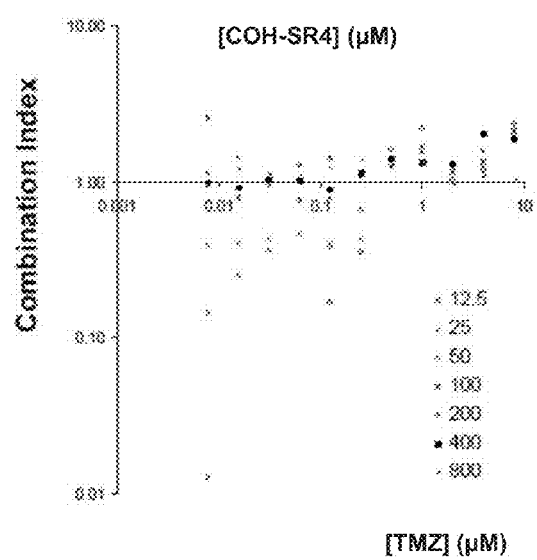
(B) 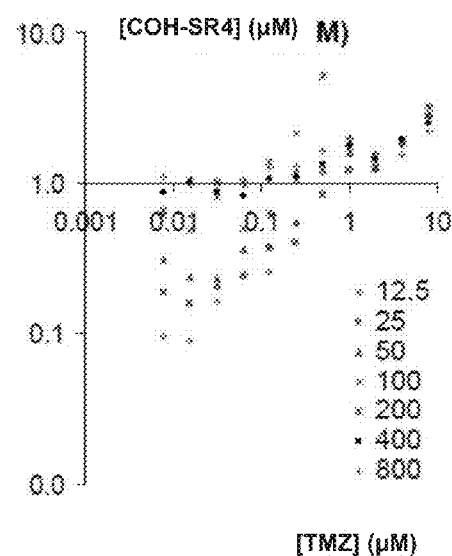

Fig. 45
(A)
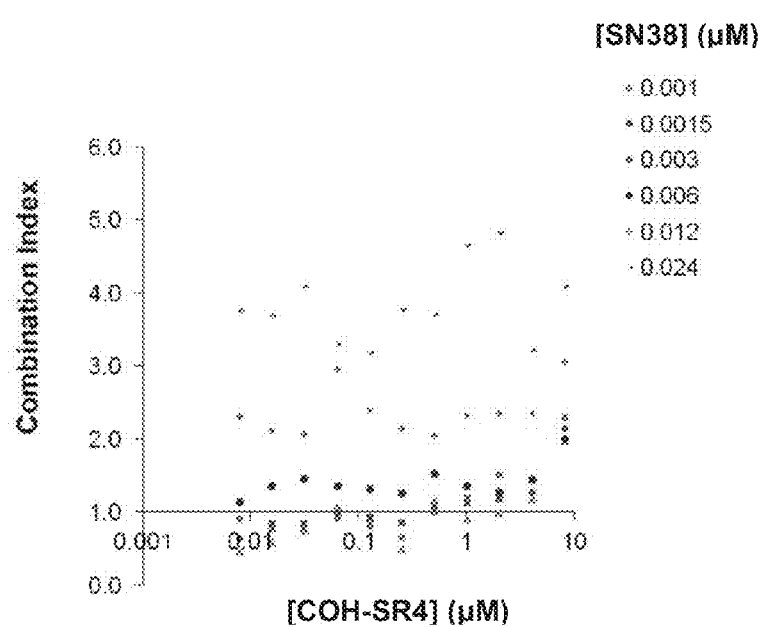
(B)
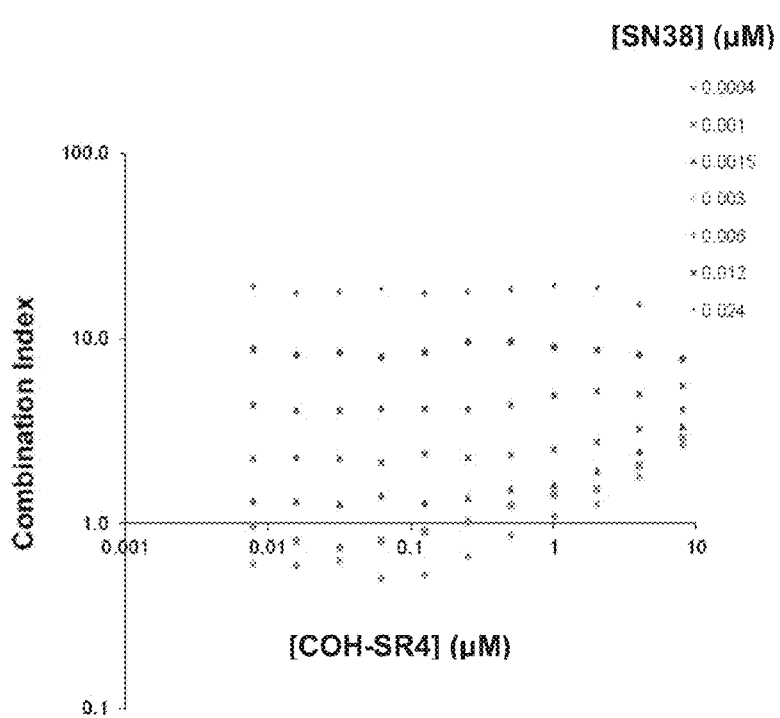

COH-SR4  GSH  GSR4

Fig. 54
(A)
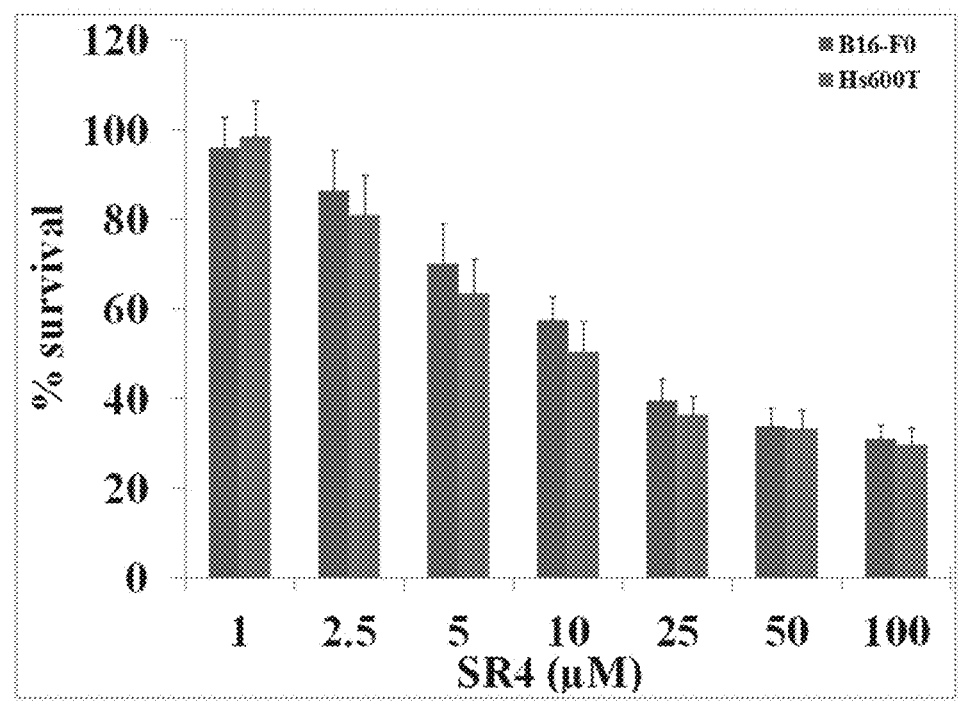
(B)
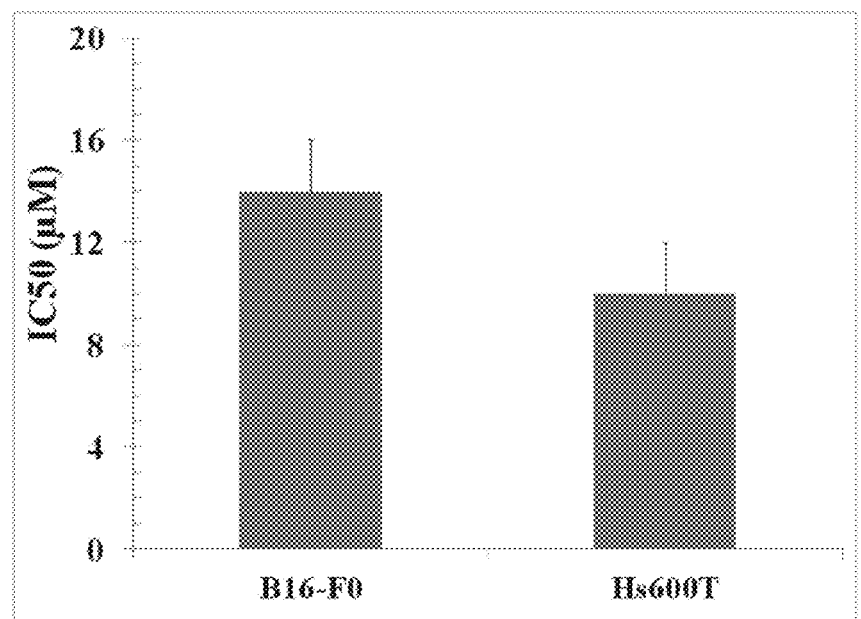

Fig. 55
(A)
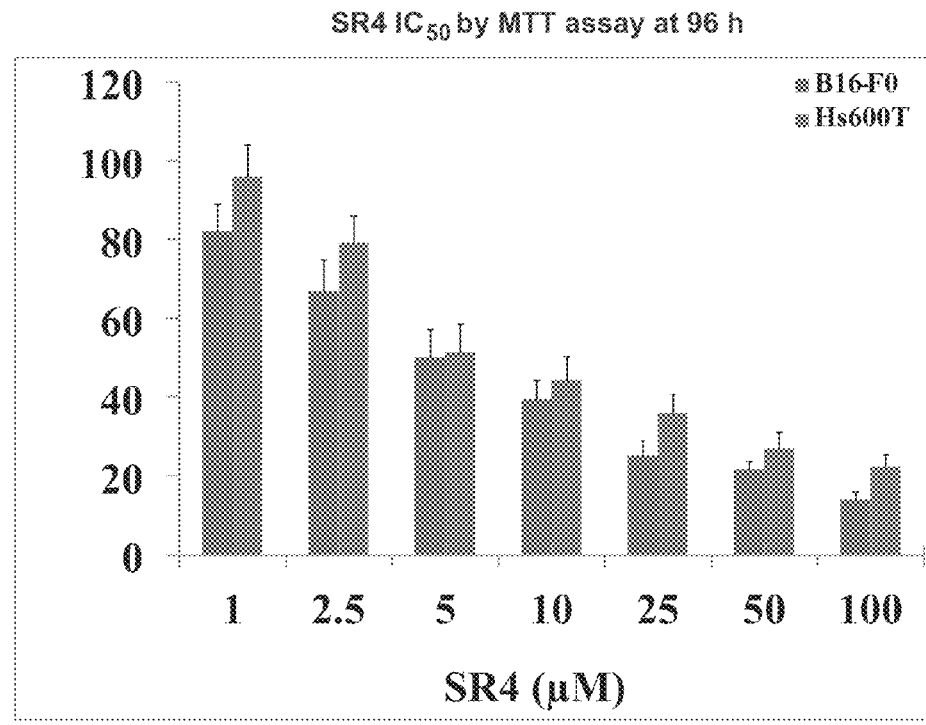
(B)
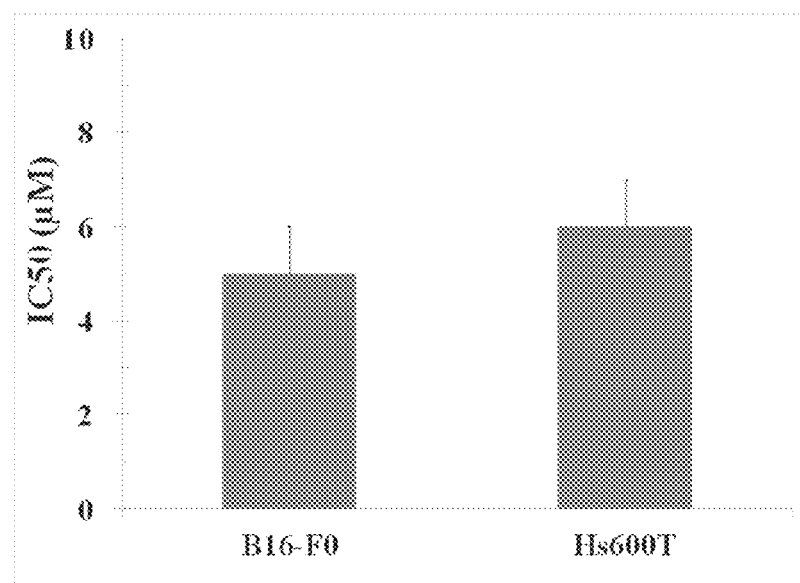

Fig. 56
Control 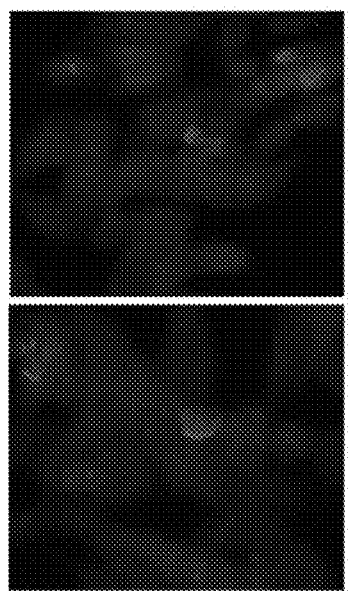
COH-SR4 treated 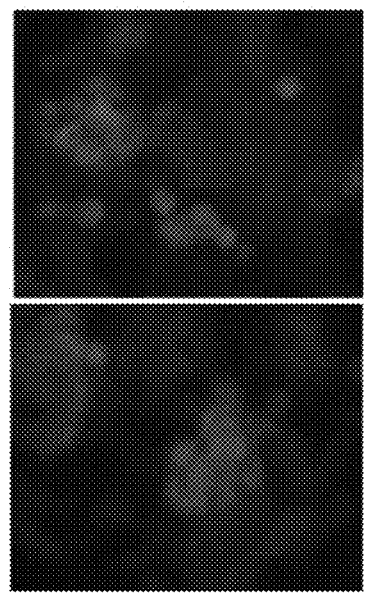

Fig. 59
A)
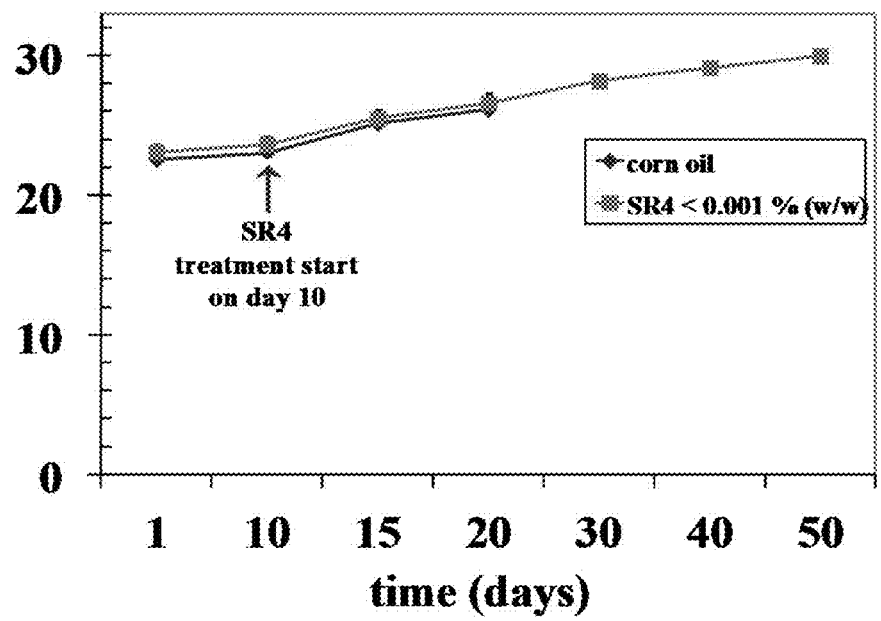
B)
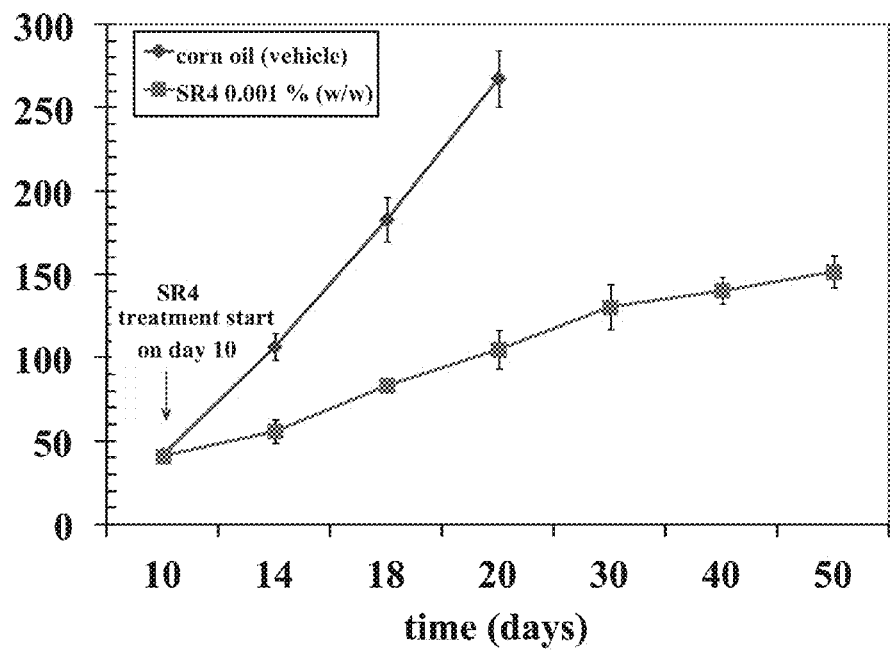

US 10,029,991 B2

MODULATORS OF DEVELOPMENT OF ADIPOCYTE AND CANCER CELLS

CROSS-REFERENCE TO RELATED APPLICATIONS

The present application is a continuation of International Application No. PCT/US2012/023034, filed Jan. 27, 2012, which claims priority to U.S. Provisional Application No. 61/436,958, filed Jan. 27, 2011, which is incorporated herein by reference in their entireties.

FIELD OF THE INVENTION

This invention relates to the field of new compounds and pharmaceutical compositions thereof, and methods of using these new compounds to provide treatment/prevention of obesity and/or cancers.

BACKGROUND OF THE INVENTION

The intake of calorie-rich fast food and sedentary lifestyles of developed countries has sharply increased the incidence of obesity. The obesity pandemic is thought to be associated with a sedentary lifestyle and the overconsumption of energy-rich food. Obesity is not only a serious health and economic burden, but also predisposes a person to a variety of metabolic diseases (i.e., the coexistence of several risk factors for atherosclerosis, hyperglycemia, dyslipidemia, and hypertension). Obesity occurs when adipose cells increase excessively in size (hypertrophy) and/or number (hyperplasia). Animal studies suggest that hyperplasia occurs in 2 steps: an increase in numbers of preadipocytes and differentiation of preadipocytes into mature (adipokine-secreting) adipocytes.

Anti-obesity strategies are classified into four categories: reducing food intake, blocking nutrient absorption, increasing thermogenesis, and modulating fat or protein metabolism or storage. There are currently two drugs approved by the FDA for the treatment of obesity. These include orlistat that blocks the absorption of dietary fat, and sibutramine, a specific re-uptake inhibitor for norepinephrine and serotonin that acts in the central nervous system (CNS) to reduce energy intake. These drugs have limited efficacies and side effects are commonly reported, which are further confounded by diminishing response in the long-term treatment of obesity. Moreover, anti-obesity drug development strategy continues to focus on either central or peripheral acting inhibitors of food intake, which will likely encounter similar problems.

Adipocyte differentiation has often been a target of anti-obesity strategies, because obesity is caused not only by hypertrophy of adipocytes, but also by adipocyte hyperplasia. Blocking of adipocytes differentiation is one of the anti-obesity strategies falling under the category of modulating fat storage.

Furthermore, modulation of the state of differentiation and growth of cancer cells, i.e. differentiation therapy may be beneficial to cancer treatments.

The current drugs used in cancer treatment are highly toxic and often non-specific. Current anticancer therapy strategies are more focused on rapid proliferating cells, which can shrink primary and metastatic tumors, but such effects are usually transient and tumor relapse of most metastatic cancers frequently occur. One possible reason for failure is the existence of cancer stem cells. Unlike most cells within the tumor, cancer stem cells are resistant to well-defined chemotherapy, and after treatment, they can regenerate all the cell types in the tumor through their stem cell-like behavior of largely quiescent nature and their abundant expression of drug transporters.

Therefore, there exists a need to find new compounds that can modulate cell cycle of adipocyte and/or cancer cells to provide treatment or prevention of obesity and/or cancers.

SUMMARY OF THE INVENTION

One aspect of the disclosure relates to a COH-SR compound selected from the group consisting of COH-SR1, COH-SR2, COH-SR3, COH-SR4, COH-SR5, COH-SR6, COH-SR7, COH-SR8, COH-SR9, COH-SR10, COH-SR11, COH-SR12, COH-SR13, COH-SR14, COH-SR16, COH-SR18, LR23, LR59, and the pharmaceutically acceptable derivative, solvates, salts and stereoisomers thereof, including mixtures thereof in all ratios.

Another aspect of the disclosure relates to a pharmaceutical composition comprising a therapeutically effective amount of a COH-SR compound.

Another aspect of the disclosure relates to a method of treating or preventing obesity in a subject comprising administering to the subject a pharmaceutical composition disclosed herein.

Another aspect of the disclosure relates to a method of treating cancer in a subject comprising administering to the subject a pharmaceutical composition disclosed herein.

BRIEF DESCRIPTION OF DRAWINGS

FIG. 2: Chemical structures of COH-SR9, COH-SR10, COH-SR11, COH-SR12, COH-SR13, COH-SR14, COH-SR16, and COH-SR18.

FIG. 3: Chemical structures of LR23, LR59, LR-90 and C75.

FIG. 10: (A) Dose-dependent AMPK activation by COH-SR4, COH-SR9, COH-SR16, and COH-SR18 in Hela cells; (B) Dose-dependent AMPK activation by COH-SR4 in Hela, HL-60 and 3T3-L1 cells.

FIG. 11: (A) COH-SR3, COH-SR4, COH-SR6, COH-SR7, and COH-SR9, inhibited growth and proliferation of HL-60 cells, incubation time was 48 hours; (B) Dose-dependent effects of COH-SR3, COH-SR4, COH-SR9, and COH-SR14 on cell viability of HL-60 cells, incubation time was 48 hours.

FIG. 12: (A) Dose and time-dependent effects of COH-SR4 on cell viability of HL-60 cells; and (B) Dose and time-dependent effects of COH-SR9 on cell viability of HL-60 cells.

FIG. 14: COH-SR4 and COH-SR9 induced superoxide production of HL-60 cells. (A) NBT-stained cells; (B) quantity of NBT positive cells; (C) effects on surface antigen expression of CD11b; and (D) effects on surface antigen expression of CD14.

FIG. 18: COH-SR4 and COH-SR9 induced apoptosis of HL-60. (A) Effects of COH-SR4 and COH-SR9 on caspase activation; (B) COH-SR4 and COH-SR9 triggered cytochrome c release and PARP degradation in HL-60 cells.

FIG. 20: COH-SR4 and COH-SR9 inhibited growth and proliferation of MCF-7 and MDA-MB-231 breast cancer cells.

FIG. 29: Effects of COH-SR3, COH-SR4, COH-SR9, COH-SR14, doxorubicin, paclitaxel or cisplatin on viabilities of 4T1 breast cancer cells (A) concentrations of test compounds are 2 μM or higher; (B) concentrations of test compounds are 1 μM or lower (uM also represents μM in the figure).

FIG. 32: Effects of 20 μM COH-SR4, COH-SR9, COH-SR14, doxorubicin, paclitaxel or cisplatin on viabilities of CD44+CD24− cancer stem cells and CD44−/EpCAM+ regular breast cancer cells (A) metastized in the brain, and (B) in breast tumor.

FIG. 33: Effects of COH-SR4 in ovarian cancer cells: (A) Effects of COH—SR4 on SKOV3, MADH 2744 and A2780 DPPr cells; and (B) Inhibition of COH-SR4 in phosphorylation of Stat3 protein and HIF-1α protein expression in SKOV3 cells.

FIG. 35: Higher doses of COH-SR4 showed faster killing in glioma cells (A) U251 and (B) PBT-017 (uM also represents μM in the figures).

FIG. 37: COH-SR4 induced apoptosis of glioma cells. (A) Absolute cell numbers of PBT-017 glioma cells decreased after four day of incubation with COH-SR4; and (B) fractions of apoptotic cells of PBT-017 glioma cells increased after four day of incubation with COH-SR4 (uM also represents μM in the figures).

means p<0.05, "" means p<0.01, and "*" means p<0.001 regarding the significant differences).

FIG. 39: (A) Effects of COH-SR4 on CD133 sorted glioma cell PBT-017; and (B) Effects of COH-SR4 on amounts of PI+ cells in pNHA and glioma cell U251 (uM also represents μM in the figures, "NS" means no statistically significant difference was observed; "" means p<0.01, and "*" means p<0.001 regarding the significant differences).

Figure 40:
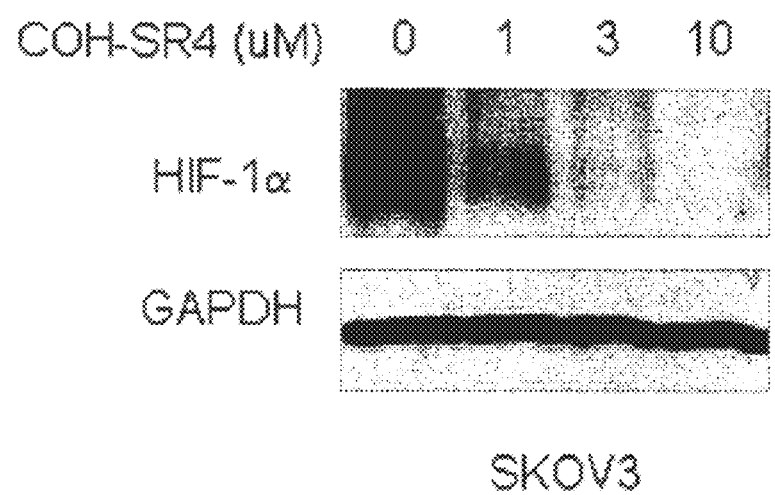

FIG. 40: COH-SR4 inhibited HIF-1α protein expression in U251 cells (uM also represents μM in the figure).

Figure 41:
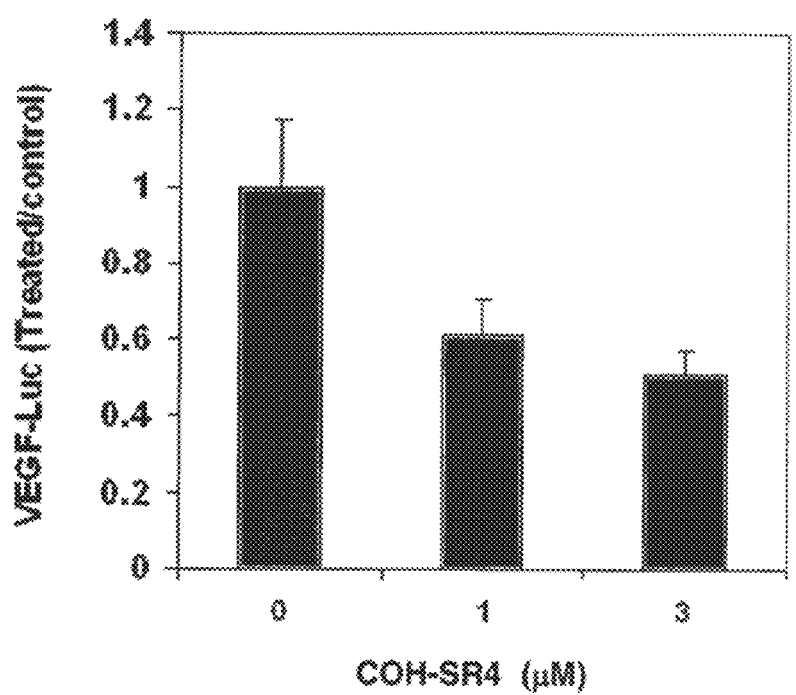

FIG. 41: COH-SR4 inhibited luciferase expression of VEGF protein in U251 cells.

Figure 42:
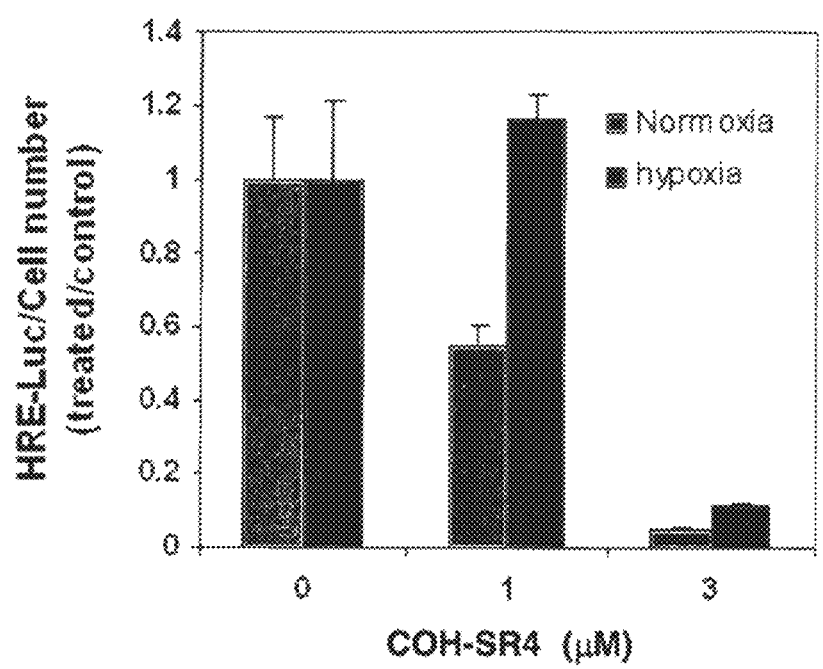

FIG. 42: COH-SR4 inhibited luciferase expression driven by HRE promoter in U251 cells under both normoxic and hypoxic conditions.

FIG. 43: Effects of COH-SR4 and TMZ on glioma cells (A) PBT-017 and (B) U251.

FIG. 44: COH-SR4 showed synergism with TMZ in treating glioma cells (A) U251 and (B) PBT-017.

FIG. 45: COH-SR4 showed synergism with 7-ethyl-10-hydroxy-camptothecin (SN-38, an active metabolite of CPT-11) in treating glioma cells (A) U251 and (B) PBT-017.

Figure 46:
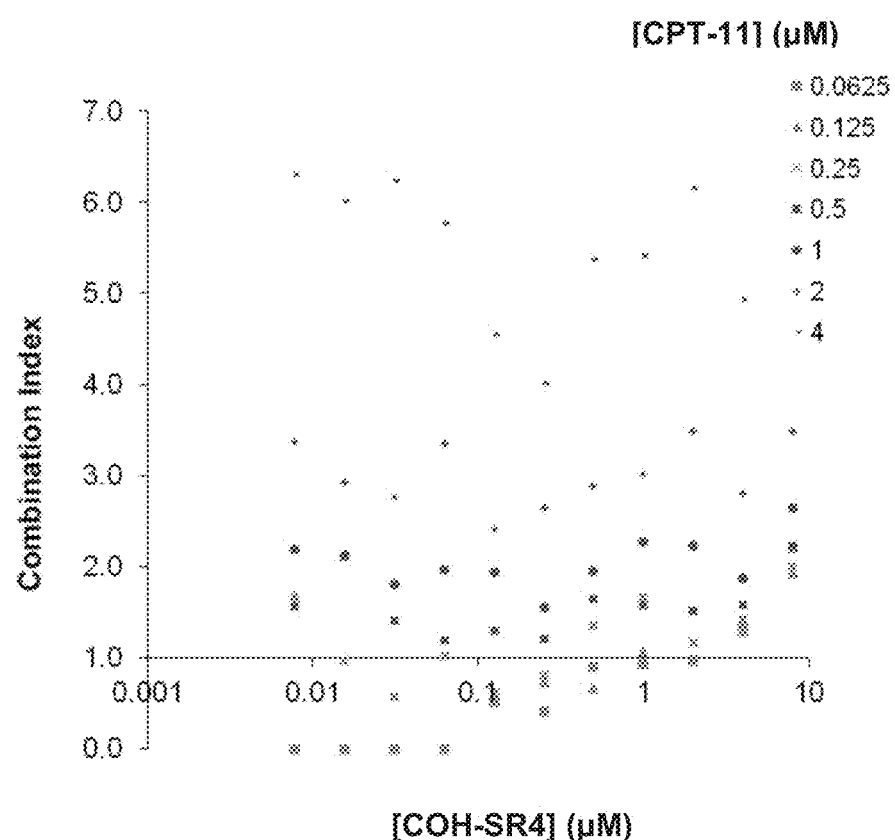

FIG. 46: COH-SR4 showed synergism with irinotecan (CPT-11) in treating glioma cells U251.

Figure 47:
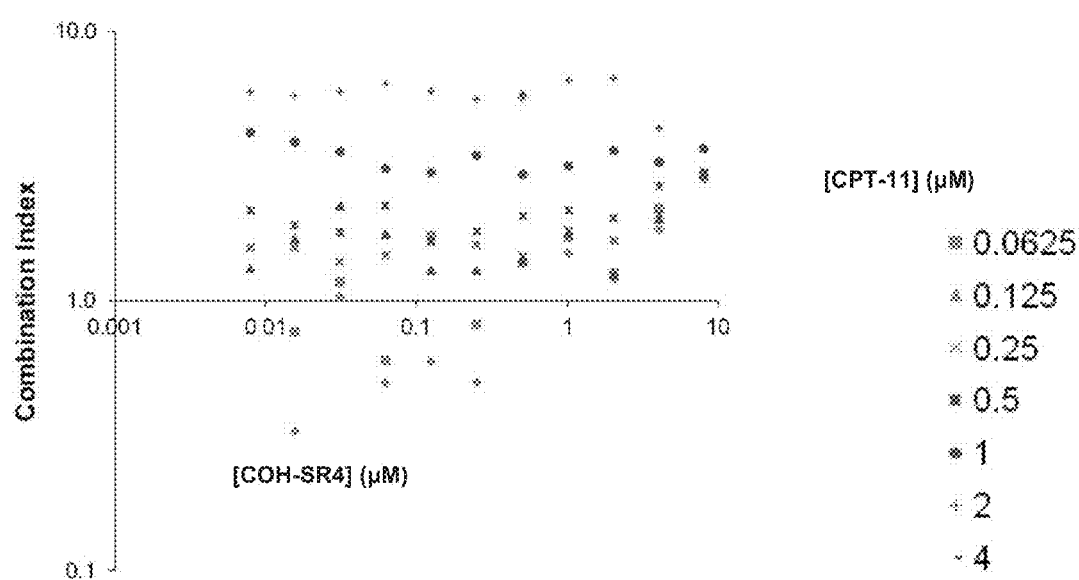

FIG. 47: COH-SR4 showed synergism with irinotecan (CPT-11) in treating glioma cells PBT-017.

Figure 48:
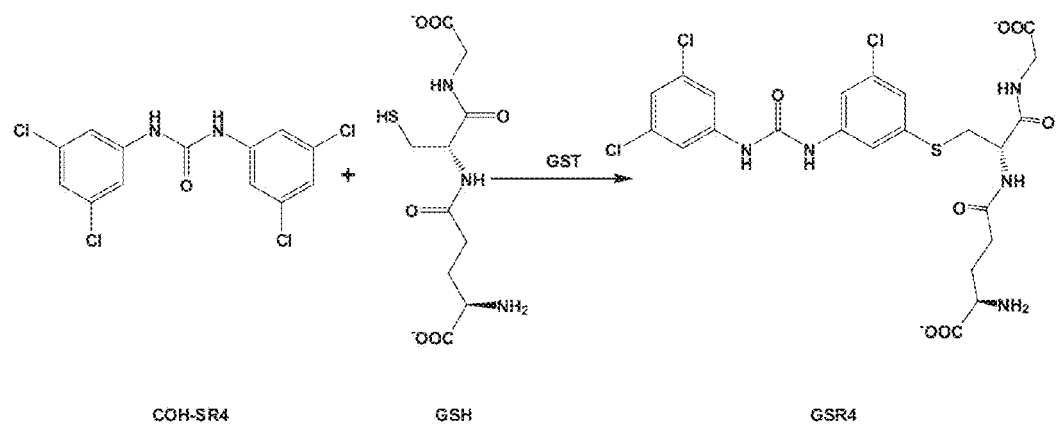

FIG. 48: Formation of COH-SR4 and Glutathione (GSH) conjugate mono-glutationyl-SR4 (GSR4) in the presence of GST-P of the glutathione S-transferase family (GSTs).

Figure 49:
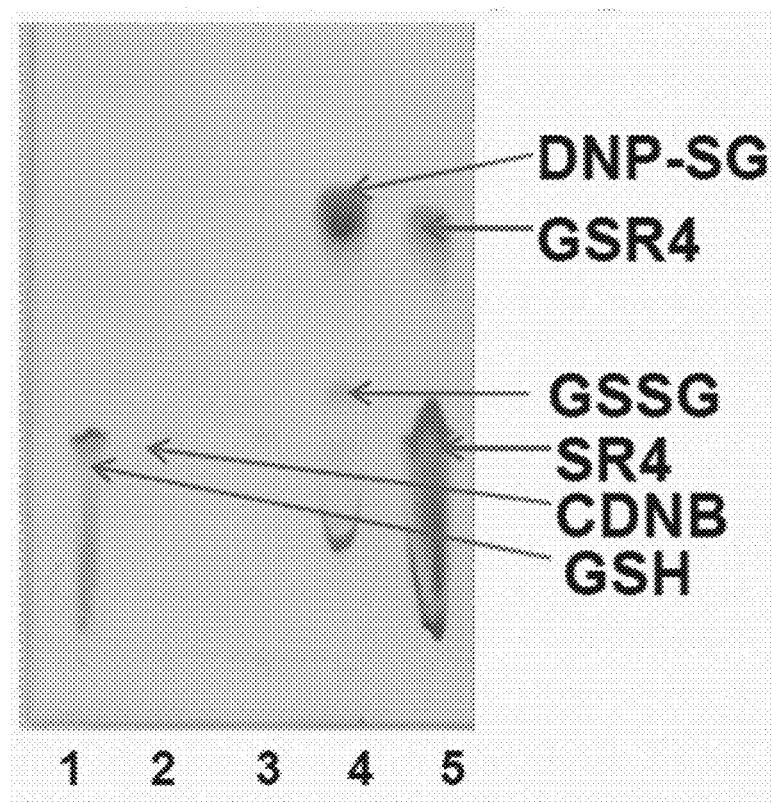

FIG. 49: TLC plate showing the formation of GSR4.

Figure 50:
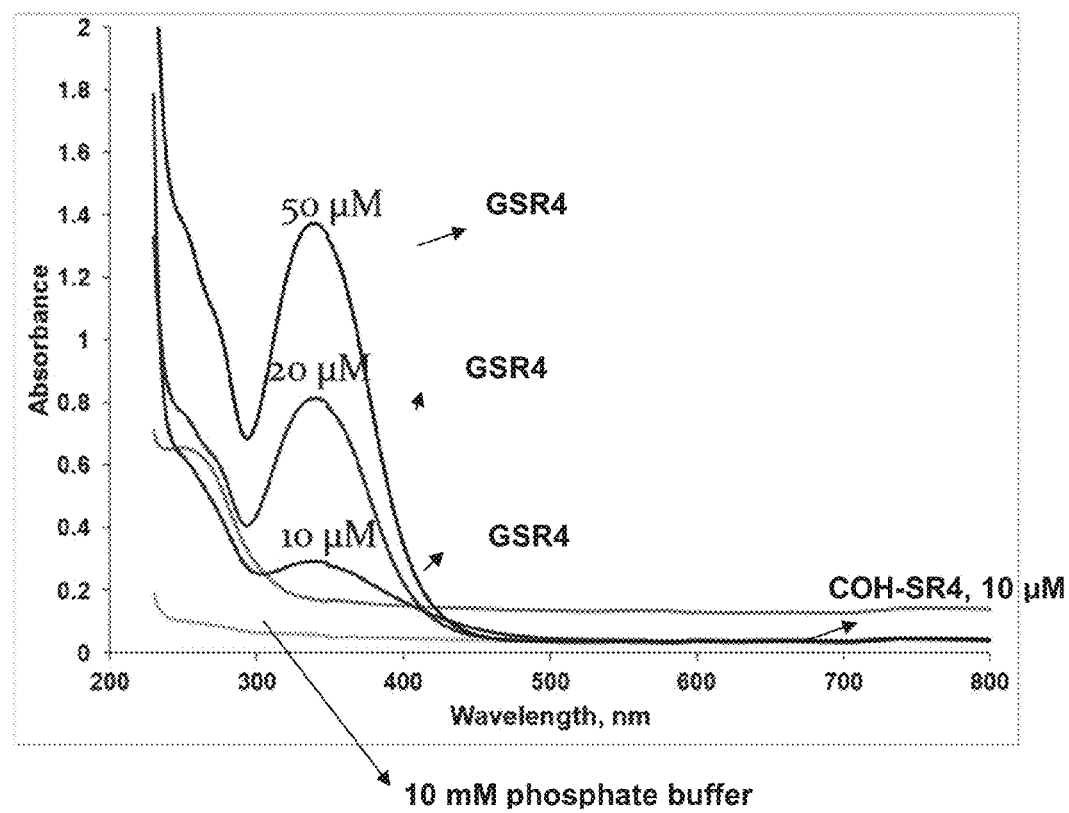

FIG. 50: Visible absorption spectrum of GSR4 and COH-SR4.

Figure 51:
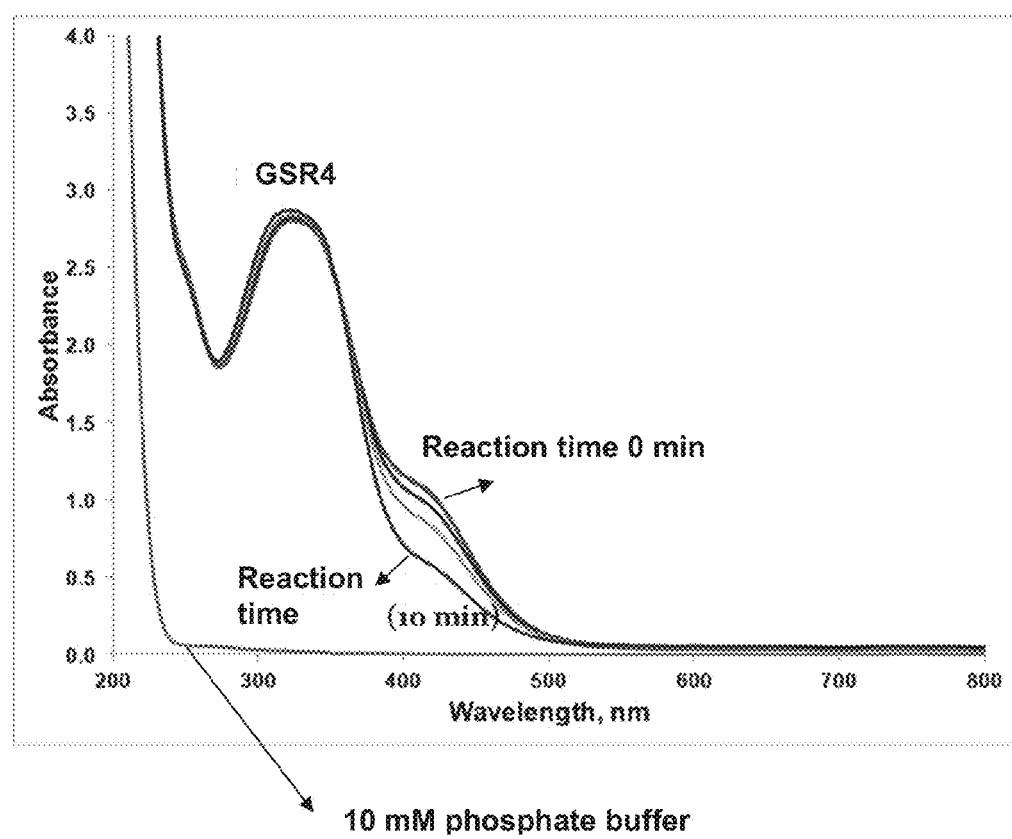

FIG. 51: Visible absorption spectrum showing formation of GSR4.

Figure 52:
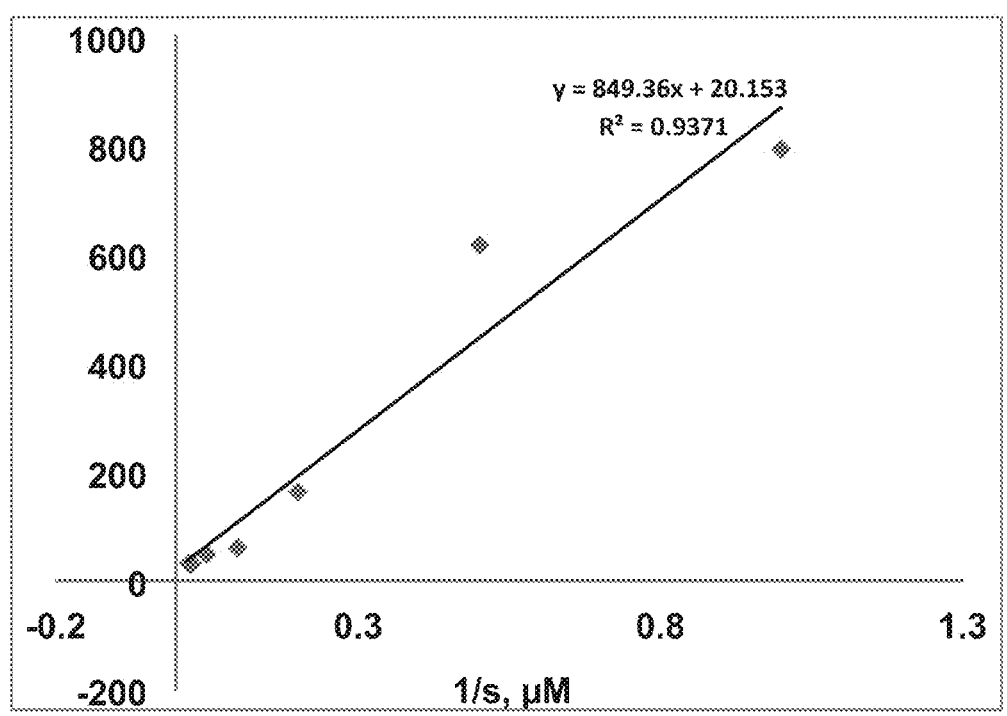

FIG. 52: Kinetics of GST-P using COH-SR4 as a substrate.

Figure 53:
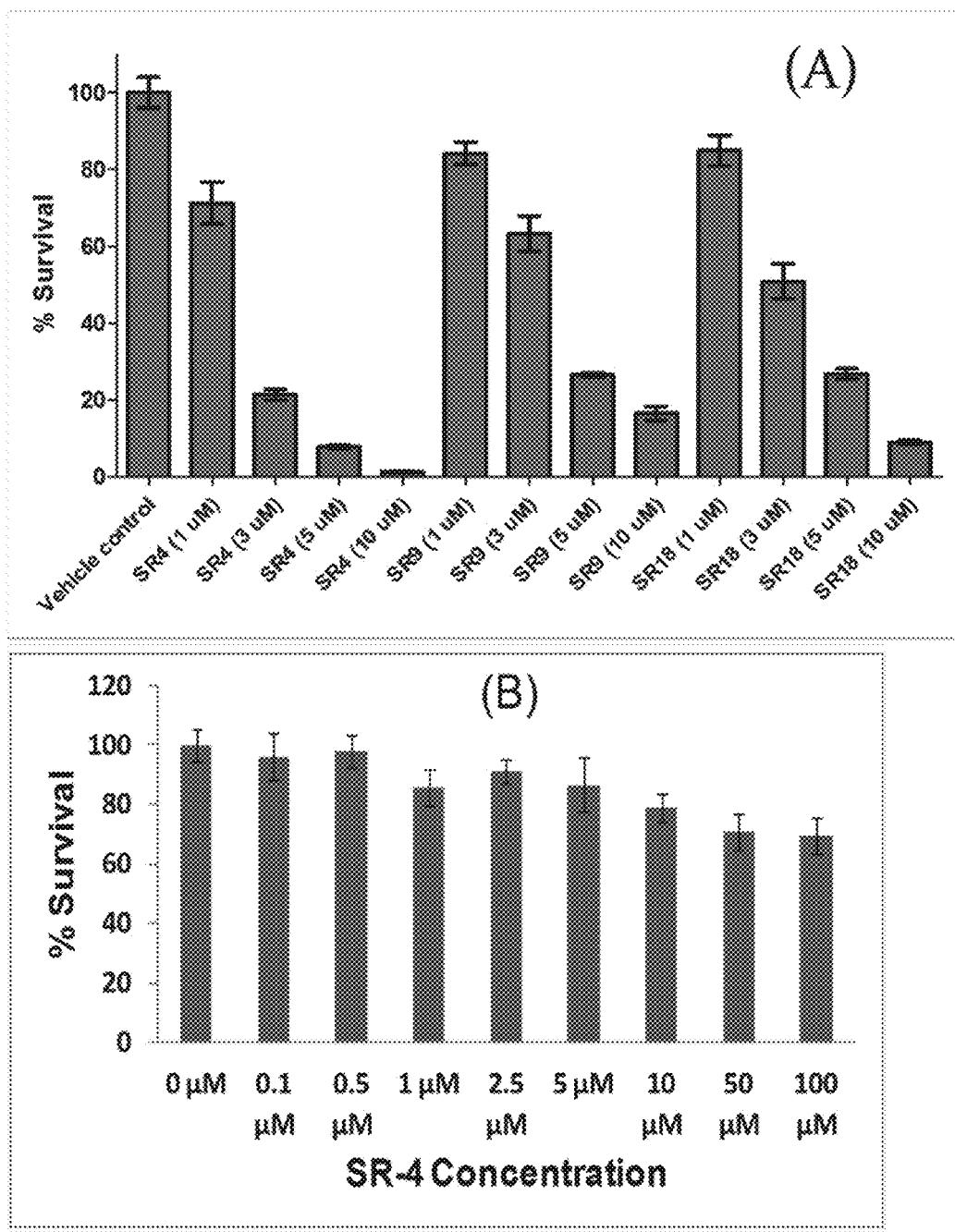

FIG. 53: (A) Effect of COH-SR4, COH-SR9 and COH-SR18 on B16F10 cells and (B) Effect of COH-SR4 on HUVEC cells.

FIG. 54: Effect of COH-SR4 on B16-F0 cells and Hs600T cells after 48-hour treatment. (A) dose-dependent effect of COH-SR4 on cell viabilities; and (B) IC$_{50}$ of COH-SR4.

FIG. 55: Effect of COH-SR4 on B16-F0 cells and Hs600T cells after 96-hour treatment. (A) dose-dependent effect of COH-SR4 on cell viabilities; and (B) IC$_{50}$ of COH-SR4.

FIG. 56: Effect of COH-SR4 on apoptosis as determined by TUNEL assay in B16-F0 cells and Hs600T cells after 48-hour treatment, apoptotic cells showed green fluorescence, the pictures shown in the top panels were obtained from one sample, and the pictures shown in the bottom panels were obtained from another sample.

Figure 57:
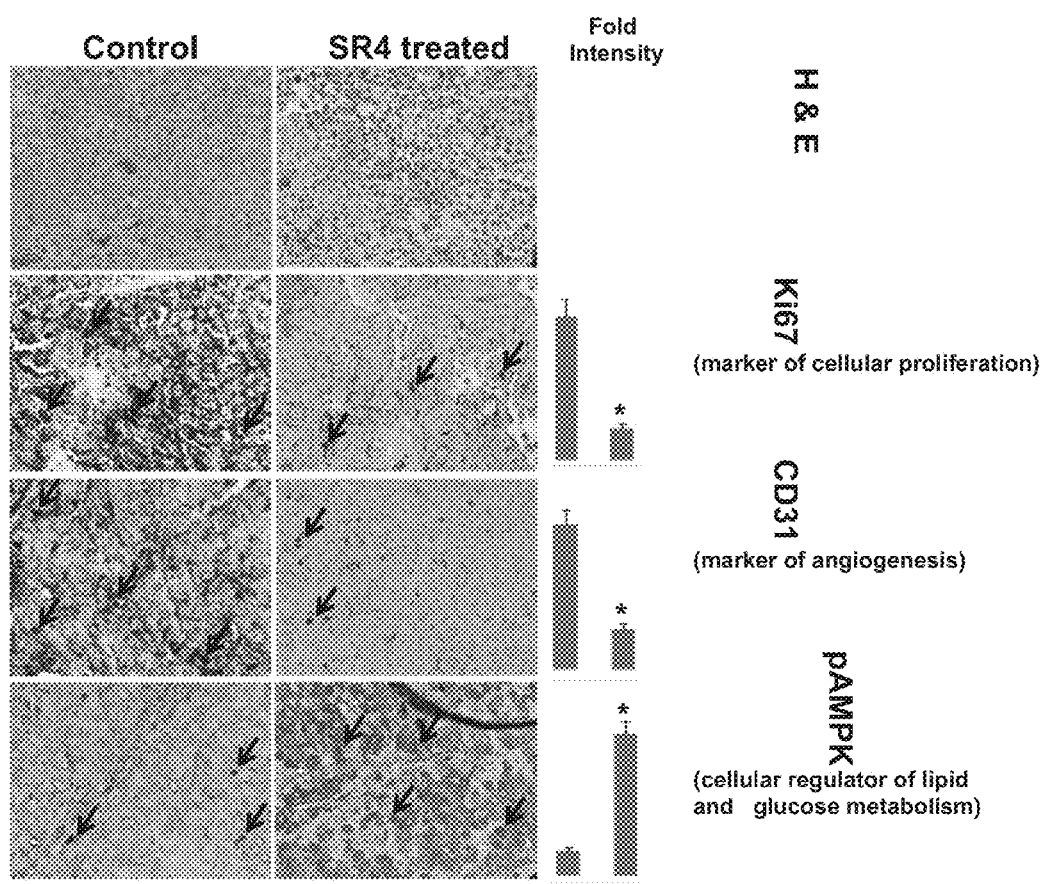

FIG. 57: Histopathologic analyses of effects of COH-SR4 in B16 mouse melanoma tumor section.

Figure 58:
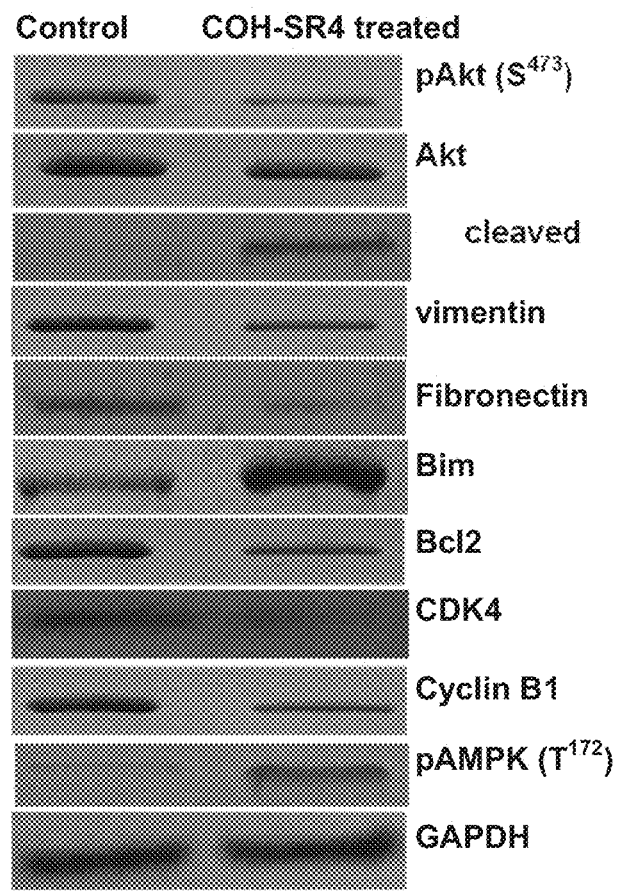

FIG. 58: Western-blot analyses of signaling proteins showing effects of COH-SR4 in B16 mouse melanoma tumor tissue lysates.

FIG. 59: Effects of oral administrations of COH-SR4 in in vivo Syngeneic mouse model based on (A) changes of mice weight; and (B) changes of tumor cross-sectional area.

Figure 60:
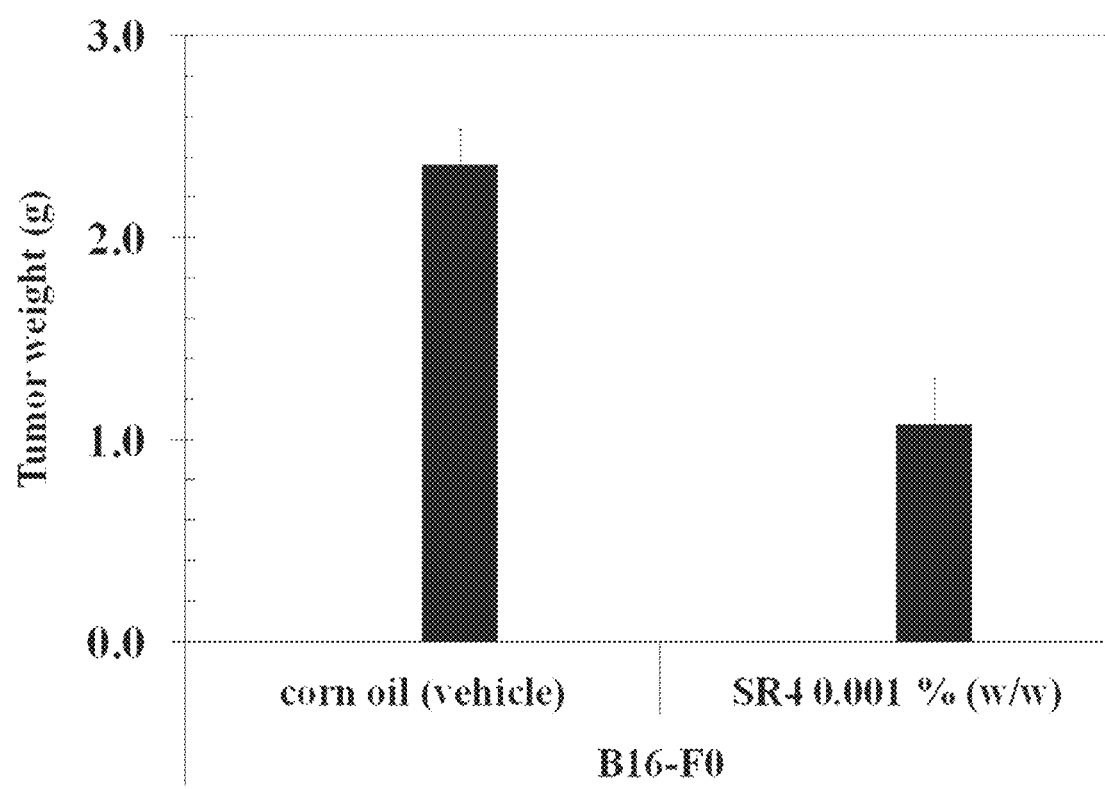

FIG. 60: Effects of oral administrations of COH-SR4 in in vivo Syngeneic mouse model based on changes of tumor weight.

Figure 61:
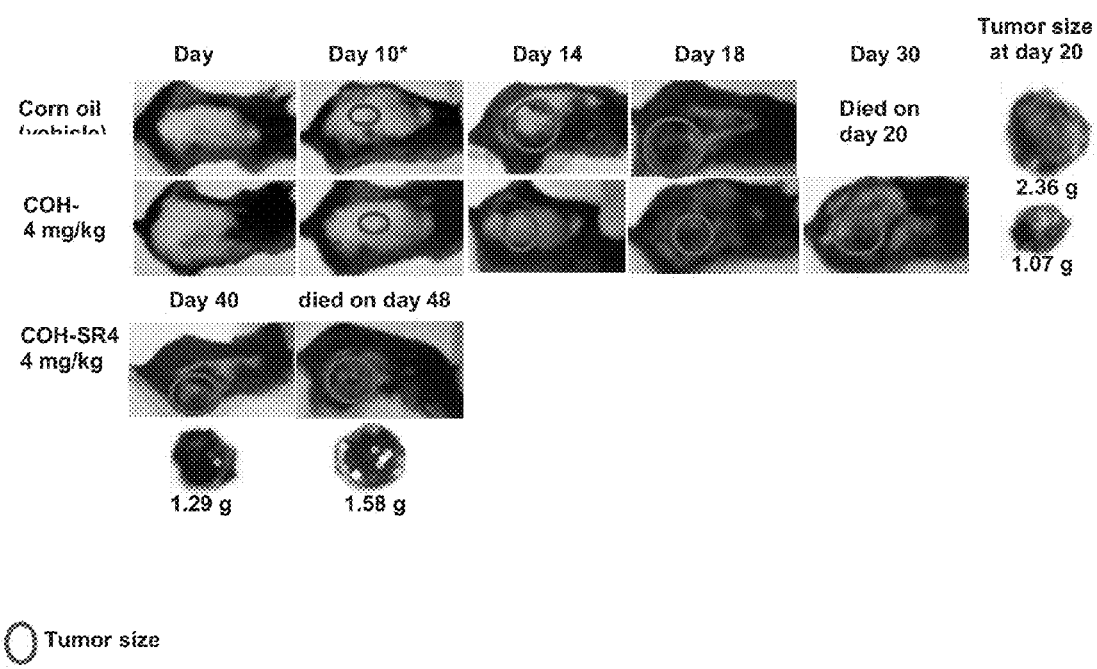

FIG. 61: Effects of oral administrations of COH-SR4 in in vivo Syngeneic mouse model.

Figure 62:
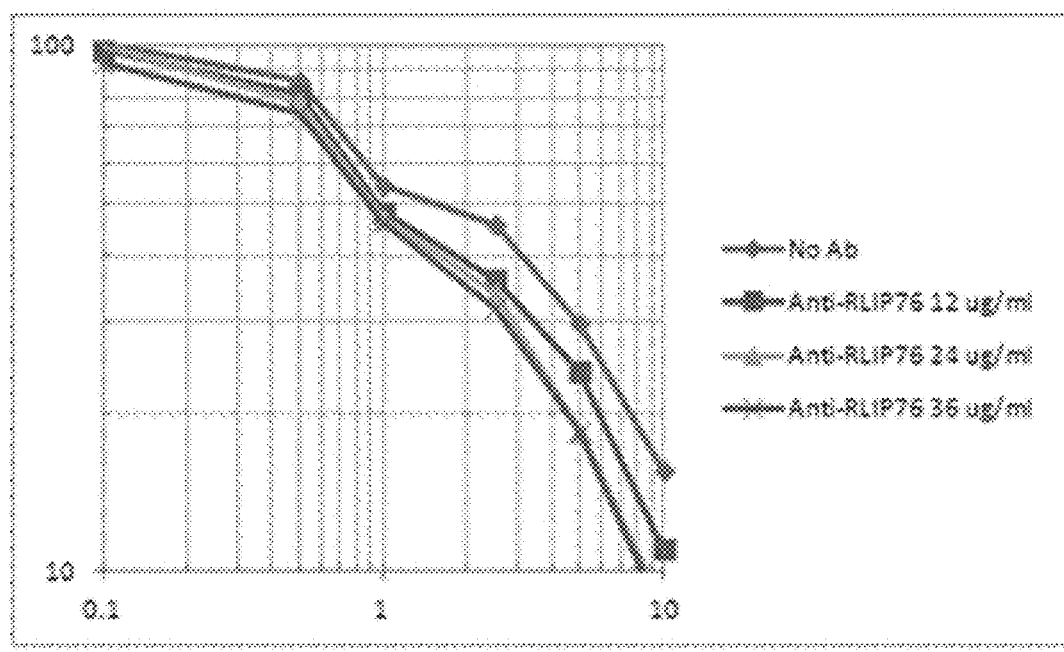

FIG. 62: Potentiating COH-SR4 cytotoxicity in B16F10 cells by anti-RLIP76 polyclonal antibodies (uM also represents μM in the figure).

DETAILED DESCRIPTION

Figure 1:
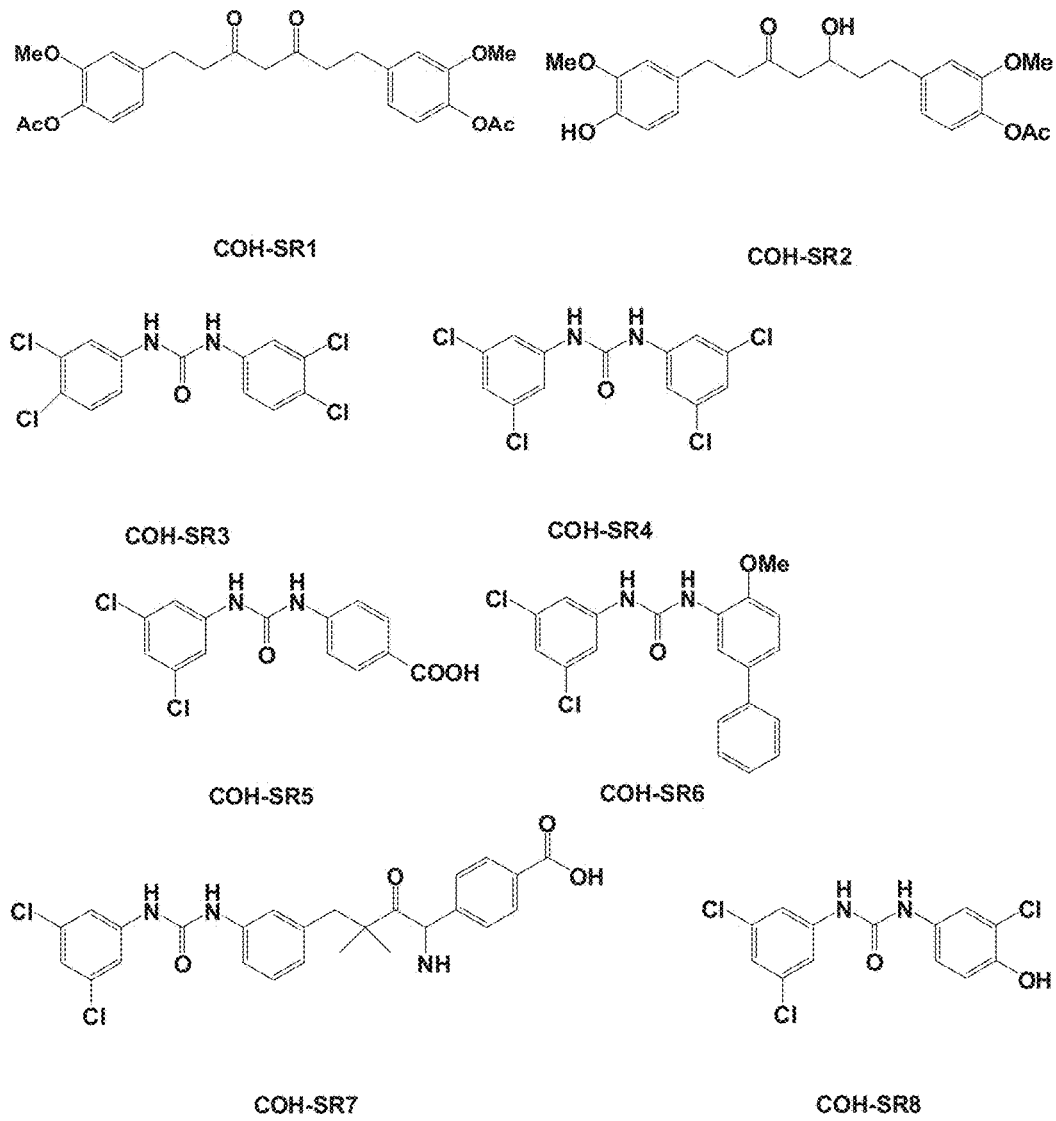
FIG. 1: Chemical structures of COH-SR1, COH-SR2, COH-SR3, COH-SR4, COH-SR5, COH-SR6, COH-SR7 and COH-SR8.

One aspect of the present disclosure relates to derivatives of aryl and heterocyclic ureido aryl and heterocyclic carboxamido isobutyric acids, dichlorophenyl urea, curcumin, and 1,3-diazetidine-2,4-dione (FIGS. 1~3).

Examples of the derivatives of aryl and heterocyclic ureido aryl and heterocyclic carboxamido isobutyric acids include, without limitation, COH-SR7 [4-[(3,5-dichlorophenylureido)phenoxyisobutyril]-4-aminobenzoic acid](also referred to as LR-99, LR99 or SR7), LR23 [4-(3,5-dichlorophenylureido)phenoxyisobutyryl-I-amidocyclohexane-Icarboxylic acid](also referred to as LR-23), and LR59 [1-(4-chlorobenzyl)-3-dichlorophenyeureido)-4-phenoxy-isobutyric acid](also referred to as LR-59) (FIGS. 1 and 2).

Examples of the derivatives of dichlorophenyl urea include, without limitation, COH-SR3 [1,3-bis(3,4-dichlorophenyl)urea](also referred to as SR3), COH-SR4 [1,3-bis(3,5-dichlorophenyl)urea](also referred to as SR4), COH-SR5 [1-(3,5-dichlorophenyl)-3-(4-carboxyphenyl)urea](also referred to as SR5), COH-SR6 [1-(3,5-dichlorophenyl)-3-(4-methoxy-[1,1'-bisphenyl]-3-yl)urea](also referred to as SR6), COH-SR7, COH-SR8 [1-(3,5-dichlorophenyl)-3-(3-chloro-4-hydroxyphenyl)urea](also referred to as SR8), COH-SR9 [1-(3,5-dichlorophenyl)-3-(3,5-dichloro-2-hydroxy-4-methylphenyl)urea](also referred to as SR9), COH-SR10 [1-(3,5-dichlorophenyl)-3-(3,5-dichloro-2-hydroxyphenyl)urea](also referred to as SR10), COH-SR12 [1-(3,5-dichlorophenyl)-3-(3,4,5-trichlorophenyl)urea](also referred to as SR12), COH-SR13 [1,3-bis(3,4,5-trichlorophenyl)-3-(2,3,5-trichlorophenyl)urea](also referred to as SR13), COH-SR14 [1-(3,5-dichloro-4-methylphenyl)-3-(3,5-dichlorophenyl)urea](also referred to as SR14), COH-SR16 [1-(2,6-dichloropyridin-4-yl)-3-(3,5-dichlorophenyl)urea](also referred to as SR16), and COH-SR18 [1-(2-chloropyrimidin-4-yl)-3-(3,5-dichlorophenyl)urea](also referred to as SR18) (FIGS. 1 and 2).

Examples of curcumin derivatives include, without limitation, COH-SR1 [1,7-bis(4'-acetoxy-3'-methoxyphenyl)-3,5-heptadione](also referred to as SR1) and COH-SR2 [(1E, 4Z,6E)-7-(4"-acetoxy-3"-methoxyphenyl)-5-hydroxy-1-(4'-hydroxy-3'-methoxyphenyl)hepta-1,4,6-trien-3-one](also referred to as SR2) (FIG. 1).

Examples of 1,3-diazetidine-2,4-dione derivatives include, without limitation, COH-SR11 [1,3-bis(3,5-dichloro-2-hydroxyphenyl) 1,3-diazetidine-2,4-dione](also referred to as SR11) (FIG. 2).

As used herein, the COH-SR compound(s) refer to one or more compounds selected from the group consisting of COH-SR1, COH-SR2, COH-SR3, COH-SR4, COH-SR5, COH-SR6, COH-SR7, COH-SR8, COH-SR9, COH-SR10, COH-SR11, COH-SR12, COH-SR13, COH-SR14, COH-SR16, COH-SR18, LR23, LR59, and the pharmaceutically acceptable derivative, solvates, salts and stereoisomers thereof, including mixtures thereof in all ratios.

In one embodiment, the COH-SR compounds modulate differentiation in adipocytes and cancer cells. The preferred COH-SR compounds are COH-SR1, COH-SR2, COH-SR3, COH-SR4, COH-SR6, COH-SR7, COH-SR9, COH-SR14, COH-SR16, COH-SR18, LR23, LR59, and the pharmaceutically acceptable derivative, solvates, salts and stereoisomers thereof, including mixtures thereof in all ratios.

In certain embodiments, under conditions that normally promote differentiation of preadipocytes to adipocytes, the COH-SR compounds (1) inhibit differentiation and accumulation of lipid droplets in preadipocytes and (2) reduce intracellular triglyceride contents. The COH-SR compounds show similar effects to preadipocytes compared to certain known HDAC inhibitors (e.g. TSA and apicidin) and fatty acid synthase inhibitor (e.g. C75).

In certain embodiments, the COH-SR compounds inhibit the earlier stage of the adpogenic process (preadipocyte proliferation) in preadipocytes.

In certain embodiments, the COH-SR compounds induce dedifferentiation of fully differentiated adipocytes.

In certain embodiments, the COH-SR compounds are cytotoxic to cancer cells including cancer stem cells. Examples of the cancer treated include, without limitation, leukemia (e.g. acute myeloid leukemia (AML) and monocytic leukemia), lung cancer (e.g. non-small cell lung cancer), colon cancer, CNS cancer, melanoma, ovarian cancer, renal cancer, prostate cancer, breast cancer, and brain cancer (e.g. glioma, glioblastoma multiforme (GBM)). Examples of cancer cells include, without limitation, leukemia cell (e.g. THP1, CCRF-CEM, HL-60, HL-60(TB), K-562, MOLT-4, RPMI-8226, SR, and R937); non-small cell lung cancer (e.g. A-549, A549/ATCC, EKVX, HOP-62, HOP-92, NCI-H226, NCI-H23, NCI-H322M, NCI-H460, and NCI-H522); colon cancer (e.g. COLO 205, HCT-116, HCT-15, HT29, KM12, and SW-620); CNS cancer (e.g. SF-268, SF-295, SF-539, SNB-19, SNB-75, and U251); melanoma (e.g. LOX IMVI, MALME-3M, M14, MDA-MB-435, SK-MEL-2, SK-MEL-28, SK-MEL-5, UACC-257, UACC-62, B16F10, and B16-F0); ovarian cancer (e.g. Hela, IGROV1, OVCAR-3, OVCAR-4, OVCAR-5, OVCAR-8, NCI/ADR-RES, MADH2744, A2780 DPPr and SKOV-3); renal cancer (e.g. 786-0, A498, ACHN, CAKI-1, RXF 393, SN12C, TK-10, and UO-31); prostate cancer (PC-3 and DU-145); breast cancer (e.g. 4T1, HMLE, MDA-MB-231, MDA-MB-231/ATCC, HS 578T, 8T-549, T-47D, MDA-MB-468, and MCF7, and breast tumor cancer stem cells (e.g. CD44+/CD24− breast cancer cells)), and brain cancer (e.g. glioma cells such as U251, U87, PBT-017, PBT018, PBT003 and PBT028).

In certain embodiments, the COH-SR compounds prevent cellular proliferation and arrest growth via G0/G1 arrest. Cyclins (e.g. cyclin D1 and E2) and cyclin dependent kinases (CDKs, e.g. CDK2 and CDK4) play critical roles in promoting G1 phase progression. The COH-SR compounds modulate various cyclin-dependent kinases (CDKs), and/or induction of p21 and p27 in cancer cells and preadipocytes. A preferred cancer is leukemia and melanoma. The preferred COH-SR compounds are COH-SR4 and COH-SR9, and the pharmaceutically acceptable derivative, solvates, salts and stereoisomers thereof, including mixtures thereof in all ratios.

In certain embodiments, the COH-SR compounds activate AMP-activated protein kinase (AMPK) in cancer cells and adipocytes. The preferred cancers are ovarian cancer and leukemia. The preferred COH-SR compounds are COH-SR4, COH-SR9, COH-SR16 and COH-SR18, and the pharmaceutically acceptable derivative, solvates, salts and stereoisomers thereof, including mixtures thereof in all ratios. The more preferred COH-SR compound is COH-SR4, and the pharmaceutically acceptable derivative, solvates, salts and stereoisomers thereof, including mixtures thereof in all ratios.

AMPK is an energy-sensing serine/threonine kinase present in all eukaryotes that is activated by metabolic stresses that either inhibit ATP synthesis or accelerate ATP consumption. Phosphorylated activation of AMPK in response to an increase in the cellular AMP:ATP ratio increases glucose uptake, fatty acid oxidation, and mitochondrial biogenesis, and decreases synthesis of fatty acids, sterols, glycogen and proteins. Without being bound by a specific mechanism, such alterations in lipid and glucose metabolism would be expected to ameliorate the pathogenesis of obesity, type 2 diabetes and other metabolic disorders. AMPK has also been identified as a potential target for cancer prevention and/or treatment. Cell growth and proliferation are energetically demanding, and AMPK may act as an "energy checkpoint" that permits growth and proliferation only when energy reserves are sufficient. Thus, activators of AMPK such as the COH-SR compounds are therapeutic for metabolic disorders (e.g. diabetes and obesity) and for cancers.

In certain embodiments, the COH-SR compounds induce apoptosis in cancer cells. The preferred cancer is leukemia, brain cancer and melanoma. The preferred COH-SR compounds are COH-SR4 and COH-SR9, and the pharmaceutically acceptable derivative, solvates, salts and stereoisomers thereof, including mixtures thereof in all ratios.

In certain embodiments, the COH-SR compounds are substrates of glutathione S-transferases (GSTs). A conjugate of GSH and a COH-SR compound is formed in the presence of GST, and the conjugate is a product-inhibitor of GSTs.

GSTs are a multi gene family of isoenzymes ubiquitously expressed in most living organisms. These enzymes catalyze the conjugation of glutathione (GSH) to a variety of electrophilic compounds, thus establishing the now widely accepted role of GSTs as cell housekeepers involved in the detoxification of endogenous as well as exogenous substances. The GSTs comprises of three major class of proteins: cytosolic, mitochondrial and microsomal referred to as membrane-associated proteins of which the cytosolic GSTs (class A (alpha), M (mu), P (pi), T (theta), S (sigma), O (Omega) and Z (zeta) constitute the largest family.

Without being bound by a specific mechanism, it is proposed that GSTs could confer drug-resistance to alkylating agents as well as oxidants. The high over-expression of GSTs in many cancer tissues, particularly melanoma, along with the ability of GSTs to activate MAPK in the presence of glutathione-conjugates indicate a critical role of GSTs in providing cancer cells resistance to apoptosis caused by electrophilic toxins during anti-cancer therapy. Therefore, targeting GSTs may be an effective strategy to design the drugs for treatment for malignant melanoma.

The majority of human tumor cell lines, including those selected in vitro for resistance to chemotherapeutic agents, over-express GSTP-1-1, referred herein as GST-P or GSTP. GSTP is the predominant isoenzyme (up to 2.7% of the total cytosolic protein) in all but 2 of 60 tumor cell lines used in the Drug Screening Program of the National Cancer Institute (NCI). Significant quantitative correlations among enzymatic activity, total enzyme protein, and mRNA were shown, particularly in those cell lines selected for resistance to alkylating agents such as melphalan, chlorambucil, cyclophosphamide, BCNU (N,N-bis(2-chloroethyl)-N-nitrosourea), and cisplatin. A variety of human cancers (e.g. breast, colon, kidney, lung and ovarian cancer) usually express high levels of GSTP1-1 compared with the surrounding tissues. Without being bound by a specific mechanism, GSTP1-1 expression may be a marker for cancer development. High expression levels may be associated not only with disease progression but also with drug resistance in patients undergoing chemotherapy. GSTs are known to be overexpressed in malignant tumors suggesting that they may play a role in acquired resistance to anticancer agents.

In certain embodiments, the COH-SR compounds are substrates for GSTP. A conjugate of GSH and a COH-SR compound is product-inhibitor of GSTPs. Therefore, the co-administration of a COH-SR compound as an adjuvant therapy for chemotherapy may restore drug sensitivity of resistant cancer cells.

In certain embodiments, the COH-SR compounds show no or low cytotoxicity to normal cells. COH-SR compounds have little effect on the viability of HUVECs. In certain embodiments, up to 10 μM COH-SR compounds have little effect on the viability of HUVECs.

Another aspect of the present disclosure relates to a pharmaceutical composition comprising a therapeutically effective amount of a COH-SR compound and a pharmaceutically acceptable carrier.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Pharmaceutically acceptable carrier is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., the COH-SR compounds or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Examples of materials which can serve as pharmaceutically-acceptable carriers include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of an active ingredient in these formulations can vary widely, and will be selected primarily based on fluid volumes, viscosities, body weight and the like in accordance with the particular mode of administration selected and the biological subject's needs. For example, the concentration can be 0.0001% to 100%, 0.001% to 50%, 0.01% to 30%, 0.1% to 20%, 1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges and for transdermal administration include solution, suspension and gel.

In another embodiment, the composition disclosed herein further comprises a second therapeutic agent. In certain embodiments, the second therapeutic agent is another COH-SR compound or a known anticancer drug. Examples of the known anticancer drugs include, without limitation, chemotherapy drugs (e.g. TMZ, SN38, CPT-11, and 5-FU).

In the methods disclosed below, optimal dosages to be administered to a subject may be determined by those skilled in the art, and will vary with the particular compound in use, the strength of the preparation, the mode of administration, and the advancement of the condition treated. Additional factors depending on the particular subject being treated, including subject age, weight, gender, diet and time of administration, will result in a need to adjust dosages. Administration of the pharmaceutical composition may be effected continuously or intermittently. In any treatment regimen, the composition may be administered to a subject either singly or in a cocktail containing a COH-SR compound and other therapeutic agent (e.g. another COH-SR compound and/or other anti-cancer drugs). In certain embodiments, an appropriate dosage level will generally be about 0.001 to 50 mg per kg subject body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

The exact dosage will be determined in light of factors related to the subject. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the therapeutic agents in the pharmaceutical composition (e.g. a COH-SR compound) used. Typically, a pharmaceutical composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

Another aspect of the present disclosure relates to a method of treating or preventing obesity in a subject comprising administrating a pharmaceutical composition disclosed supra to the subject. The pharmaceutical composition comprises a COH-SR compound selected from the group consisting of COH-SR1, COH-SR2, COH-SR3, COH-SR4, COH-SR5, COH-SR6, COH-SR7, COH-SR8, COH-SR9, COH-SR10, COH-SR12, COH-SR13, COH-SR14, COH-SR16, COH-SR18, LR23 and LR59, and preferably from the group consisting of COH-SR1, COH-SR2, COH-SR3, COH-SR4, COH-SR6, COH-SR7, LR23 and LR59.

In one embodiment, the treatment/prevention of obesity includes, without limitation, reducing fat mass and lowering bodyweights.

In another embodiment, the method further comprises administering to the subject a pharmaceutical composition disclosed herein to (1) inhibit differentiation and/or accumulation of lipid droplets and/or (2) to reduce intracellular triglyceride contents and/or (3) inhibit proliferation in preadipocyte cells of the subject.

In another embodiment, the method further comprises administering to the subject a pharmaceutical composition disclosed herein to induce dedifferentiation of fully differentiated adipocytes in the subject.

In another embodiment, the method further comprises administering to the subject a pharmaceutical composition disclosed herein to activate AMPK in preadipocyte cells of the subject.

Another aspect of the present disclosure relates to a method of treating a cancer in a subject comprising administering a pharmaceutical composition disclosed herein to the subject. The pharmaceutical composition comprises a COH-SR compound selected from the group consisting of COH-SR1, COH-SR2, COH-SR3, COH-SR4, COH-SR5, COH-SR6, COH-SR7, COH-SR8, COH-SR9, COH-SR10, COH-SR12, COH-SR13, COH-SR14, COH-SR16, COH-SR18, LR23 and LR59, preferably from the group consisting of COH-SR2, COH-SR3, COH-SR4, COH-SR6, COH-SR7, COH-SR9, COH-SR14, COH-SR16, and COH-SR18, and more preferably COH-SR4 and COH-SR9.

Examples of the cancer treated include, without limitation, leukemia (e.g. acute myeloid leukemia (AML) and monocytic leukemia), lung cancer (e.g. non-small cell lung cancer), colon cancer, CNS cancer, melanoma, ovarian cancer, renal cancer, prostate cancer, breast cancer, and brain cancer (e.g. glioma and GBM).

In one embodiment, the method further comprises administering to the subject a pharmaceutical composition disclosed herein to (1) modulate differentiation and/or (2) promote cell cycle arrest and/or apoptosis in the cancer cells in the subject.

In another embodiment, the method further comprises administering to the subject a pharmaceutical composition disclosed herein to activate AMPK in the cancer cells of the subject.

In another embodiment, the method further comprises administering to the subject a pharmaceutical composition disclosed herein to inhibit a GST, preferably GSTP, in the cancer cells of the subject.

In another embodiment, the cancer treated in the method described herein is a malignant and/or resistant cancer, examples include, without limitation, chemotherapy resistant ovarian cancer (e.g. cisplatin resistant ovarian cancer), TMZ resistant GBM, and malignant melanoma.

In another embodiment, the pharmaceutical composition administered in the method further comprising a second therapeutic agent, which is a second COH-SR compound or an anticancer drug that is not a COH-SR compound. In certain embodiments, the combination of a COH-SR compound and a second therapeutic agent can show synergistic or additive effects in the treatment. The optimal dosages of each ingredient in the pharmaceutical composition can be determined as described supra.

Examples of the anticancer drugs that are not the COH-SR compounds include, without limitation, chemotherapeutics such as TMZ, SN38, CPT-11, or 5-FU. In certain embodiments, the pharmaceutical composition comprising COH-SR4 and a second therapeutic agent selected from the group consisting of TMZ, SN38, CPT-11, and 5-FU. In certain embodiments, the combination of COH-SR4 and a chemotherapeutic can show synergistic or additive effect in treating cancer. The optimal dosage of each composition can be determined as described supra. Low dosages of COH-SR4 and a chemotherapeutic show a synergistic effect to cancer cells. Thus, low dosage of COH-SR compound can improve the therapeutic effects of the chemotherapeutics.

Certain cancers, (e.g. GBMs) can repair TMZ-induced damages and therefore develop resistance to TMZ. Thus there is a need to potentiate therapeutic effects of TMZ. Without being bound by a specific mechanism, TMZ may generate intracellular reactive oxygen species (ROS) in cancer cells, which in turn caused apoptosis of the cancer cells. In certain embodiments, treatment of COH-SR4 or a pharmaceutical composition thereof increase ROS in cancer cells (e.g. glioma cells). In certain embodiments, COH-SR4 or a pharmaceutical composition thereof shows more potent cytotoxicity to cancer cells (e.g. glioma cells) than certain known chemotherapy drugs such as TMZ, 5-FU, and CPT-11.

In another embodiment, the method comprises administering to the subject a first pharmaceutical composition comprising a first COH-SR compound, and administering to the subject a second pharmaceutical composition comprising a second therapeutic agent, wherein the two pharmaceutical compositions are administered at the same time or separate times.

The second therapeutic agent can be a second COH-SR compound or an anticancer drug that is not a COH-SR compound. In certain embodiments, the combination of administering the first and the second pharmaceutical compositions can show synergistic or additive effects in the treatment. In certain embodiments, the combination of administering the first and the second pharmaceutical compositions potentiates the cytotoxicity of the first COH-SR compound or the second therapeutic agent. The optimal dosages of each ingredient in the pharmaceutical compositions can be determined as described supra.

Examples of the anticancer drugs that are not the COH-SR compounds include, without limitation, chemotherapeutics such as TMZ, SN38, CPT-11, and 5-FU, and an antibody against RLIP76 (anti-RLIP76, e.g. anti-RLIP76 IgG).

In certain embodiments, the first COH-SR compound is COH-SR4 and the second therapeutic agent is a chemotherapeutic (e.g. TMZ, SN38, CPT-11, 5-FU) or anti-RLIP76. In certain embodiments, the first pharmaceutical composition is administered before the second pharmaceutical composition is applied. In certain embodiments, the first pharmaceutical composition is administered after the second pharmaceutical composition is applied. The optimal time difference between the administrations of the two pharmaceutical compositions can be minutes, hours, or days, which can be determined by those skilled in the art, and will vary with the particular compound in use, the strength of the preparation, the mode of administration, and the advancement of the condition treated. Additional factors depending on the particular subject being treated, including subject age, weight, gender, diet and time of administration, will result in a need to adjust dosages.

In certain embodiments, the first COH-SR compound is COH-SR4 and the second therapeutic agent is anti-RLIP76. The second pharmaceutical composition comprising anti-RLIP76 is administered to the subject first, and then the first pharmaceutical composition comprising COH-SR4 is administered after a first time period. The first time period is about 24 hours.

Without being bound by a specific mechanism, GST can be inhibited by the product formed by conjugation of GSH (GS-E). Thus, GS-E is actively transported out of cells to avoid product inhibition of GSTs (e.g. in a mercapturic acid pathway). The majority of GS-E transport is carried out by the non-ABC transporter, RLIP76. Thus, administering to the subject a pharmaceutical composition comprising anti-RLIP76 improves the therapeutic effects of the first COH-SR compound.

EXAMPLES

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Figure 4:
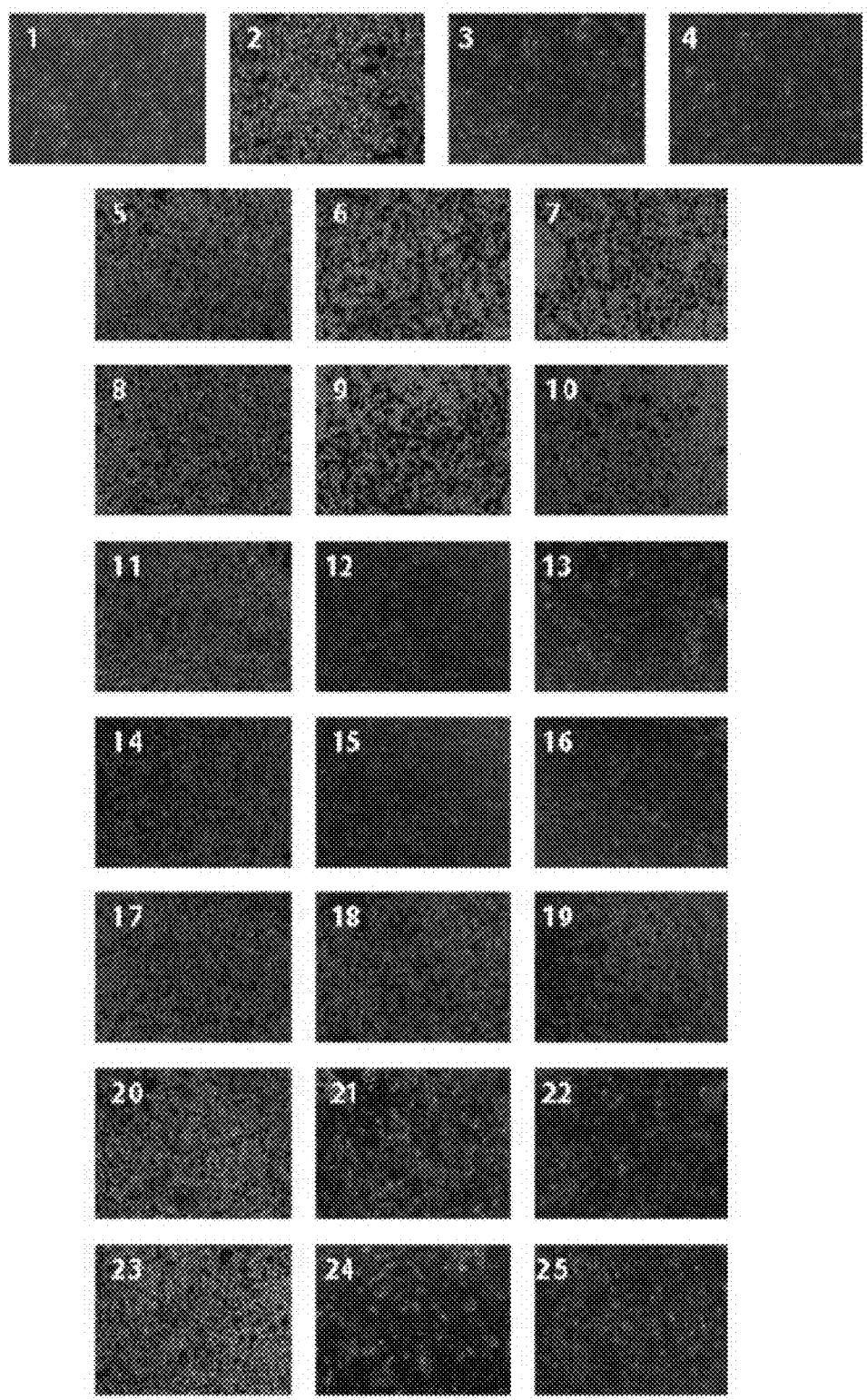
FIG. 4: Effects of COH-SR1, COH-SR2, COH-SR3, COH-SR4, COH-SR7, LR23 and LR59 on adipocyte differentiation of 3T3-L1 cells shown by morphological changes associated with adipogenesis using Oil Red O staining. 1=control (preadipocytes); 2=DM (preadipocytes treated with differentiating media); 3=DM+0.5 µM Trichostatin A (TSA); 4=DM+1 µM Apicidin; 5~7=DM+5, 10, 25 µM COH-SR1; 8~10=DM+5, 10, 15 µM COH-SR2; 11~13=DM+2.5, 5, 10 µM COH-SR3; 14~16=DM+1, 2.5, 5 µM COH-SR4; 17~19=DM+5, 10, 15 µM COH-SR7; 20~22=DM+10, 25, 50 µM LR23; and 23~25=DM+10, 25, 50 µM LR59.
Figure 5:
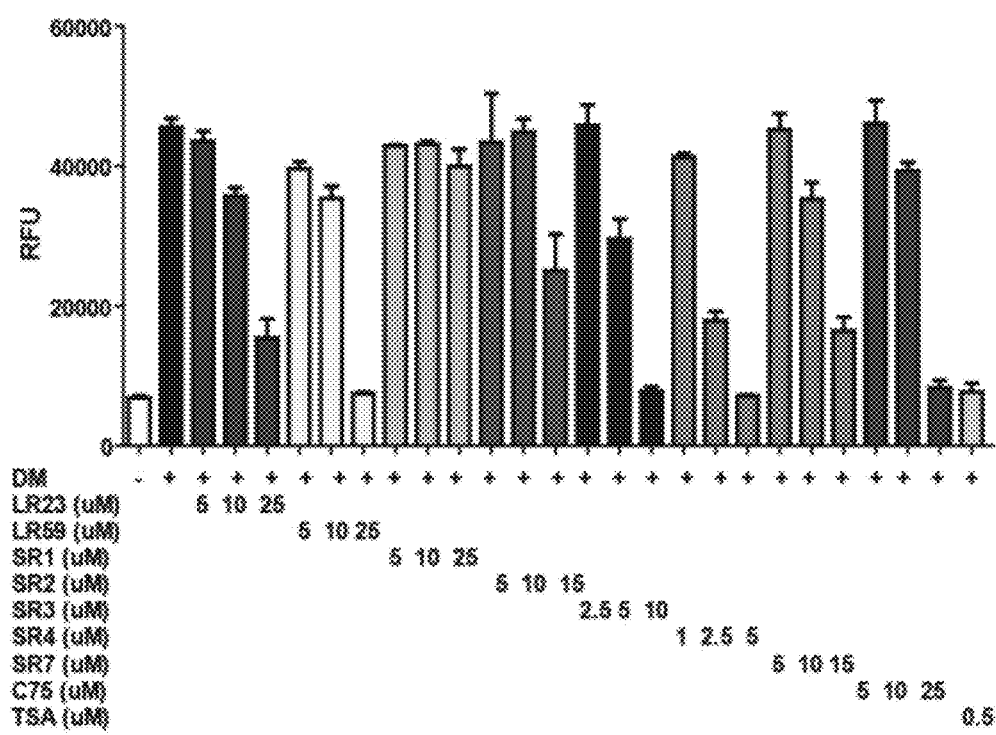
FIG. 5: Effects of COH-SR1, COH-SR2, COH-SR3, COH-SR4, COH-SR7, LR23 and LR59 on adipocyte differentiation of 3T3-L1 cells, shown by intracellular triglyceride contents (AdipoRed Assay™).

Modulation of COH-SR1, COH-SR2, COH-SR3, COH-SR4, COH-SR6, COH-SR7, LR23 and LR59 on Development of Preadipocyte Cells and Adipocyte Cells A) Effects of COH-SR1, COH-SR2, COH-SR3, COH-SR4, COH-SR6, COH-SR7, LR23 and LR59 on Adipocyte Differentiation of 3T3-L1 Cells (FIGS. 4 and 5)

In a 3T3-L1 cell model, under conditions that normally promoted differentiation of preadipocyte to adipocytes, all seven test compounds (COH-SR1, COH-SR2, COH-SR3, COH-SR4, COH-SR7, LR23 and LR59) dose-dependently inhibited differentiation and accumulation of lipid droplets, similar to TSA and apicidin, two known HDAC inhibitors, as well as C75, a known inhibitor of fatty acid synthase (FAS) (FIGS. 4 and 5).

Two-day post-confluent 3T3-L1 preadipocyte cells were allowed to differentiate for 7 days in the presence of nothing, DM only, DM+a test compound (COH-SR1, COH-SR2, COH-SR3, COH-SR4, COH-SR7, LR23 or LR59), or DM+a positive control (TSA, C75, or Apicidin). Morphological changes associated with adipogenesis were assessed by Oil Red O Staining and shown in FIG. 4.

Intracellular triglyceride contents were measured using AdipoRed Assay™, and the results were shown in relative fluorescence units (RFU) in FIG. 5.

Figure 6:
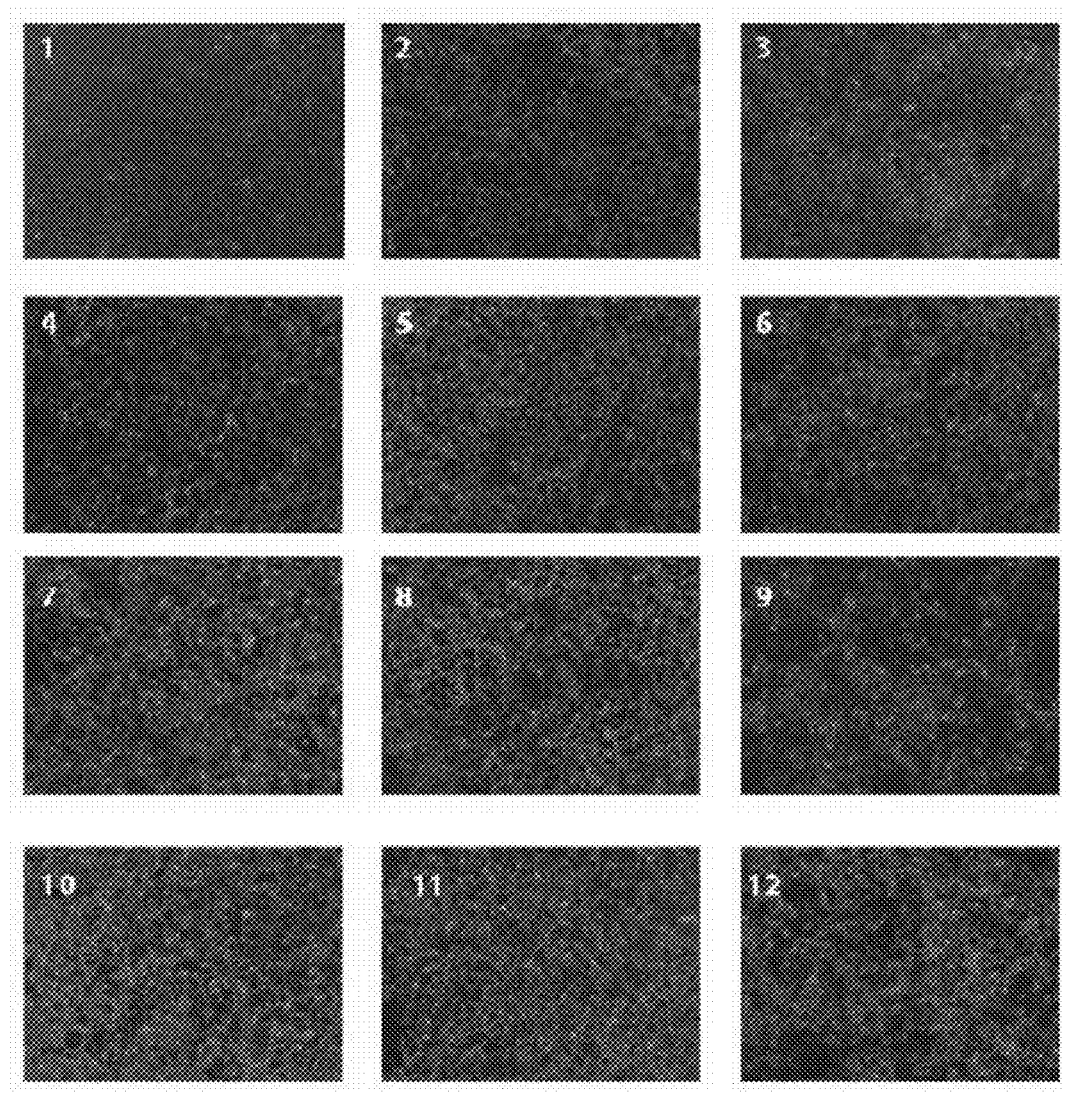
FIG. 6: Effects of COH-SR3, COH-SR7 and LR59 on the dedifferentiation of fully differentiated adipocytes, shown by the morphological change associated with adipogenesis using Oil Red O staining. 1=control, 2=DM, 3=DM+1 µM Apicidin, 4~6=DM+2.5, 5, 10 µM COH-SR3, 7~9=DM+10, 25, 50 µM COH-SR7, 10~12=DM+10, 25, 50 µM LR59.

B) Effects of COH-SR3, COH-SR7 and LR59 on Dedifferentiation of Fully Differentiated Adipocytes (FIG. 6)

Fully differentiated adipocyte cells were differentiated for 7 days and were treated for additional 3 days with DM+a test compound (COH-SR3, COH-SR7, or LR59), DM+a positive control (Apicidin, TSA or C75), DM, or nothing (control).

Morphological changes associated with adipogenesis were assessed by Oil Red O Staining (FIG. 6), and showed that COH-SR3, COH-SR7, and LR59 induced dedifferentiation of fully differentiated adipocytes.

Figure 7:
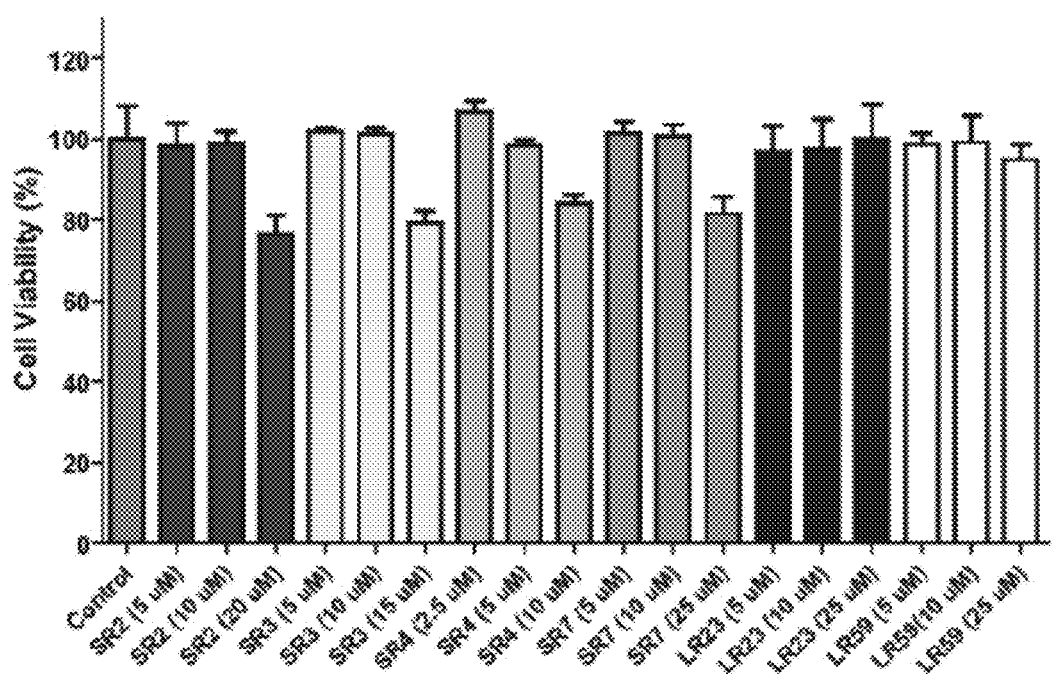
FIG. 7: Effects of COH-SR2, COH-SR3, COH-SR4, COH-SR7, LR23, and LR59 on cell viability of preadipocytes (MTT assay).

C) Effects of COH-SR2, COH-SR3, COH-SR4, COH-SR7, LR23 and LR59 On Preadipocytes (FIG. 7)

Undifferentiated 3T3-L1 cells were treated with COH-SR2, COH-SR3, COH-SR4, COH-SR7, LR23 or LR59 for 3 days at a concentration of 2.5 μM, 5 μM, 10 μM, 15 μM, 20 μM, or 25 μM. The cell viability for each treatment was determined by MTT assay (FIG. 7). The result showed that COH-SR2, COH-SR3, COH-SR4 and COH-SR7 inhibited the earlier stage of the adipogenic process (preadipocyte proliferation) as all four compounds inhibited growth of undifferentiated 3T3-L1 cells.

Figure 8:
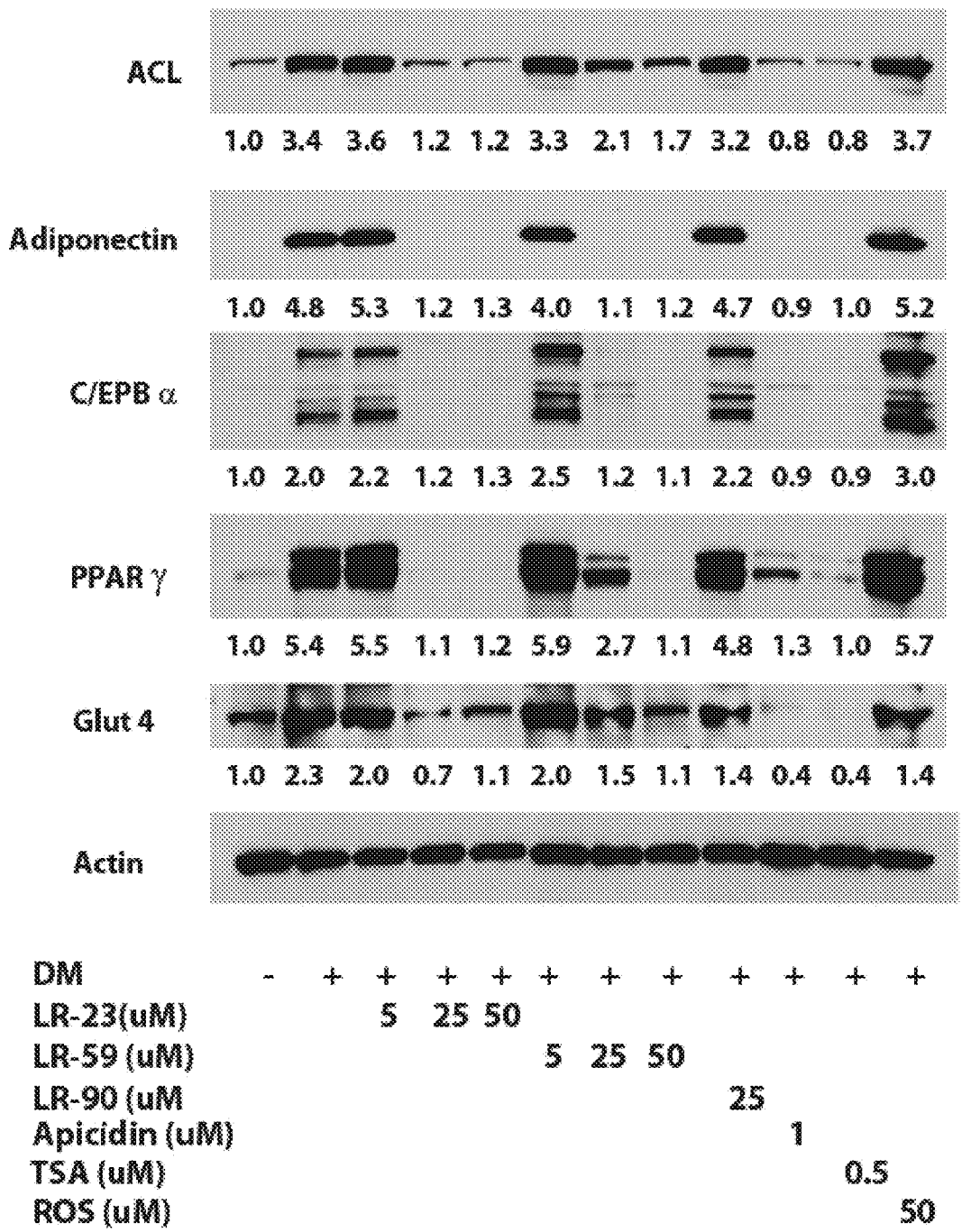
FIG. 8: Effects of LR23, LR59 and LR-90 on protein expression of selected adipogenic markers ACL, adiponectin, C/EBPα, Glut4, and PPARγ. DM=preadipocytes treated with differentiating media, TSA, Ros (Rosiglitazone, positive control).

D) Effects of LR23 and LR59 on Protein Expression of Selected Adipogenic Markers ACL, Adiponectin, C/EBPα, Glut4, and PPARγ (FIG. 8).

Post-confluent 3T3-L1 preadipocytes were differentiated for 7 days in the presence of differentiating media (DM), or DM+test compounds (LR23 (5 μM, 25 μM, or 50 μM), LR59 (5 μM, 25 μM, or 50 μM), LR-90 (25 μM), ROS (50 μM), TSA (0.5 μM) or apicidin (1 μM)). Protein levels were analyzed by Western blotting and the relative expression of each protein was quantified using a densitometer and calculated according to the reference bands of β-actin (FIG. 8). Numbers above each blot represent fold increase over control (undifferentiated preadipocytes).

It is shown that the expression of adipogenic marker genes such as PPARγ, C/EBPα, ACL and adiponectin, which are upregulated during adipocyte differentiation, was also inhibited by the test compounds.

Figure 9:
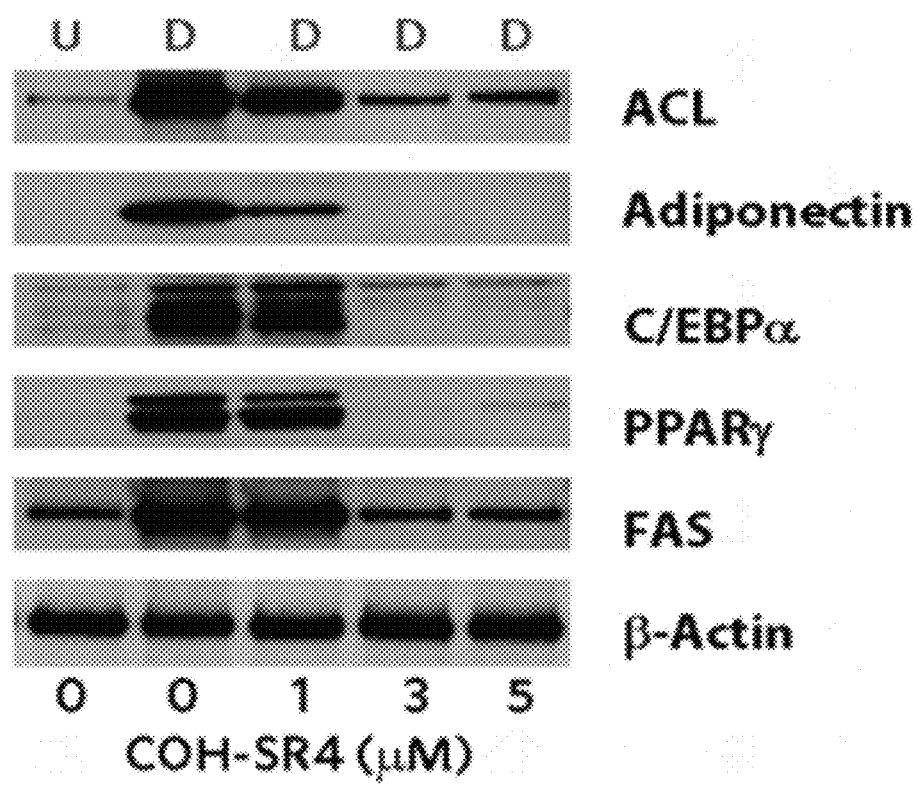
FIG. 9: Effects of COH-SR4 on adipocyte differentiation, COH-SR4 prevented accumulation of fat droplets as indicated by (A) reduced Oil Red O staining, (B) decreased intracellular triglyceride contents, and (C) decreased expression of key transcription factors (C/EBPα, PPARγ) and proteins (ACL, adiponectin, FAS) involved in adipocyte development.

E) Effects of COH-SR4 on Adipocyte Differentiation (FIG. 9)

T3-L1 preadipocytes cells were treated with differentiating media (DM) with COH-SR4 (1 μM, 3 μM, or 5 μM) or without for 7 days. COH-SR4 prevented accumulation of fat droplets, as shown by morphological changes associated with adipogenesis using Oil Red O staining (FIG. 9A), decreased intracellular triglyceride contents (FIG. 9B), and decreased expression of key transcription factors (C/EBPα, PPARγ) and proteins (ACL, adiponectin, FAS) involved in adipocyte development (FIG. 9C). As used in FIG. 9C, U=undifferentiated, D=differentiated with cocktail media.

F) Conclusion.

The results showed that in the 3T3-L1 cell model, under conditions that normally promote differentiation of preadipocyte to adipocytes, COH-SR1, COH-SR2, COH-SR3, COH-SR4, COH-SR7, LR23 and LR59 attenuated the differentiation and accumulation of lipid droplets, similar to TSA and apicidin, two known HDAC inhibitors, as well as C75, a specific inhibitor of FAS (FIG. 4). In addition, intracellular triglyceride contents were also dose-dependently reduced by all these compounds (FIG. 5). COH-SR3, COH-SR7 and LR59 treatment also induced dedifferentiation of fully differentiated adipocytes, as evidenced by the fact that these compounds decreased Oil Red O-staining in mature adipocytes (FIG. 6).

Undifferentiated 3T3-LI cells treated with COH-SR2, COH-SR3, and COH-SR4 inhibited the earlier stage of the adipogenic process (preadipocyte proliferation) as all three compounds inhibited growth of undifferentiated 3T3-L1 cells (FIG. 7). Such inhibition on preadipocyte proliferation may be associated with cell cycle arrest similar to what were observed in cancer cells such as HL-60 leukemia cells (see Example 3) where COH-SR3 and COH-SR4, as well as all-trans retinoic acid (ATRA, as a control) prevented cellular proliferation and arrested growth via G0/G1 arrest and modulation of various cyclin-dependent kinases (CDKs) and induction of p21 and p27.

Thus the results suggest that treatment of adipocytes with the COH-SR compounds prevented the adipocyte differentiation and accumulation of triglycerides in these cells. The COH-SR compounds may find therapeutic application in the prevention of obesity by reducing fat mass and lowering body weights.

Example 2

Effects of COH-SR Compounds on AMPK Activations in Cancer Cells and Adipose Cells (FIG. 10)

Activation of AMPK was associated with the phosphorylation of the α-subunit on Thr-172 of as assessed using phospho-specific antibodies (FIG. 10). AMPK activation also leads to the increased phosphorylation of the target protein acetyl-CoA carboxylase (ACC) (FIG. 100B).

Cells of each cell lines (Hela, HL-60, and 3T3-L1) were treated for 1 hour with a test compound (COH-SR4, COH-SR9, COH-SR16, or COH-SR18) at a concentration of 1 µM, 3 µM, or 5 µM, or AICAR (5-aminoimidazole-4-carboxamideriboside, an AMPK agonist used as positive control) at a concentration of 500 µM, or none of the above (the untreated cells as negative control). Total cell lysates from the untreated cells and the cells treated with a test compound or AICAR were analyzed by Western blot assay using specific antibodies against phospho-AMPK, phospho-ACC, total AMPK and total ACC.

COH-SR compounds activated AMPK in Hela ovarian cancer cell line (FIG. 10A). HeLa cells lack the LKB1 gene and do not express LKB1 mRNA and protein, thus indicating that COH-SR compounds activated AMPK independent of the LKB1 pathway.

COH-SR4 showed the highest potency among the COH-SR compounds tested (FIG. 10A).

FIG. 10B showed that COH-SR4 activated AMPK in human promyelocytic leukemia HL-60 cell lines and adipose cell line 3T3-L1.

Example 3

Figure 13:
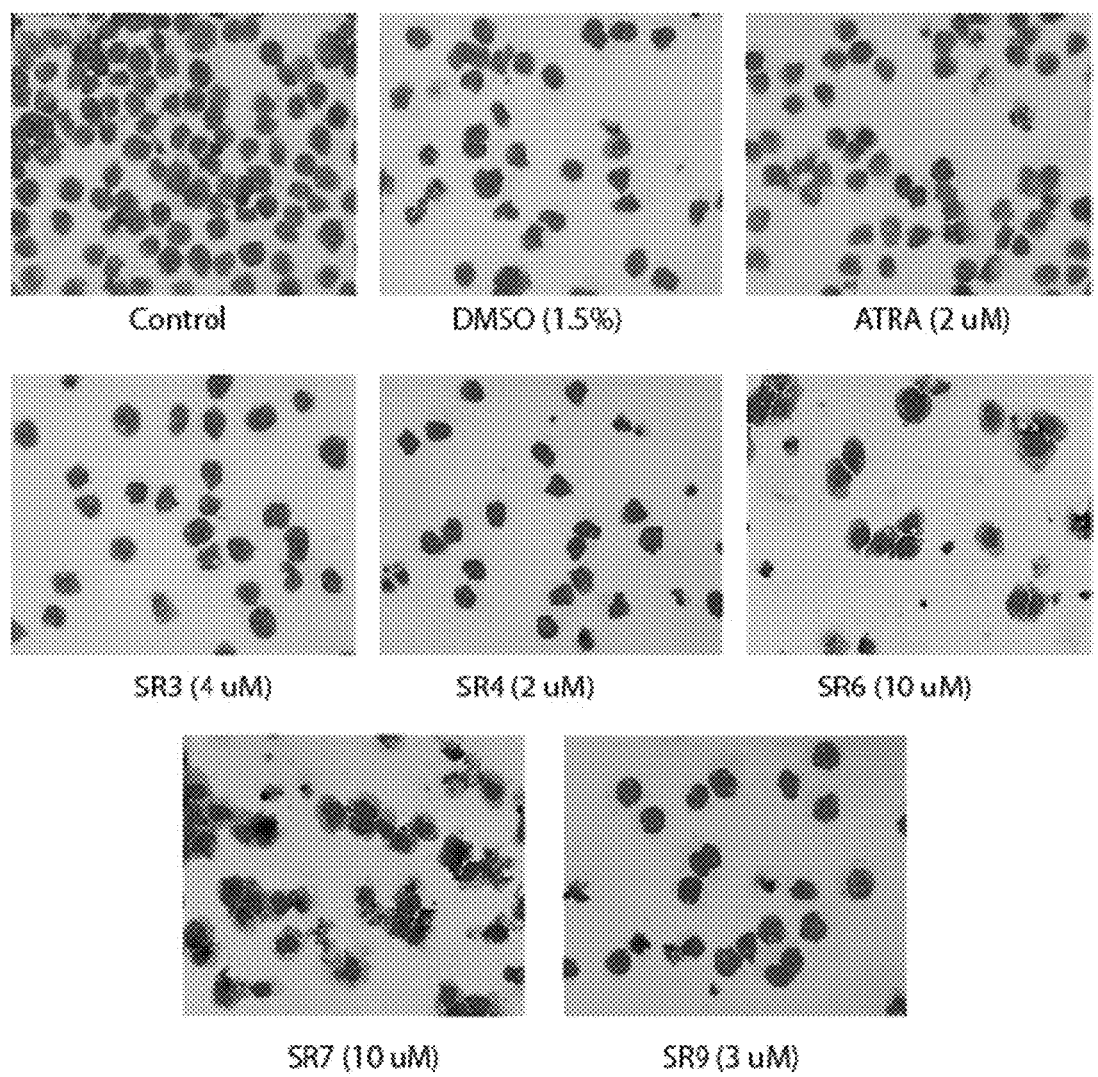
FIG. 13: COH-SR3, COH-SR4, COH-SR6, COH-SR7, and COH-SR9 induced myeloid differentiation of HL-60 cells.

COH-SR3, COH-SR4, COH-SR6, COH-SR7, COH-SR9 and COH-SR14 Inhibited Growth and Proliferation of Human Meyoblastic Leukemia Cell Line (HL-60) (FIGS. 11~13)

(A) COH-SR3, COH-SR4, COH-SR9, and COH-SR14 Inhibited Growth and Proliferation of HL-60 Cells, Shown by Dose and/or Time-dependent Effects Thereof on Cell Viability of HL-60 Cells (FIGS. 11 and 12).

HL-60 is an uncommitted human meyoblastic leukemia cell line that grows avidly in culture. HL-60 cells ($5 \times 10^4$) were incubated with a test compound (COH-SR3, COH-SR4, COH-SR6, COH-SR7, COH-SR9, or COH-SR14) of various concentrations (1~15 µM) or without any test compound for 48 hours. The numbers of viable cells after the incubation periods were measured by the MTT assay and shown in FIGS. 11A and 11B. Numbers after each compound represented the concentration in µM in FIG. 11A. COH-SR3, COH-SR4, COH-SR6, COH-SR7, COH-SR9 exhibited cytotoxicity and prevented cell proliferation of HL-60 leukemia cells (FIG. 11A). COH-SR3, COH-SR4, COH-SR9, and COH-SR14 exhibited cytotoxicity and prevented cell proliferation of HL-60 leukemia cells with $IC_{50}$ of less than 5 µM (FIG. 11B). Three independent experiments were carried out with 3 duplications each, and data are shown as mean±SE.

A dose and time-dependent cytotoxic and anti-proliferative effects of COH-SR4 and COH-SR9 on HL-60 cells were observed, as shown in FIG. 12A and FIG. 12B respectively. COH-SR4 and COH-SR9 had an $IC_{50}$ around 1.7 µM and 2.5 µM, respectively, after 72 hours incubation with the test compounds (FIGS. 12A and 12B). Three independent experiments were carried out with 3 duplications each, and data are shown as mean±SE.

(B) Test Compounds (COH-SR3, COH-SR4, COH-SR6, COH-SR7, and COH-SR9) Induced Myeloid Differentiation of HL-60 Cells (FIG. 13).

HL-60 cells are also bipotent cells with the capacity to differentiate either into myeloid or monocytes/macrophages. The effects of the test compounds to induce differentiation in these cells were also tested and shown in FIG. 13.

HL-60 cells were incubated with a test compound at various concentrations (2~10 µM), DMSO, or without any test compound for 48 hours, and then examined for morphologic changes by Giemsa-Wright stain. The results were observed microscopically and shown in FIG. 13 at a magnification of ×400. HL-60 cells treated with COH-SR3, COH-SR4, COH-SR6, COH-SR7, or COH-SR9 exhibited cytoplasmic vacuolation, reduced nucleus-to-cytoplasmic ratio, and absence of prominent nucleoli (FIG. 13). Such results were similar to cells treated with DMSO or all-trans retinoic acid (ATRA), wherein DMSO or ATRA terminally differentiated HL-60 cells into myeloid cells (FIG. 13).

(C) COH-SR4 and COH-SR9 Induced Superoxide Production as Indicated by the Increased Numbers of Nitro Blue Tetrazolium (NBT)-positive Cells (FIG. 14).

HL-60 cells ($2.5 \times 10^5$) were treated with or without a test compound for 48 hours and then stained with NBT, wherein positively-stained cells appeared as purple black (FIG. 14A). NBT positive cells were counted and the overall percentage was calculated based on 200 total cells counted for each treatment. Three-four independent experiments were carried out, and data are shown as mean±SE (FIG. 14B). This measurement of "oxidative burst" by the NBT assay is a well-known and extensively tested functional marker of HL-60 cell differentiation.

Additionally, using flow cytometry analyses, cell differentiation was further confirmed by dose-dependent increase in expression of both CD11b and CD14 monocyte/macrophage differentiation markers on the cell surface of HL-60 cells treated with COH-SR4 or COH-SR9 (FIGS. 14C and 14D). HL-60 cells ($2.5 \times 10^5$) were incubated with a test compound (COH-SR4 or COH-SR9) at a concentration of 0.5 µM, 1 µM, 2 µM, or 3 µM, or without any COH-SR compound for 48 hours and then assessed for the surface expression of CD11b (FIG. 14C) and CD14 (FIG. 14D) by flow cytometry, respectively. Three-four independent experiments were carried out, and data are shown as mean±SE (FIGS. 14C and 14D).

Cellular differentiation of HL-60 leukemia cells into mature terminal cells is associated with the inhibition of cell proliferation, followed by programmed cell death or apoptosis. It is known that several anti-cancer agents may alter regulation of the cell cycle machinery, resulting in an arrest of cells in different phases of the cell cycle and thereby reducing the growth and proliferation even inducing apoptosis of cancerous cells. The results showed that COH-SR compounds can do the same.

Figure 15:
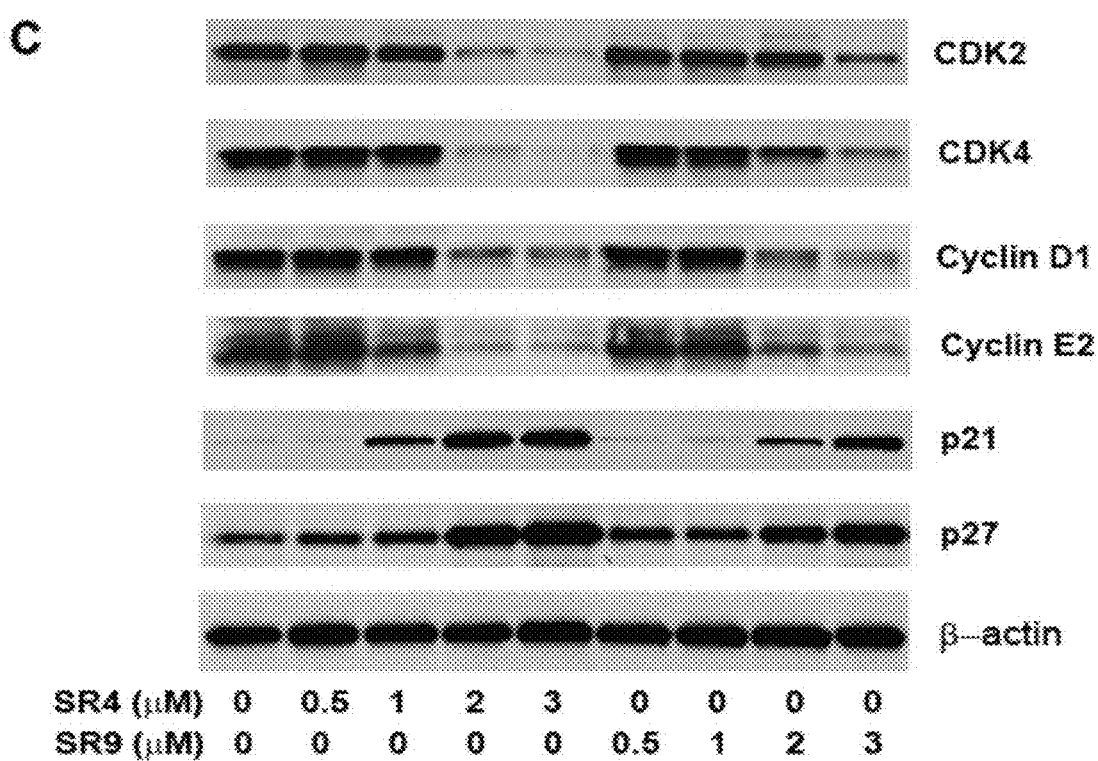
FIG. 15: COH-SR4 and COH-SR9 induced a dose and time-dependent G0/G1 phase arrest in HL-60 cells. (A) Dose-dependent effects of COH-SR4 and COH-SR9 on the cell cycle progression in HL-60; (B) Kinetics of G0/G1 phase arrest induced by COH-SR4 and COH-SR9; and (C) Representative Western blots showing the effects of COH-SR4 and COH-SR9 on cell cycle regulatory proteins.

(D) COH-SR4 and COH-SR9 Induced a Dose and Time-Dependent G0/G1 Phase Arrest in HL-60 Cells (FIG. 15).

As COH-SR compounds induced significant growth inhibition of HL-60 cells, the effects of these compounds on the cell cycle progression of HL-60 cells were investigated using flow cytometry. HL-60 cells ($1\times10^6$) were incubated with a test compound (COH-SR4 or COH-SR9) at various concentrations (0.5~3 µM) for 48 hours, washed and harvested. The cells were then fixed and stained with propodium iodide (PI) and the DNA content was analyzed by flow cytometry. Results of each figure were from 3-4 independent experiments. The cell number in each cell cycle phase was calculated and expressed as overall percentage (FIG. 15A). The percentage of cells in G0/G1 were measured from 0-48-hour treatment with test compounds (FIG. 15B), data expressed as mean±SE.

As shown in FIGS. 15A and 15B, HL-60 cells treated with COH-SR4 or COH-SR9 resulted in a dose- and time-dependent G0/G1 phase arrest. After 24-hour treatment with COH-SR4 or COH-SR9, more than 70% of cells were stuck at this phase compared with 46% in the control, and within 48-hour treatment, 85% of the viable cells were arrested at this stage. Concomitant with this increase in percentage of cells in the G0/G1 phase was a significant decrease in the percentage of cells in the S phase (from 47% in the control cells versus 10% and 13% in 3 µM COH-SR4 and 3 µM COH-SR9, respectively). These results suggest that COH-SR compound-induced growth inhibition was strongly associated with its induction of cell cycle arrest.

Because cyclins (e.g. cyclin D1 and E2) and cyclin dependent kinases (CDKs) such as CDK2 and CDK4 play critical roles in promoting G1 phase progression, the effects of the COH-SR compounds on these regulatory proteins were examined.

HL-60 cells were treated without or with COH-SR4 or COH-SR9 at a concentration of 0.5 µM, 1 µM, 2 µM, or 3 µM for 24 hours. Then the total cell lysates from the treated cells or untreated cells were resolved under electrophoresis and immunoblotted with antibodies against cyclin D1, cyclin E2, CDK2, CDK4, p21WAF1/Cip1, p27Kip1, and β-actin. β-actin served as an internal control. Densitometric quantitation was performed on each blot and the arbitrary numbers above each band represent the fold increase/decrease compared with untreated control. Representative Western blot results (FIG. 15C) showed that treatment with either test compound for 24 hours resulted in dose-dependent reduction in the protein levels of cyclin D1, cyclin E2, CDK2 and CDK4. In contrast, the protein levels of the CDK inhibitors p21WAF1/Cip1 and p27Kip1 were both upregulated by either compound. These kinase inhibitors are known to interfere with cell cycle progression to cause phase-specific cycle arrest by perturbing the phosphorylation process through direct interaction with their target proteins (cyclins or CDK). Therefore, these data indicate that the inhibitory effect of both COH-SR compounds on HL-60 proliferation may be a result of the induction of cell cycle arrest at the G0/G1 phase through changes in the expressions of G1 associated regulatory proteins.

Figure 16:
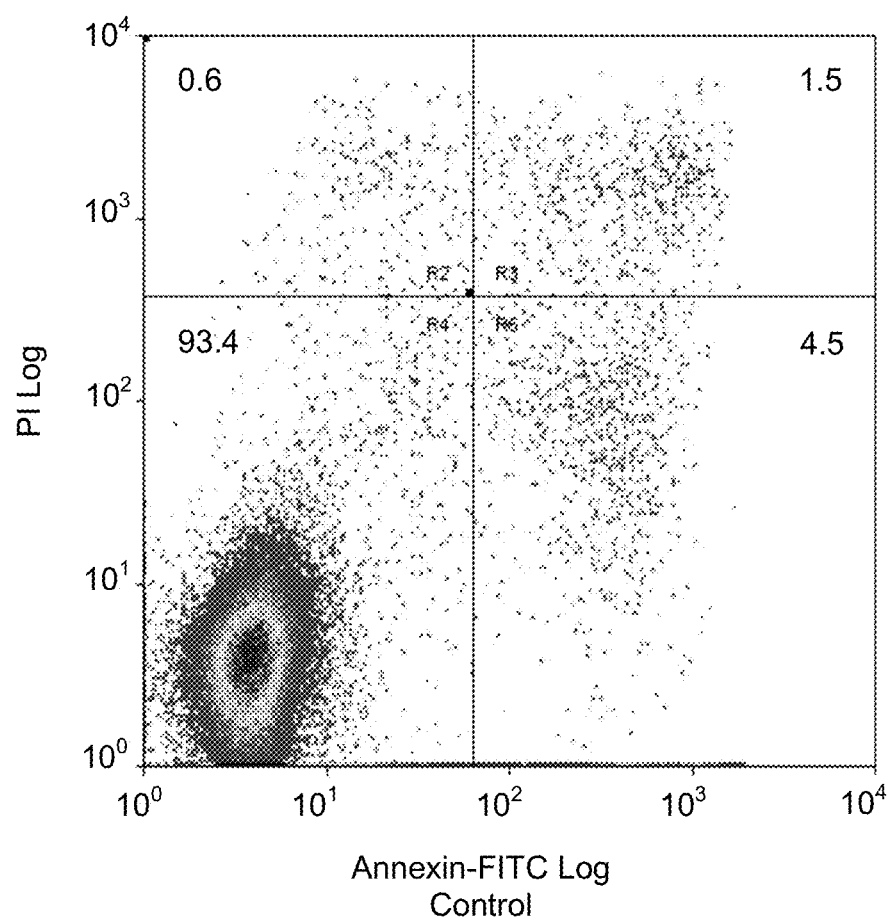
FIG. 16: COH-SR4 and COH-SR9 induced apoptosis of HL-60 as shown by representative cytograms of Annexin V-PI double staining. (A) Control; (B) ATRA at 2 μM; (C) COH-SR4 at 1 μM; (D) COH-SR9 at 1 μM; (E) COH-SR4 at 2 μM; (F) COH-SR9 at 2 μM; (G) COH-SR4 at 3 μM; (H) COH-SR9 at 3 μM.
Figure 16:
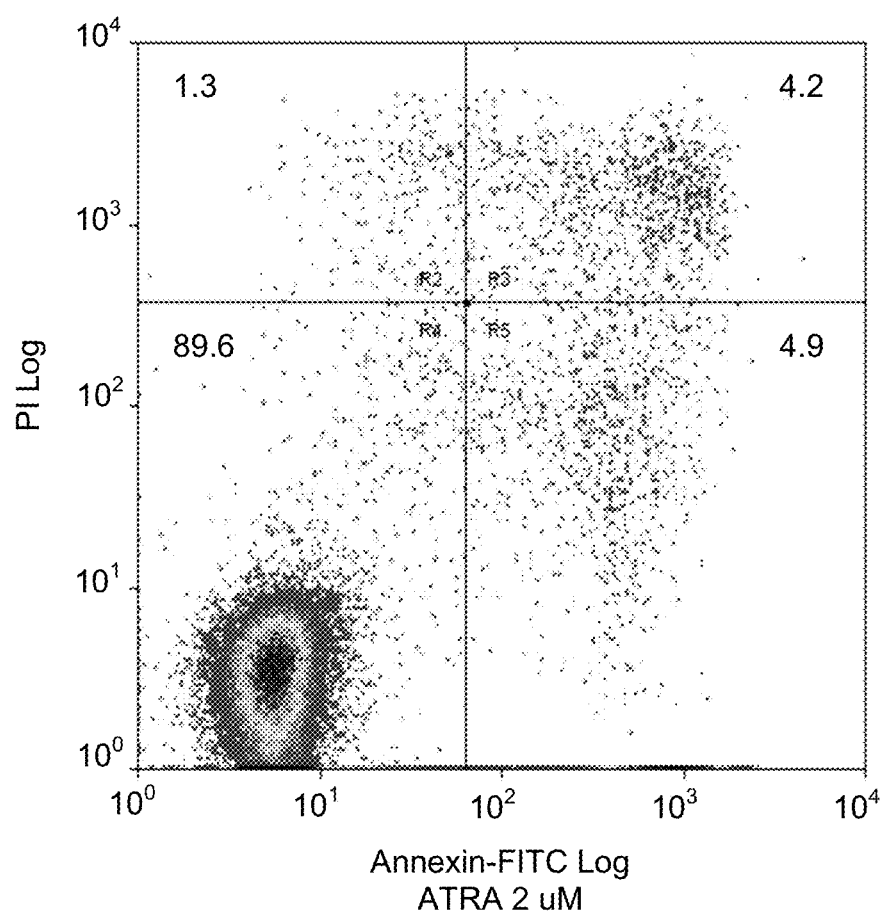
Figure 16:
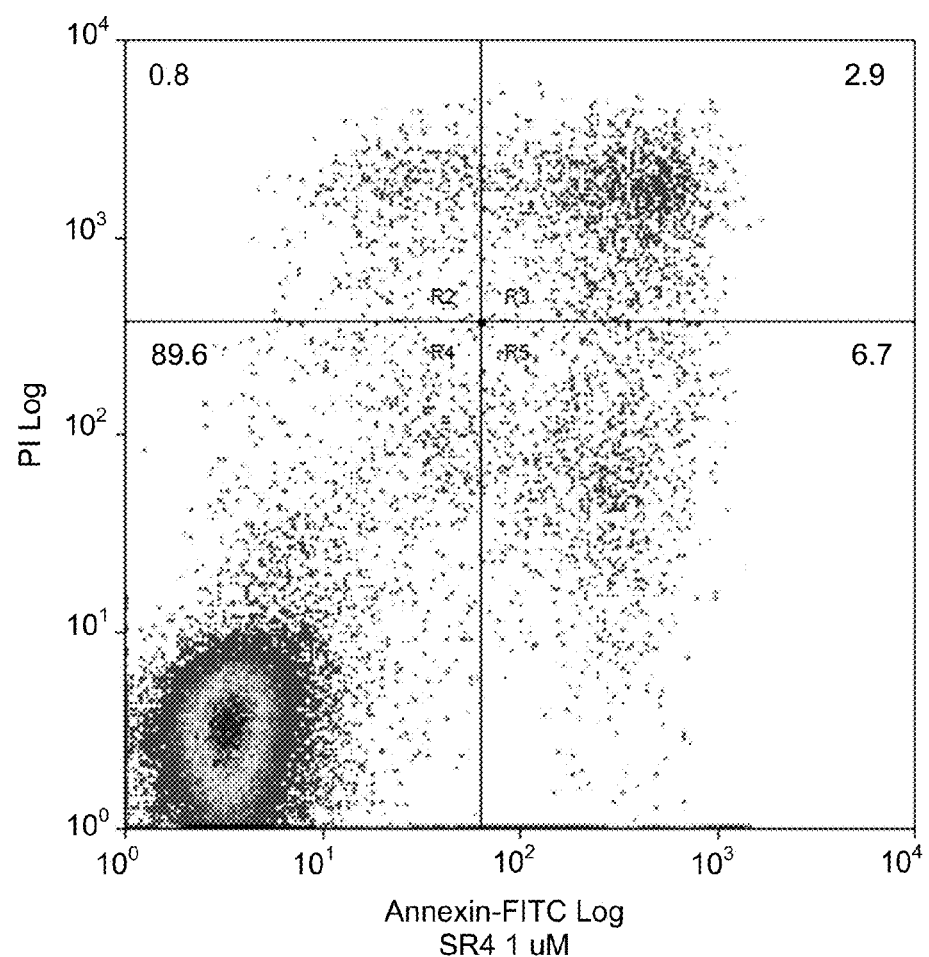
Figure 16:
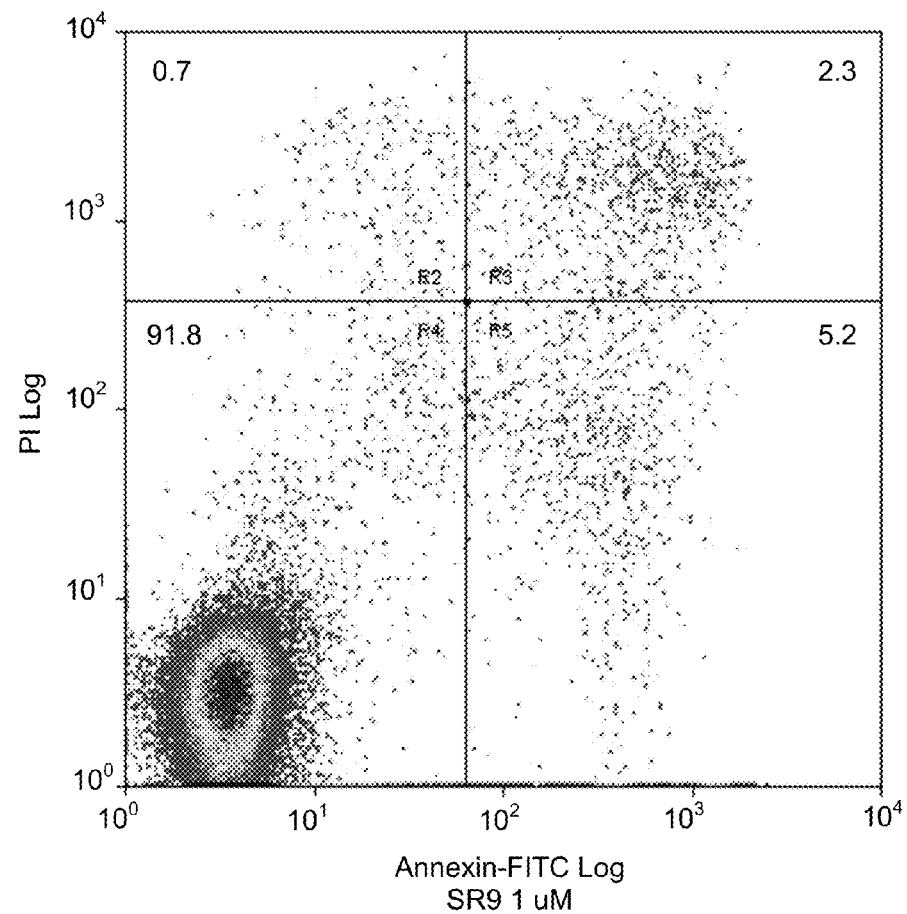
Figure 16:
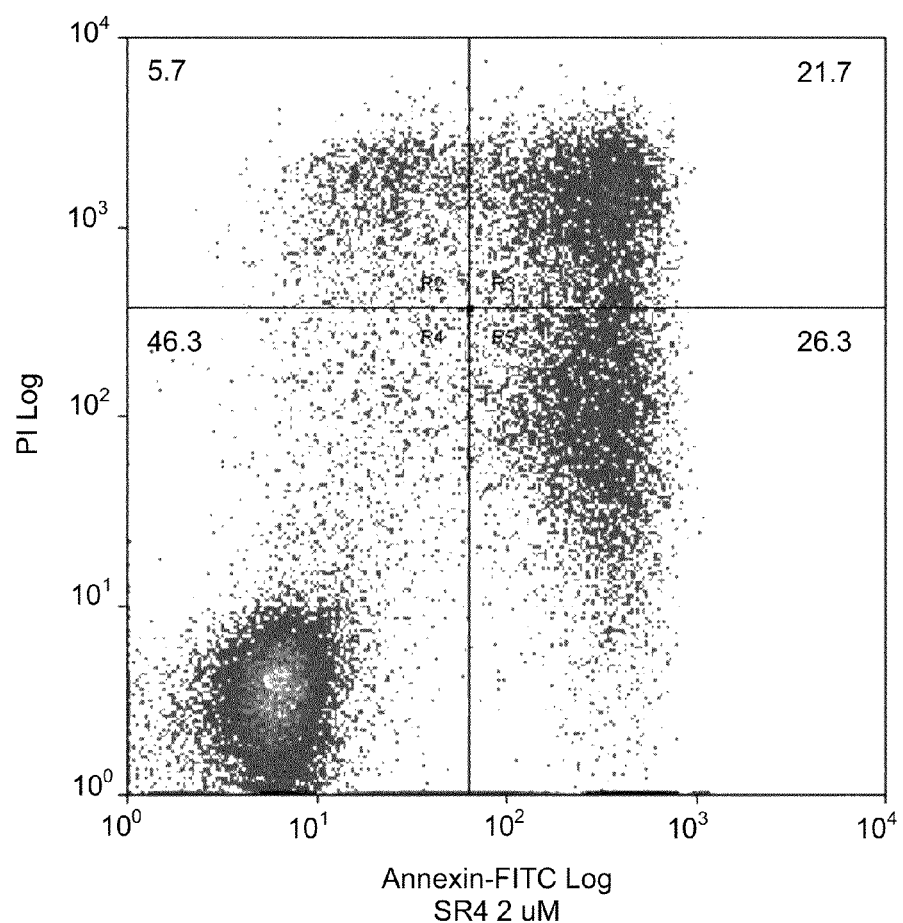
Figure 16:
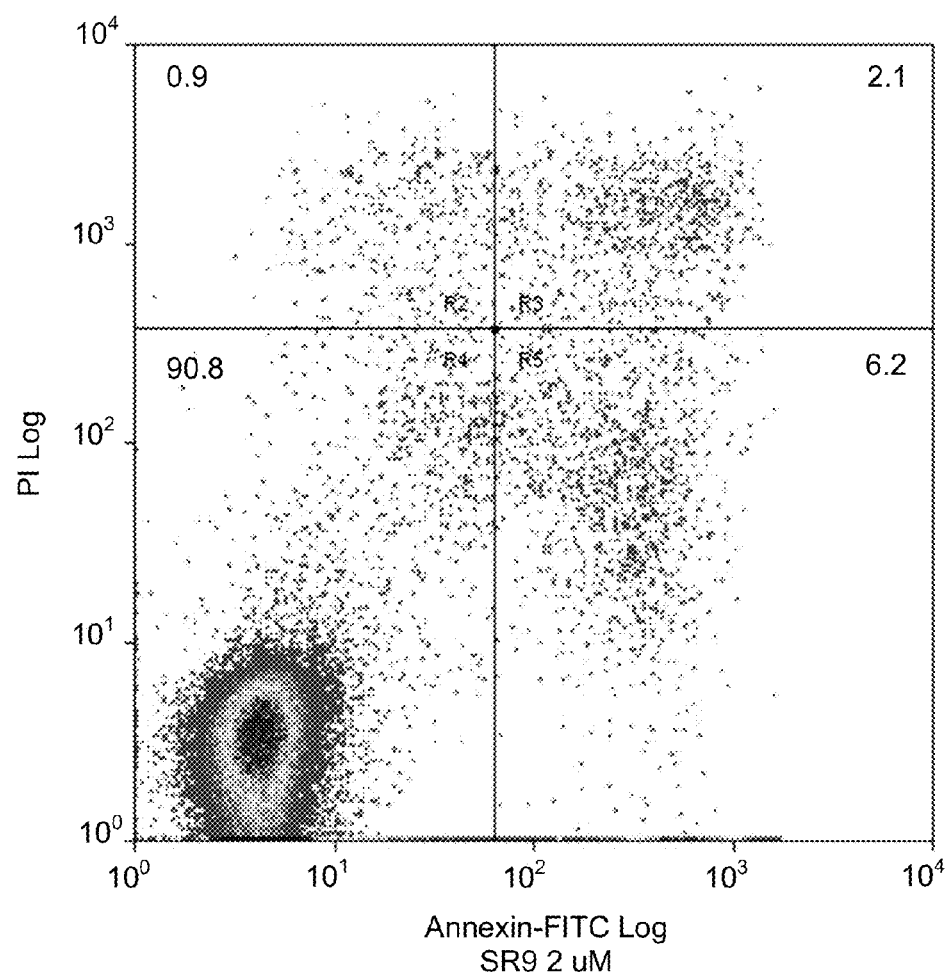
Figure 16:
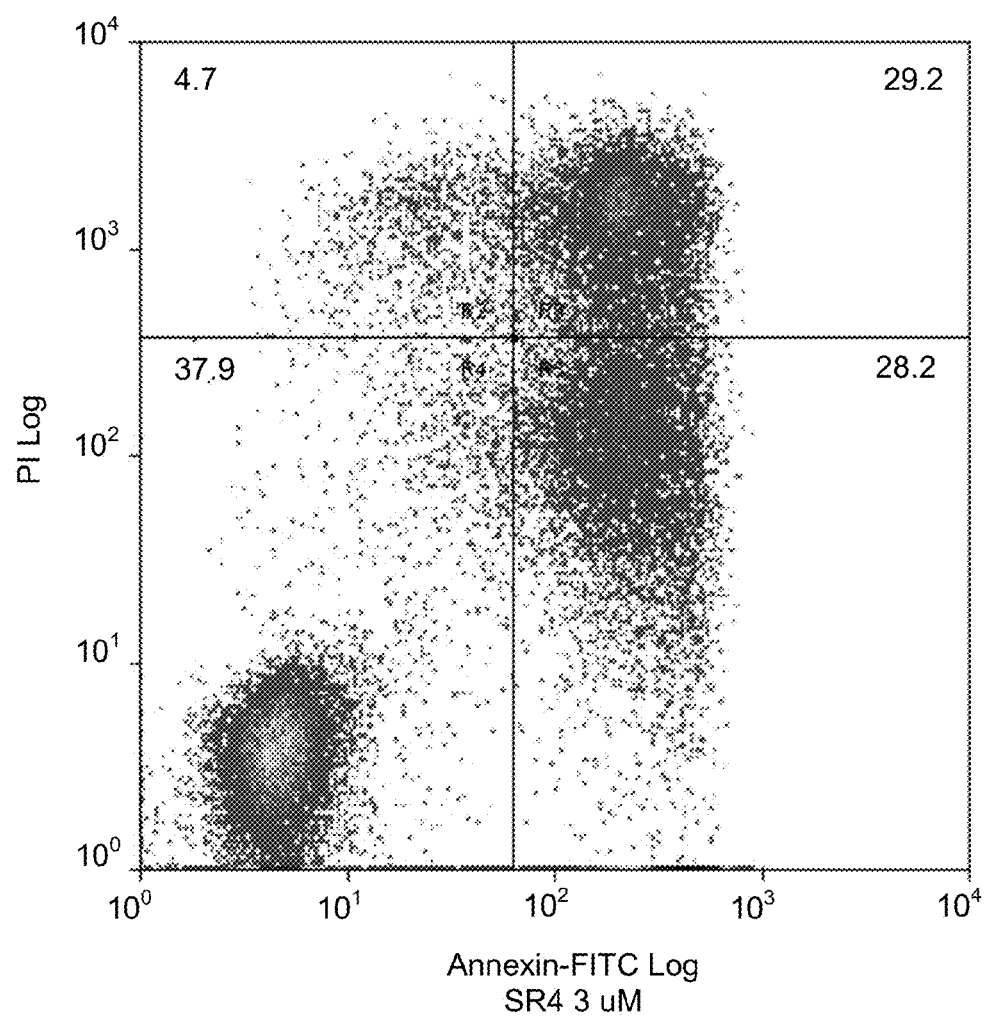
Figure 16:
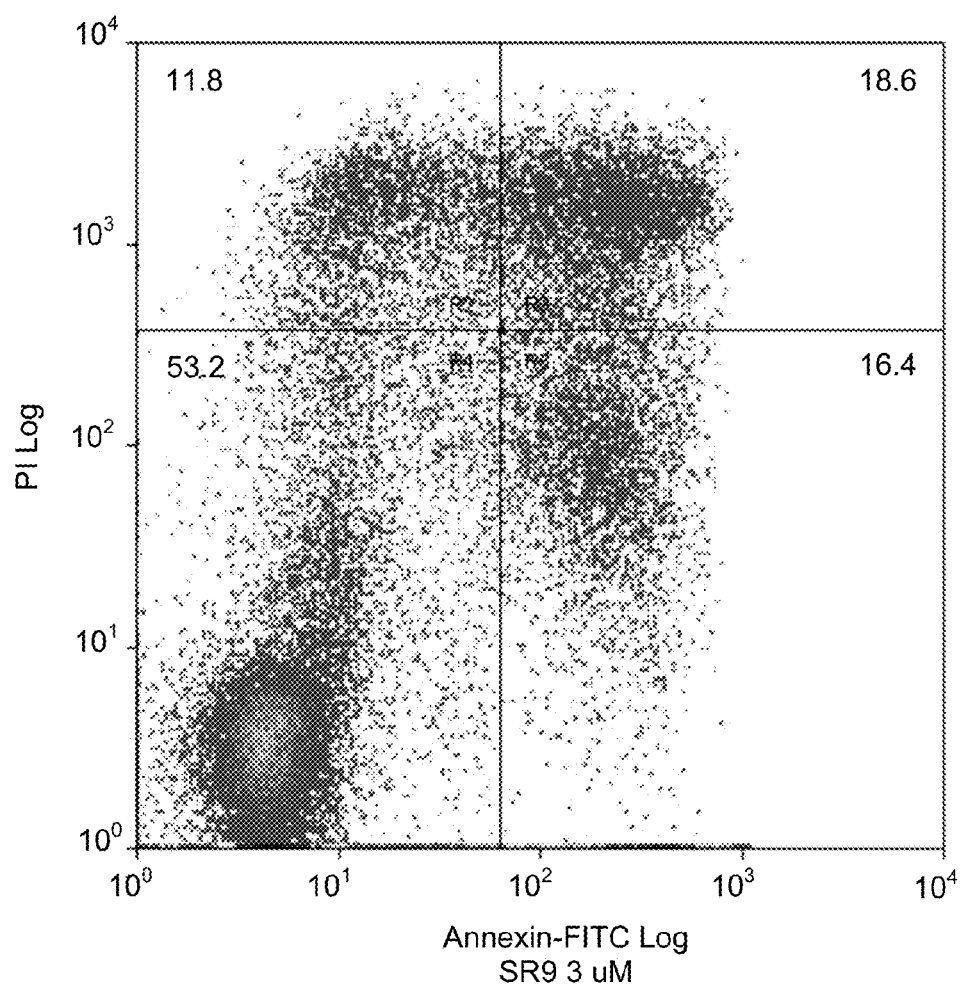
Figure 17:
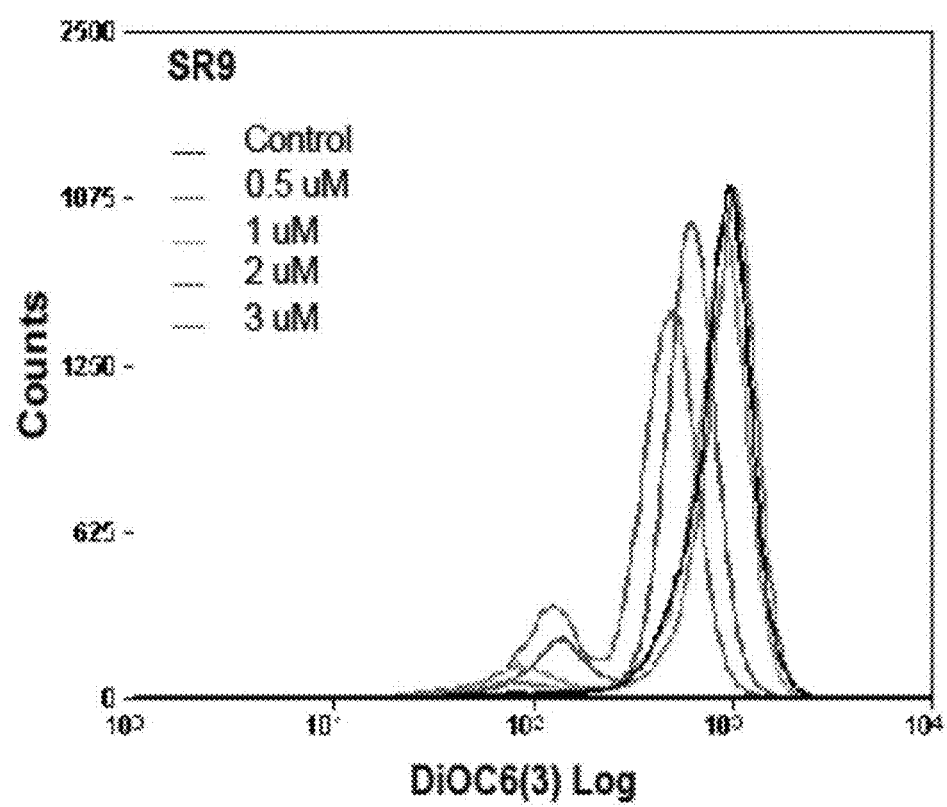
FIG. 17: COH-SR4 and COH-SR9 induced apoptosis of HL-60. (A) Representative photographs of DNA fragments obtained from HL-60 cells treated with or without COH-SR4 or COH-SR9; (B) Depolarization of the mitochondrial membrane as a consequence of treatments with COH-SR4; and (C) Depolarization of the mitochondrial membrane as a consequence of treatments with COH-SR9.

(E) COH-SR4 and COH-SR9 Induced Apoptosis of HL-60 (FIGS. 16~18)

Data showed that after/or during $G_0/G_1$ phase arrest, COH-SR4 and COH-SR9 treated HL-60 cells underwent apoptosis as indicated by increased Annexin V-PI positive stainings (FIG. 16), dose-dependent increased DNA fragmentation (FIG. 17A), reduced fluorescence intensity of DiOC6(3) (FIG. 17B and FIG. 17C), higher caspase 3/7 and caspase 9 activity (FIG. 18A), and release of cytochrome c into the cytoplasm and PARP enzyme activation (FIG. 18B).

HL-60 ($5\times10^5$) cells were incubated with a test compound (COH-SR4 or COH-SR9), ATRA, or nothing (Control) for 48 hours, washed and harvested. The cells were then fixed and double stained with Annexin V-FITC and propodium iodide (PI) and analyzed by flow cytometry. Conjugation of Annexin V and PI staining was used to identify apoptosis cells (early stage and late stage), normal/viable cells and necrotic cells. The percentage distribution of normal/viable (R3, lower left quadrant), early apoptotic (R4, lower right quadrant), late apoptotic (R2, upper right quadrant) and necrotic cells (R1, upper left quadrant) was calculated using Summit software. The percentages of apoptotic cells after treatment with various doses of each compound are shown in FIG. 16. Both COH-SR4 and COH-SR9 treatment of HL-60 cells increased the number of early apoptotic and late apoptotic cells in a dose-dependent manner compared with untreated cells. At 3 µM, overall apoptotic cells were ~60% and 40% for COH-SR4 and COHSR9, respectively.

Additionally, exposure of HL-60 cells to COH-SR4 or COH-SR9 led to dose-dependent DNA fragmentation as indicated by the formation of lower molecular weight DNA fragments (DNA ladder) in the agarose gel, whereas control cells contained only high-molecular weight DNA and showed no evidence of DNA ladder (FIG. 17A). DNA was stained with ethidium bromide after electrophoresis on 1.5% agarose gel and then visualized under UV light.

To test whether mitochondrial membrane disruption was involved in the apoptotic effects of COH-SR4 and COH-SR9, fluorescent cationic lipophilic dye DiOC6(3) was used and monitored using flow cytometry. HL-60 cells were exposed to various concentrations of COH-SR4 or COH-SR9 for 4 hours. After incubation, cells were rinsed and stained with the cationic fluorescent dye DiOC6(3) and then the overall fluorescence was analyzed by flow cytometry. HL-60 cells treated with COH-SR4 (FIG. 17B) or COH-SR9 (FIG. 17C) showed decreased overall DiOC6(3) fluorescent intensity compared with control cells, as the fluorescence signals shifted to the left with increasing dose of the test compounds. Reduction of the fluorescence intensity of DiOC6(3) is indicative of the cells undergoing mitochondrial depolarization and loss of Δψmt. This effect, which has been commonly observed with other anticancer drugs irrespective of the cell type, generally defines an early but already irreversible stage of apoptosis.

Moreover, treatment with COH-SR compounds exhibited a dose-dependent activation of both caspase-3/7 and caspase-9 (FIG. 18A). HL-60 ($2.5\times10^4$) cells were seeded into 96-well plates and incubated with a test compound (COH-SR4 or COH-SR9) at various concentrations (0.5~3 µM) for 48 hours, then caspase-3/7 or caspase-9 activity was measured with the Caspase Glo kit (Promega), respectively. Data are expressed as mean±SE from 3 independent experiments (FIG. 18A), "*" in the figure means $p<0.05$ when compared to the untreated control.

Treatment of COH-SR compounds also triggered release of cytochrome c (14 kDa) into the cytoplasm and cleavage of full length PARP (116 kDa) into the 89 kDa fragment, all hallmarks of cells undergoing apoptosis (FIG. 18B). HL-60 cells were treated with COH-SR4 or COH-SR9 at various concentrations (0.5 μM~3 μM) or nothing for 24 hours. Cytochrome c (14 kDa) and cleavage of full length PARP (116 kDa) into the 89 kDa fragment were analyzed in untreated HL-60 cells and HL-60 cells treated with COH-SR4 or COH-SR9 by Western blot. Numbers below each blot represent fold increase in protein expression relative to the control as quantified by densitometry and calculated with reference to β-actin as an internal standard.

Example 4

COH-SR Compounds Inhibited Growth and Proliferation of Cancer Cells Such as Leukemia, Non-small Cell Lung Cancer, Colon Cancer, CNS Cancer, Melanoma, Ovarian Cancer, Renal Cancer, Prostate Cancer, and Breast Cancer (FIGS. 19~27)

Figure 19:
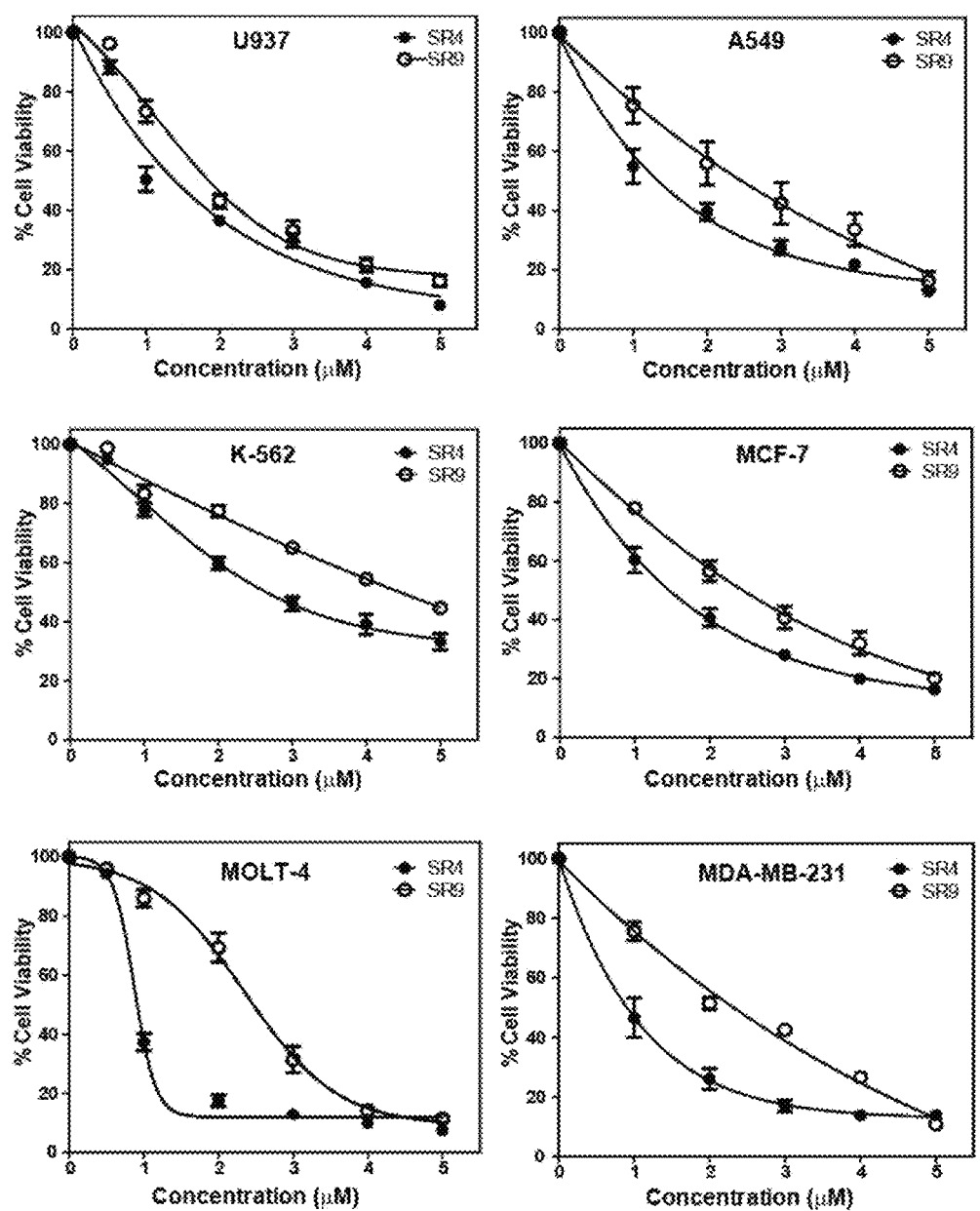
FIG. 19: Anti-proliferative effects of COH-SR4 and COH-SR9 against leukemia (U937, K-562, MOLT-4), breast cancer (MCF-7, MDA-MB-231), and small lung cancer cells (A549).
Figure 21:
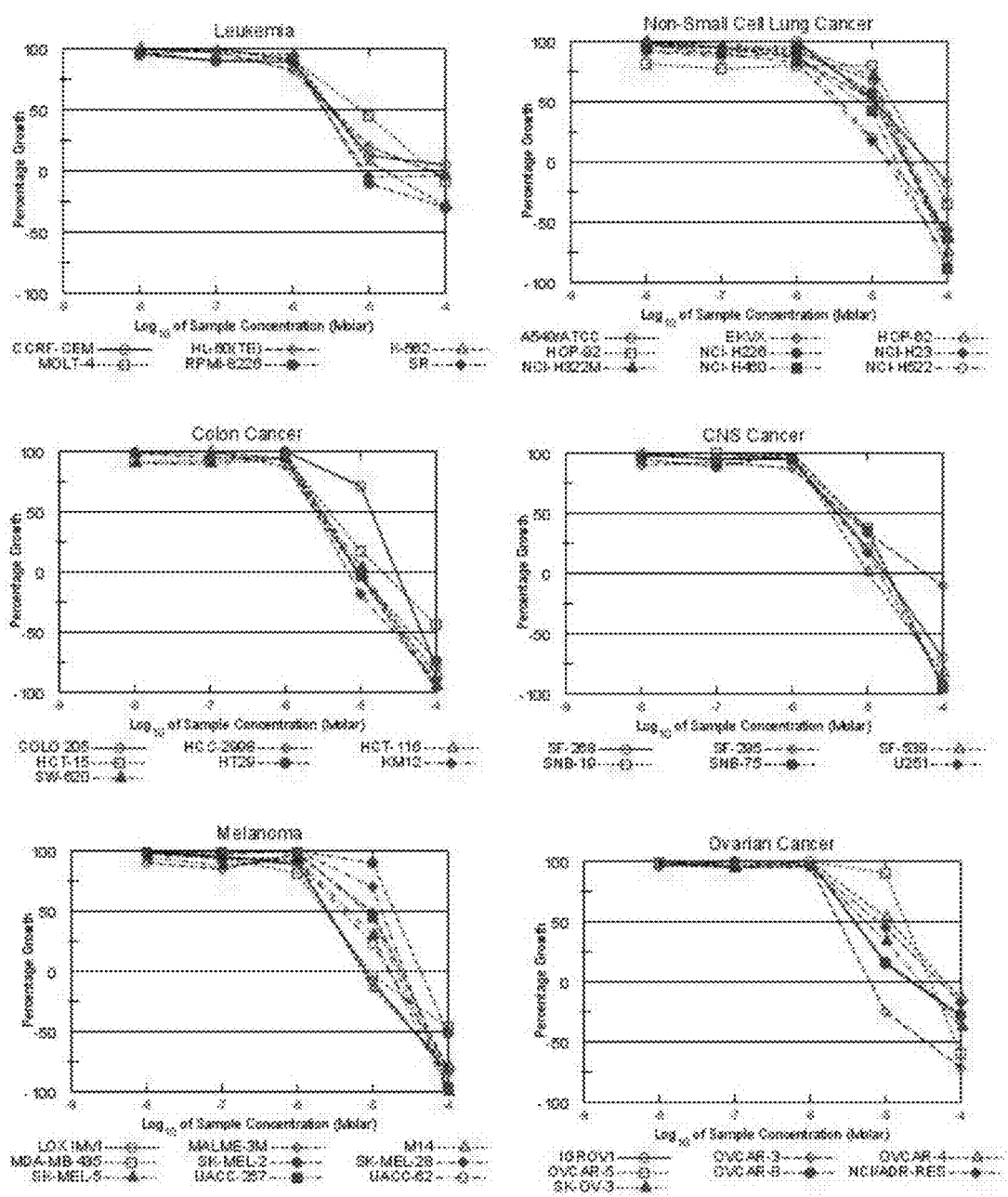
FIG. 21: NIH NCI-60 Developmental Therapeutics Program (DTP) dose response curves for COH-SR2.
Figure 21:
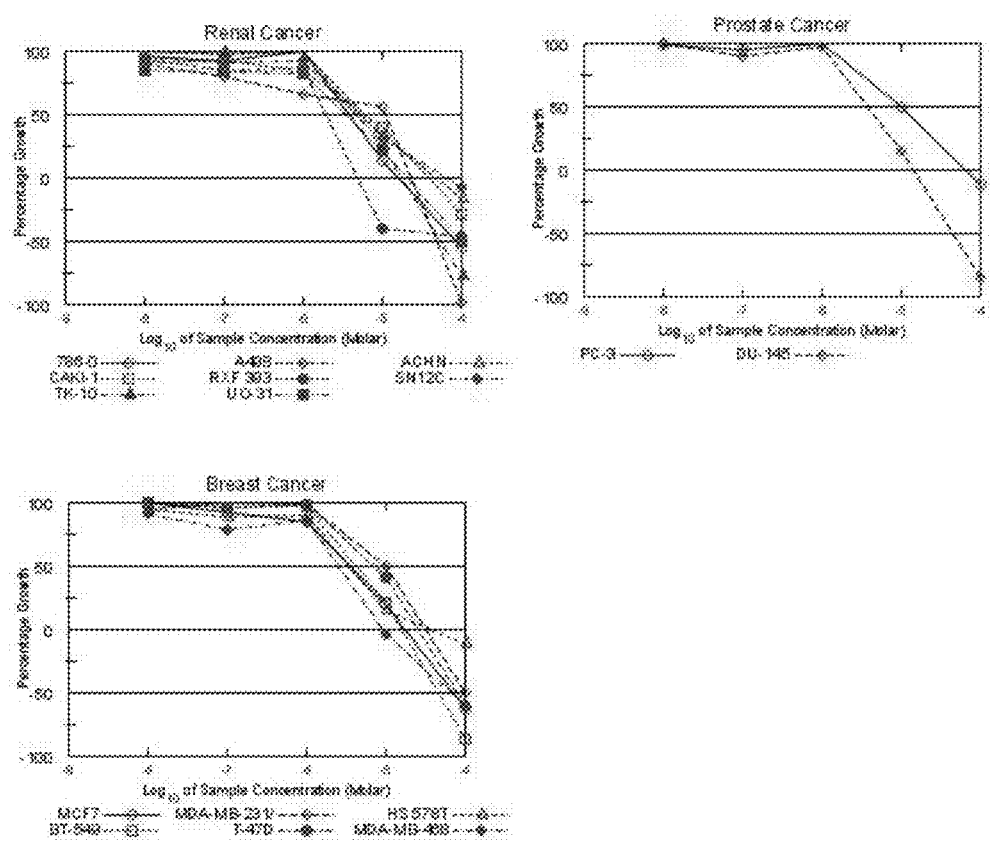
Figure 22:
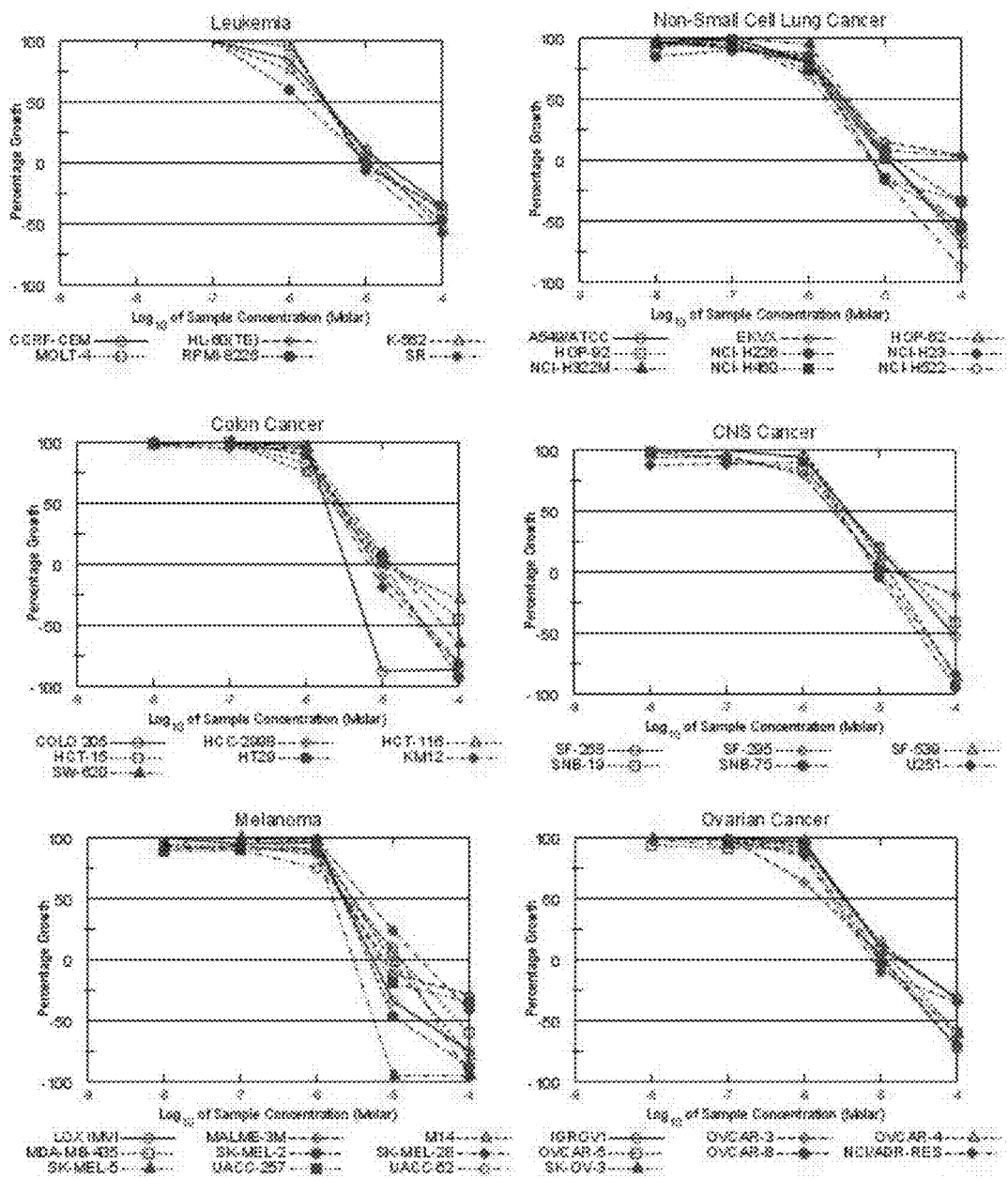
FIG. 22: NIH NCI-60 DTP dose response curves for COH-SR3.
Figure 22:
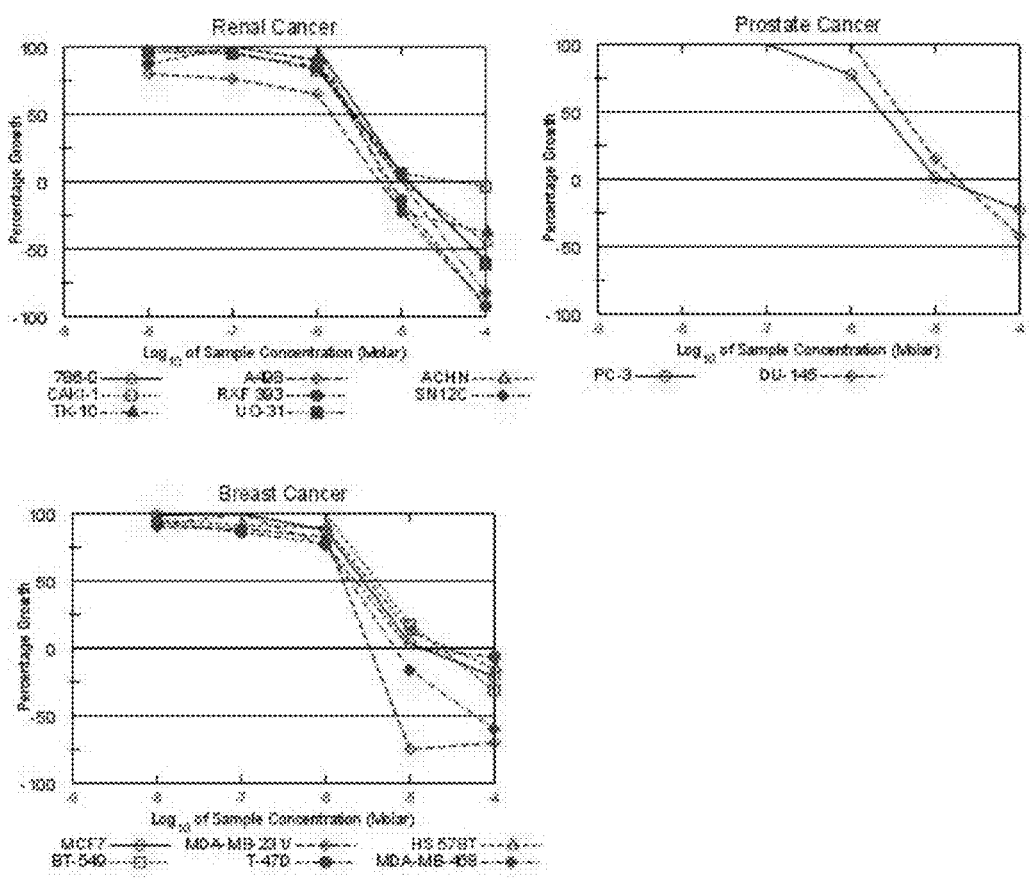
Figure 23:
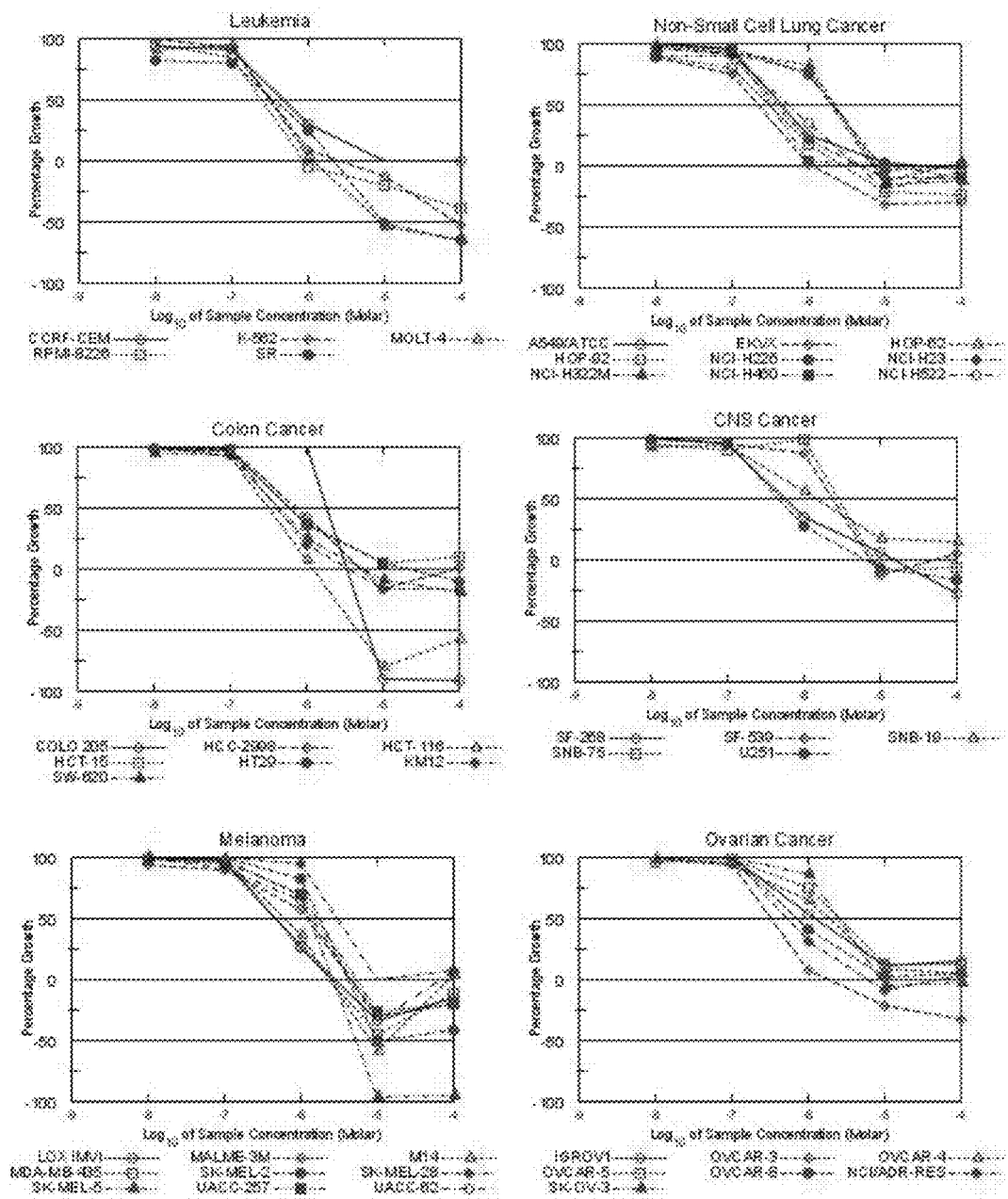
FIG. 23: NIH NCI-60 DTP dose response curves for COH-SR4.
Figure 23:
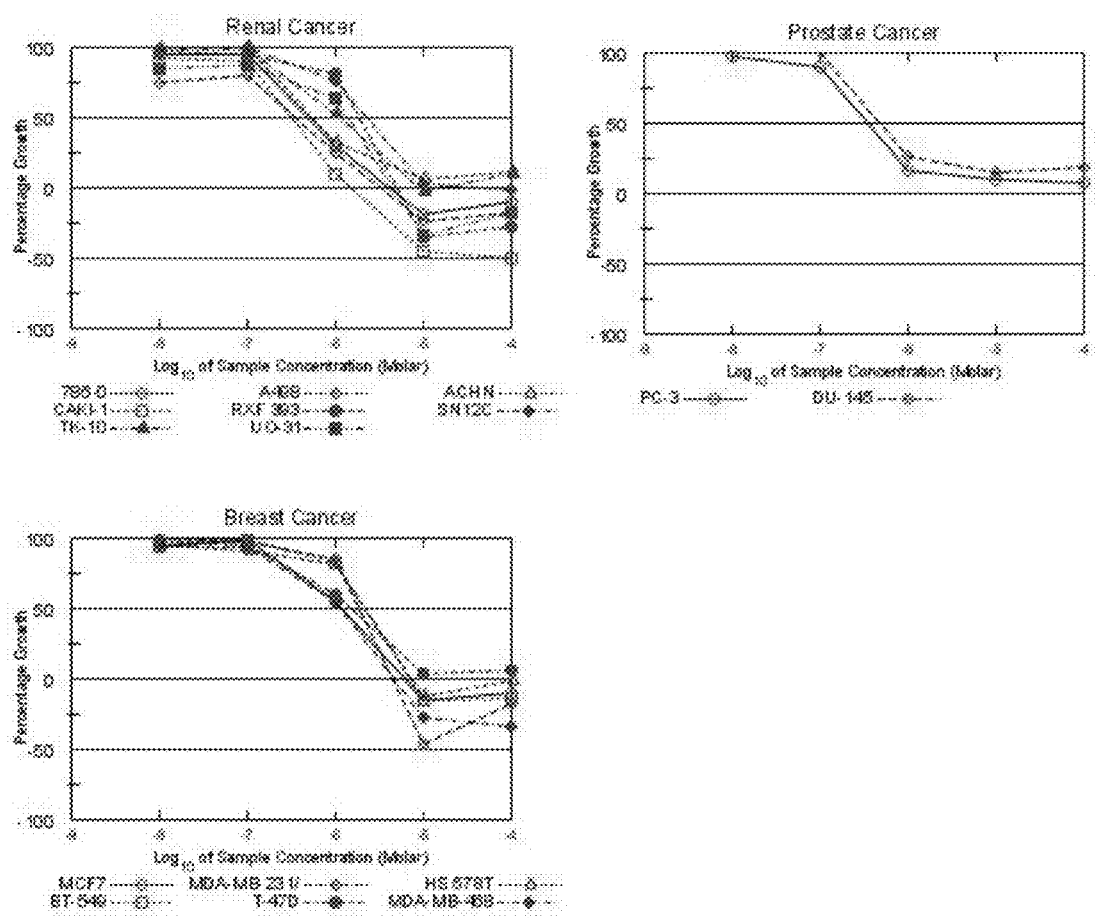
Figure 24:
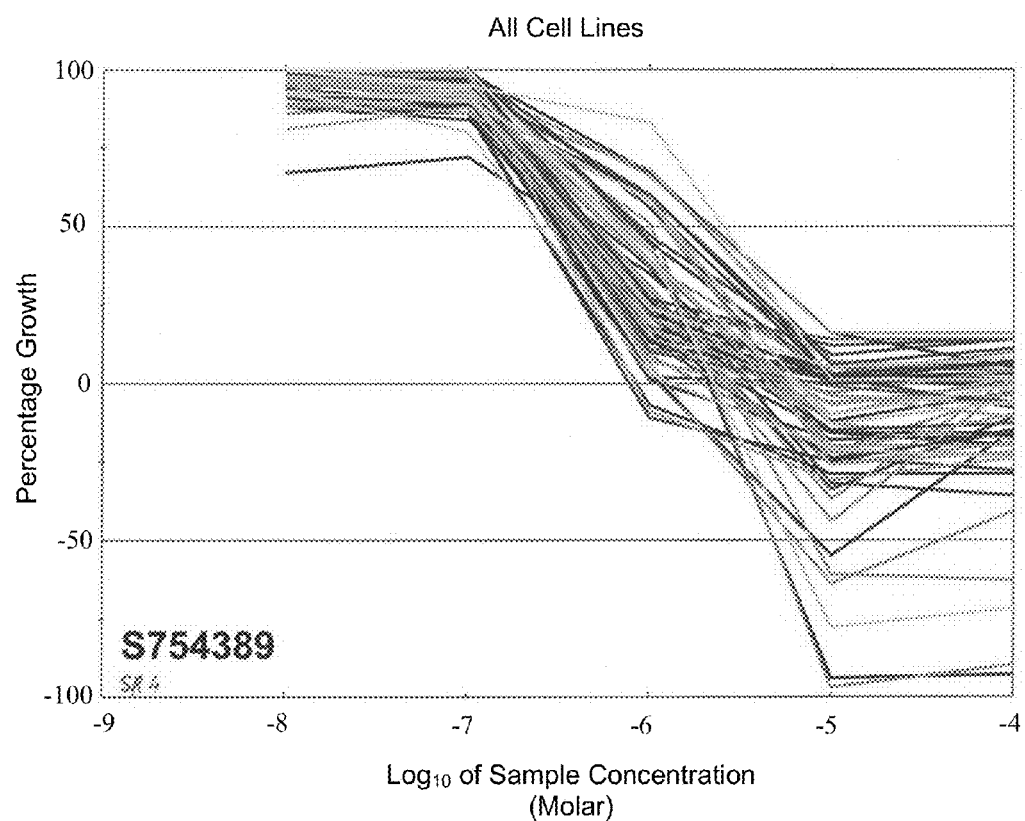
FIG. 24: NIH NCI-60 DTP dose response curves for COH-SR4 shown in one figure.
Figure 25:
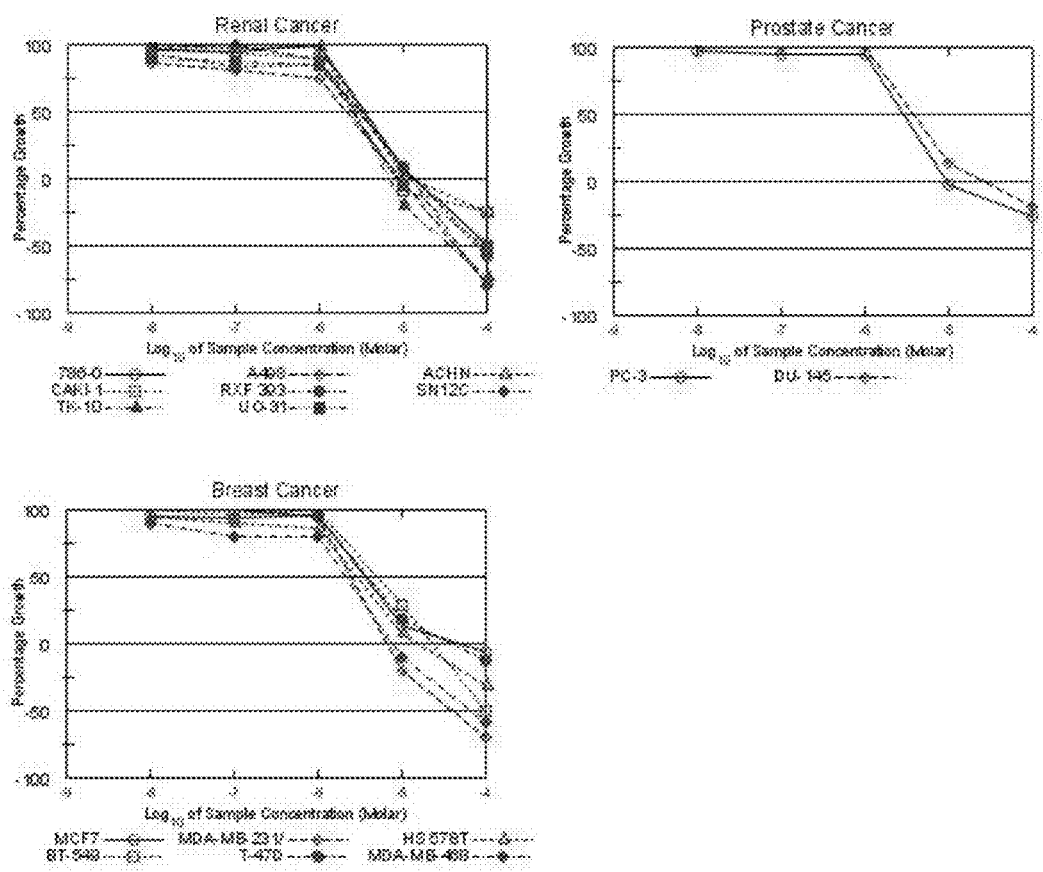
FIG. 25: NIH NCI-60 DTP dose response curves for COH-SR6.
Figure 26:
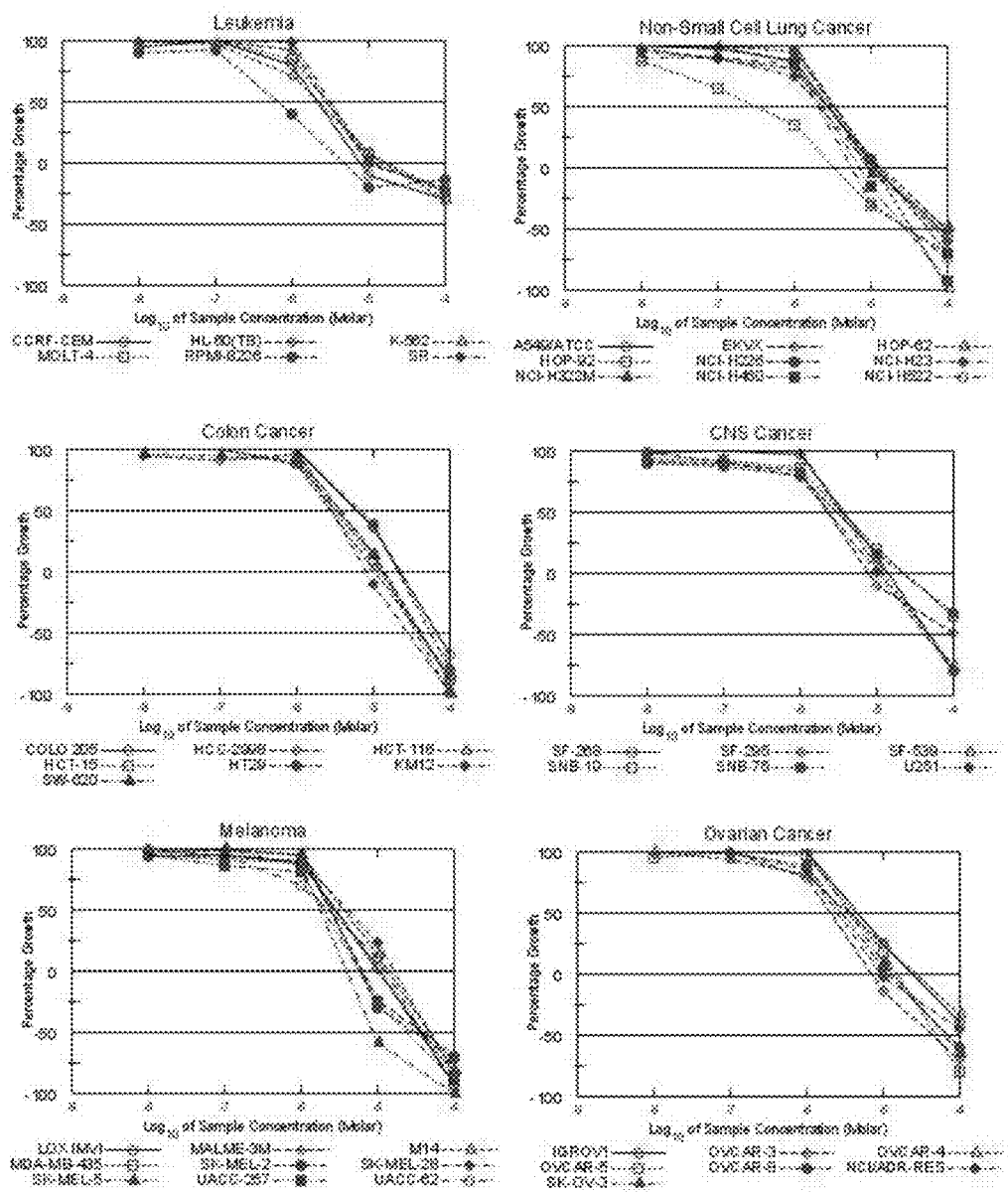
FIG. 26: NIH NCI-60 DTP dose response curves for COH-SR9.
Figure 26:
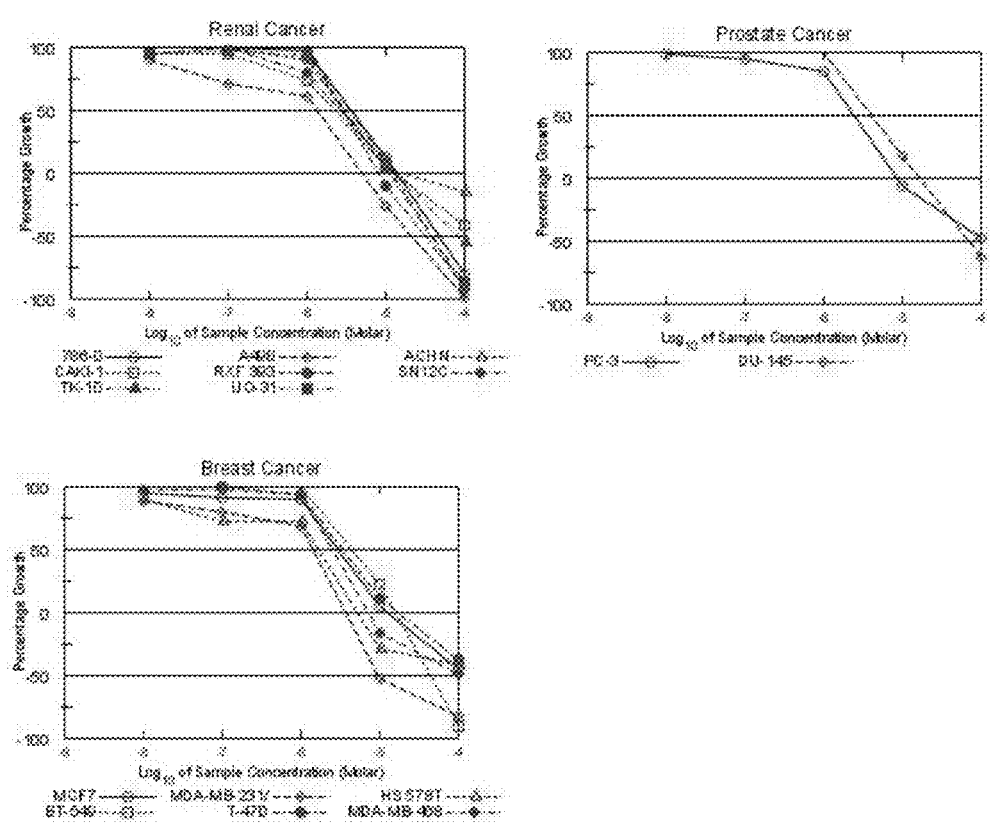
Figure 27:
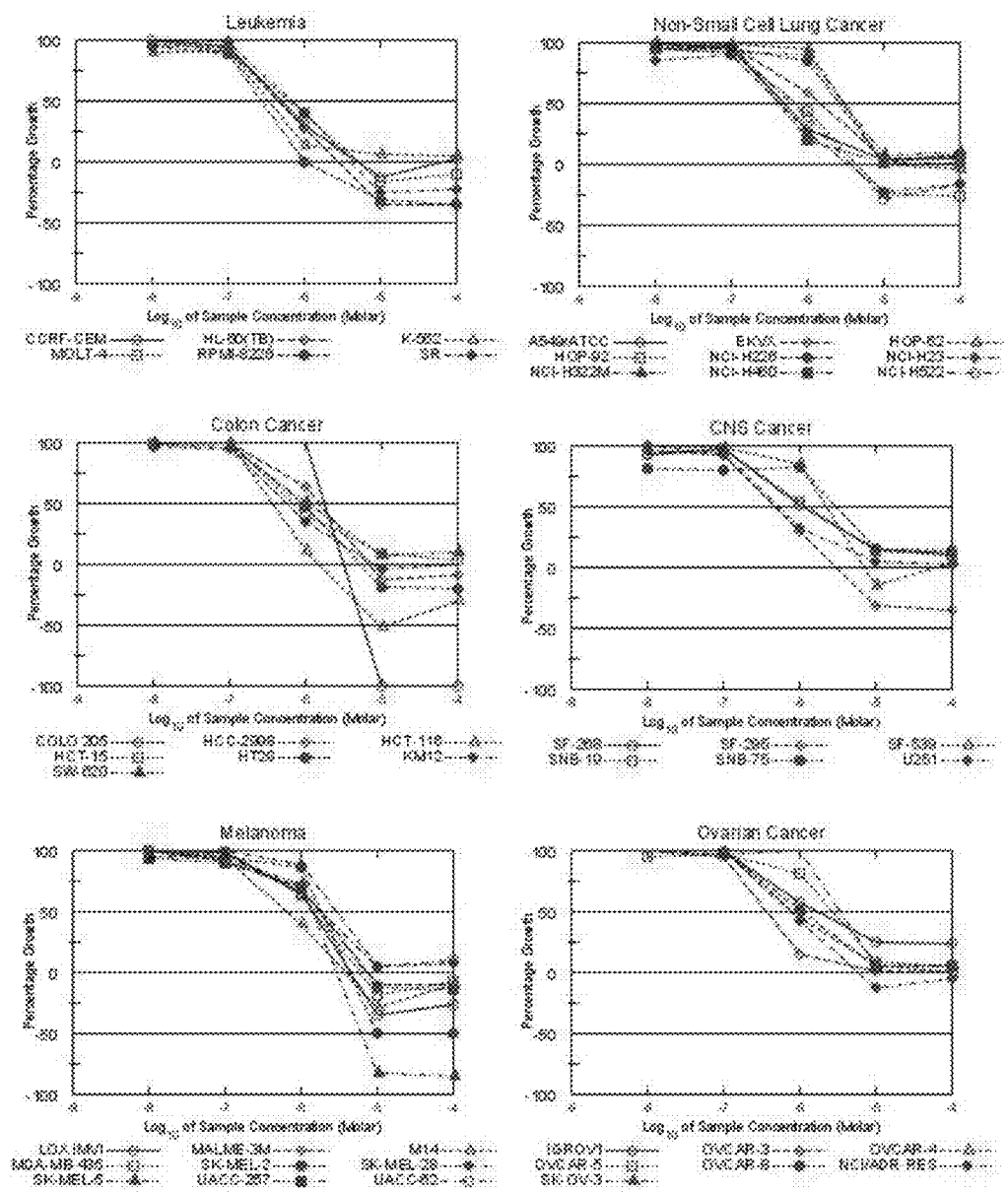
FIG. 27: NIH NCI-60 DTP dose response curves for COH-SR14.
Figure 27:
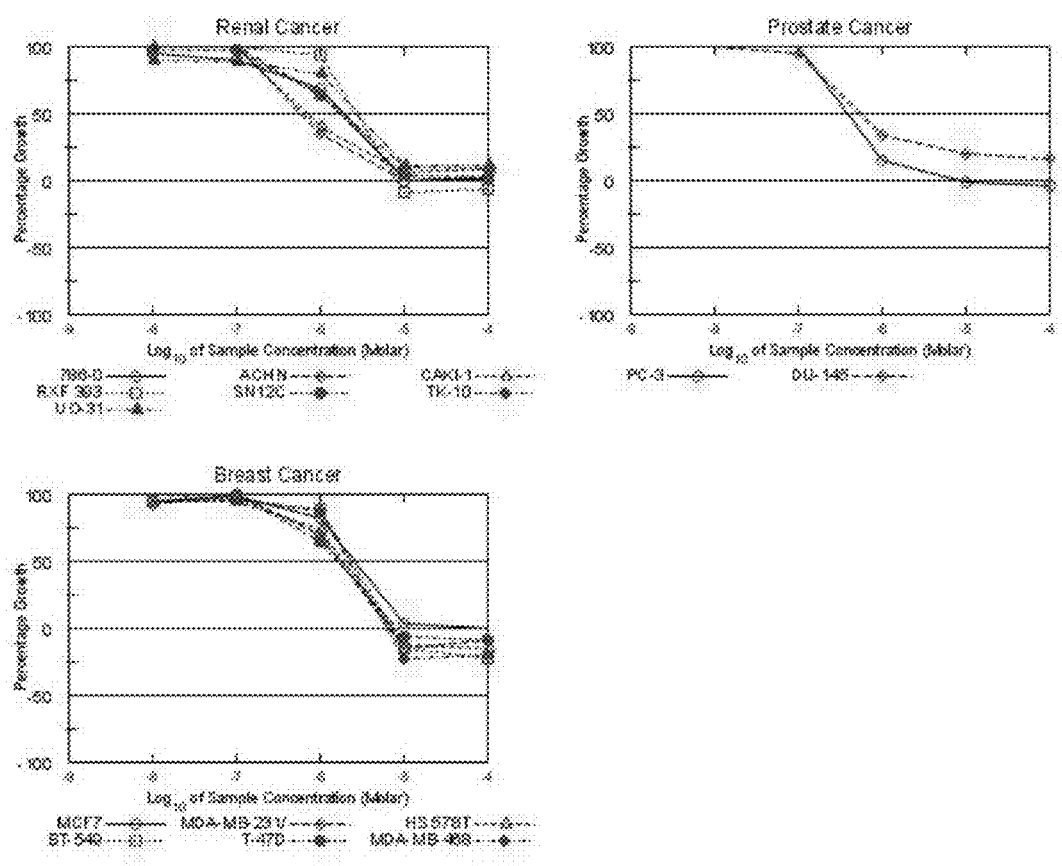

The anti-proliferative and cytotoxic effects of these COH-SR compounds were not only observed in HL-60 amyloid leukemia cells, but was also observed in other types of human cancer lines including leukemia (U937, K-562, MOLT-4), small lung cancer (A549) and breast cancer cells (MCF-7, MDA-MB-231), with $IC_{50}$ of <5 μM after 48-hour treatment (FIG. 19).

Each cancer cells ($2 \times 10^4$) were incubated with a test compound (COH-SR4, or COH-SR9) at various concentrations (0~10 μM) for 48 hours, and the numbers of viable cells were measured by the MTT/XTT assay. Data are expressed as mean±SE from 2 independent experiments with 3 replications each (FIG. 19). Significant anti-proliferative dose-dependent effects of the compounds tested against all cancer cell lines tested were observed (FIG. 19).

Figure 28:
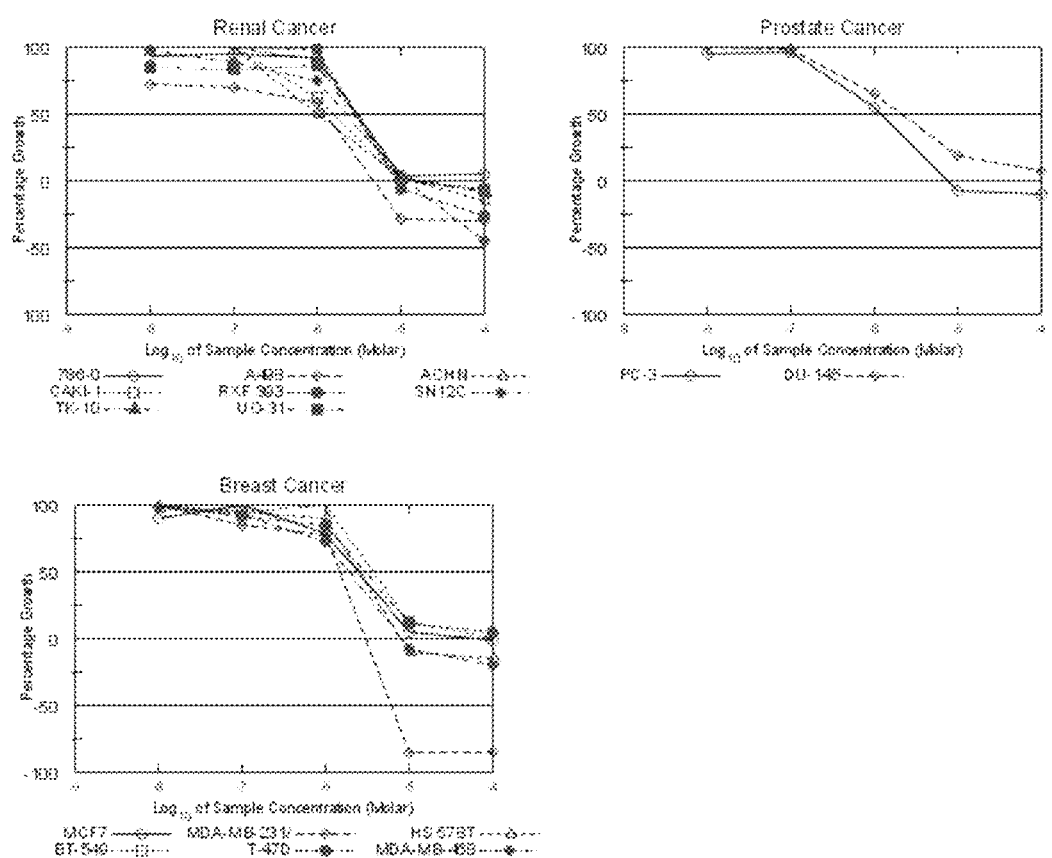
FIG. 28: NIH NCI-60 DTP dose response curves for COH-SR16.

Breast cancer cells MCF-7 or MDA-MB-231 ($1 \times 10^4$ cells) were allowed to proliferate for 1 day and then treated with COH-SR4 or COH-SR9 or nothing for 72 hours. The number of viable cells were measured by MTT assay and shown in FIG. 20. Data expressed as mean±SE from 3 independent experiments Moreover, preliminary data from the NCI-60 DTP Human Tumor Cell Line Drug Screening (http://dtp.nci.nih.gov/branches/btb/ivclsp.html) further confirmed the observations on these COH-SR compounds. Results showed COH-SR compounds (COH-SR2 (FIG. 21), COH-SR3 (FIG. 22), COH-SR4 (FIGS. 23 and 24), COH-SR6 (FIG. 25), COH-SR9 (FIG. 26), COH-SR14 (FIG. 27), and COH-SR16 (FIG. 28)) were active against various leukemia cells lines (C CRF-CEM, HL-60(TB), K-562, MOLT-4, RPMI-8226, and SR), non-small cell lung cancer cell lines (A549/ATCC, EKVX, HOP-62, HOP-92, NCI-H226, NCI-H23, NCI-H322M, NCI-H460, and NCI-H522), colon cancer cell lines (COLO 205, HCC-2998, HCT-116, HCT-115, HT29, KM12, and SW-620), CNS cancer cell lines (SF-268, SF-295, SF-539, SNB-19, SNB-75 and U251), melanoma cell line (LOX IMVI, MALME-3M, M14, MDA-MB-435, SK-MEL-2, SK-MEL-28, SK-MEL-5, UACC-257, and UACC-62), ovarian cancer cell lines (IGROV1, OVCAR-3, OVCAR-4, OVCAR-5, OVCAR-8, NCI/ADR-RES, and SK-OV-3), renal cancer cell lines (786-0, A498, ACHN, CAKI-1, RXF 393, SN12C, TK-10, and UO-31), prostate cancer cell lines (PC-3, and DU-145), and breast cancer cell lines (MCF7, MDA-MB-231, HS 578T, 8T-549, T-47D, and MDA-MB-468). A value of 100 meant no growth inhibition.

A value of 20 meant 80% growth inhibition. A value of 0 meant no net growth over the course of the experiment. A value of −40 meant 40% lethality. A value of −100 meant all cells were dead.

These data suggest that the COH-SR compounds may be used in treating cancers such as leukemia (e.g. acute myeloid leukemia (AML) and monocytic leukemia), lung cancer (e.g. non-small cell lung cancer), colon cancer, CNS cancer, melanoma, ovarian cancer, renal cancer, prostate cancer, and breast cancer.

Example 5

Figure 30:
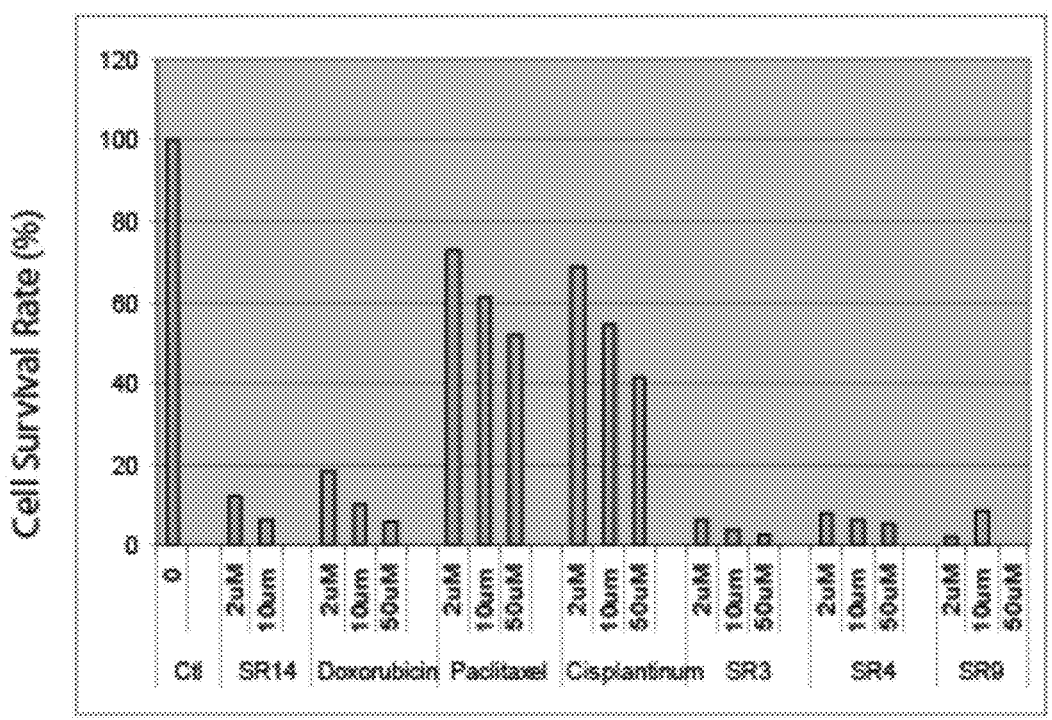
FIG. 30: Effects of COH-SR3, COH-SR4, COH-SR9, COH-SR14, doxorubicin, paclitaxel and cisplatin on viabilities of HMLE breast cancer cells (uM also represents μM in the figure).

COH-SR Compounds Inhibited Growth and Proliferation of Breast Cancer Cell Line 4T1 (a Mouse Mammary Tumor Line) (FIG. 29) and HMLE (Telomerase Immortalized Human Mammary Epithelial Cells) (FIG. 30)

The effects of COH-SR compounds on breast cancer cells were investigated. Cells from 4T1 or HMLE breast cancer cell line were seeded in 96-well plates (about 2000 cells/well), allowed to proliferate for one day, treated with a COH-SR compound, doxorubicin, paclitaxel, cisplatin, or nothing (control) at a specific dose (3 wells for each treatment) and assayed for cell viability 3 days after using DIMSCAN assay. COH-SR3, COH-SR4, COH-SR9, doxorubicin, paclitaxel, and cisplatin were used at a dosage of 40 nM, 200 nM, 1 μM, 2 μM, 10 μM, or 50 μM for 4T1 breast cancer cell lines. COH-SR14 was used at a dosage of 40 nM, 200 nM, 1 μM, 2 μM, or 10 μM for 4T1 breast cancer cell lines. COH-SR3, COH-SR4, COH-SR9, doxorubicin, paclitaxel, and cisplatin were used at a dosage of 2 μM, 10 μM, or 50 μM for HMLE breast cancer cell lines. COH-SR14 was used at a dosage of 2 μM, or 10 μM for HMLE breast cancer cell lines. COH-SR3, COH-SR4, COH-SR9 and COH-SR14 showed similar or better cytotoxic effects on 4T1 breast cancer cell lines compared with current anti-cancer drugs such as doxorubicin, paclitaxel and cisplatin (FIG. 29). COH-SR3, COH-SR4, COH-SR9 and COH-SR14 showed more potent cytotoxic effects on 4T1 breast cancer cell lines compared with current anti-cancer drugs such as doxorubicin, paclitaxel and cisplatin (FIG. 30).

Example 6

Figure 31:
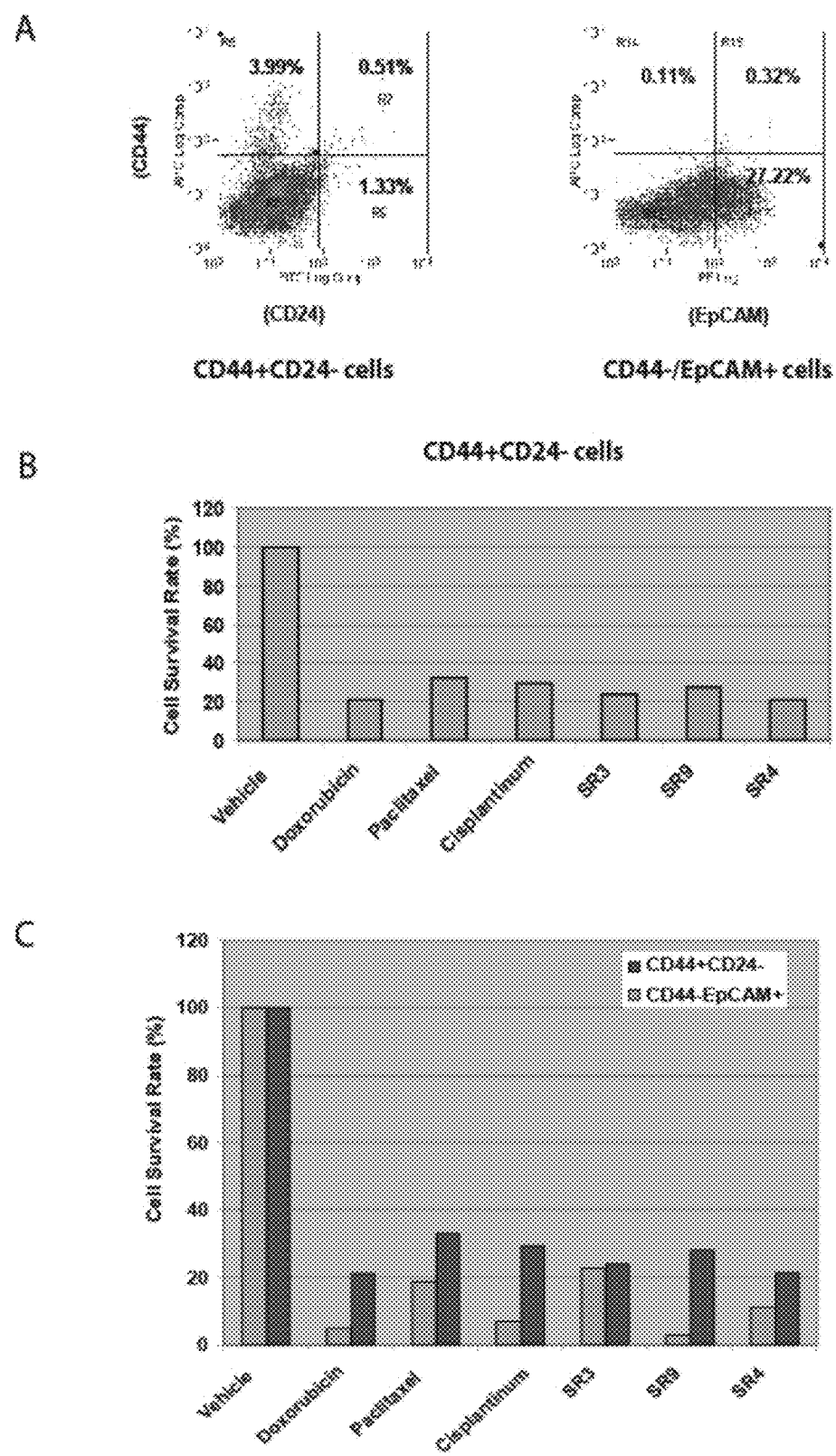
FIG. 31: Effects of 20 μM COH-SR3, COH-SR4, COH-SR9, doxorubicin, paclitaxel or cisplatin on viabilities of CD44+CD24− cancer stem cells in breast tumor and CD44−/EpCAM+ regular breast cancer cells. (A) FACs analysis for identification of CD44+CD24− cancer stem cells in breast tumor and CD44−/EpCAM+ regular breast cancer cells; (B) effects of COH-SR3, COH-SR4, COH-SR9, doxorubicin, paclitaxel or cisplatin on viabilities of CD44+CD24− cancer stem cells in breast tumor; and (C) effects of COH-SR3, COH-SR4, COH-SR9, doxorubicin, paclitaxel or cisplatin on viabilities of CD44+CD24− cancer stem cells in breast tumor and CD44−/EpCAM+ regular breast cancer cells.

COH-SR Compounds Inhibited Growth and Proliferation of Breast Cancer Stem Cell (BCSC) (CD44+CD24−) (FIGS. 31 and 32)

Xenograft preparations from NOD/SCID mice were performed to generate BCSC (CD44+CD24−) using patient tumor specimens derived from primary breast cancer tumors previously exposed to neoadjuvant chemotherapy. Identifications of BCSC (CD44+CD24−) and regular breast cancer cells (CD44−EpCAM+) were performed by FACS analysis (FIG. 31(A)).

Cells of BCSC (CD44+CD24−) or regular breast cancer cells (CD44−EpCAM+) were isolated and cultured for several passages, and then treated with 20 μM of a COH-SR compound (COH-SR3, COH-SR4, or COH-SR9), or 20 μM of a known anti-cancer drug (adriamycin, paclitaxel or cisplatin) or nothing for 72 hours. Cell survival rates (%) were calculated from MTT assay with triplicate wells for each treatment. COH-SR3, COH-SR4 and COH-SR9 showed a similar or better effect on inhibition of cell growth of BCSC cells (FIGS. 31B and 31C) and regular breast cancer cells CD44−/EpCAM+ (FIG. 31C), but the effects on cell growth of BCSC cells and regular breast cancer cells were different (FIG. 31C).

Cells of BCSC (CD44+CD24−) or regular breast cancer cells (CD44−EpCAM+) were isolated from breast tumor or brain metastasis and cultured for several passages, and then treated with 20 μM of a COH-SR compound (COH-SR4, COH-SR9, or COH-SR14), or 20 μM of a known anti-cancer drug (adriamycin, paclitaxel or cisplatin) or nothing for 72 hours. Cell survival rates (%) were calculated from MTT assay with triplicate wells for each treatment. The results showed that COH-SR4, COH-SR9 and COH-SR14 showed a similar or better effect on inhibition of cell growth of BCSC cells and regular breast cancer cells CD44−/EpCAM+, but the effects on cell growth of BCSC cells and regular breast cancer cells were different (FIGS. 32A and 32B).

Example 7

Effects of COH-SR4 in Ovarian Cancer Cells (FIG. 33)

(A) COH-SR4 Showed Toxicity Against Ovarian Cancer Cells (e.g. SKOV3, MADH2744, and A2780 DPPr) (FIG. 33A).

SKOV3 is a cisplatin resistant human ovarian cancer cell line. Human ovarian cancer cells (SKOV3, MADH2744, and S2780 DPPr) were incubated with COH-SR4 at various concentrations (0~10 μM) or without COH-SR4 for 48 hours. Cells Viabilities were determined by measuring cellular acid phosphatase activities. Data were represented as a ratio to vehicle (DMSO) control. Data showed a dose-dependent cytotoxicity and anti-proliferative effects of COH-SR4 on both regular and cisplatin-resistant ovarian cancer cells.

(B) COH-SR4 Inhibited Phosphorylation of Stat3 Protein and HIF-1α Protein Expression in SKOV3 Cells (FIG. 33B).

SKOV3 cells were incubated with various concentrations of COH-SR4 (1~10 μM) for 24 hours. Whole-cell lysates were analyzed by immunoblotting with antibodies against phosphorylated and total form of Stat3, Akt and MAPK, and HIF-1α. GAPDH was used as a loading control. The results showed that COH-SR4 inhibited phosphorylation of Stat3 protein and HIF-1α protein expression in SKOV3 cells (FIG. 33B).

Example 8

Effects of COH-SR4 on Brain Cancer (Glioma Cells)

Figure 34:
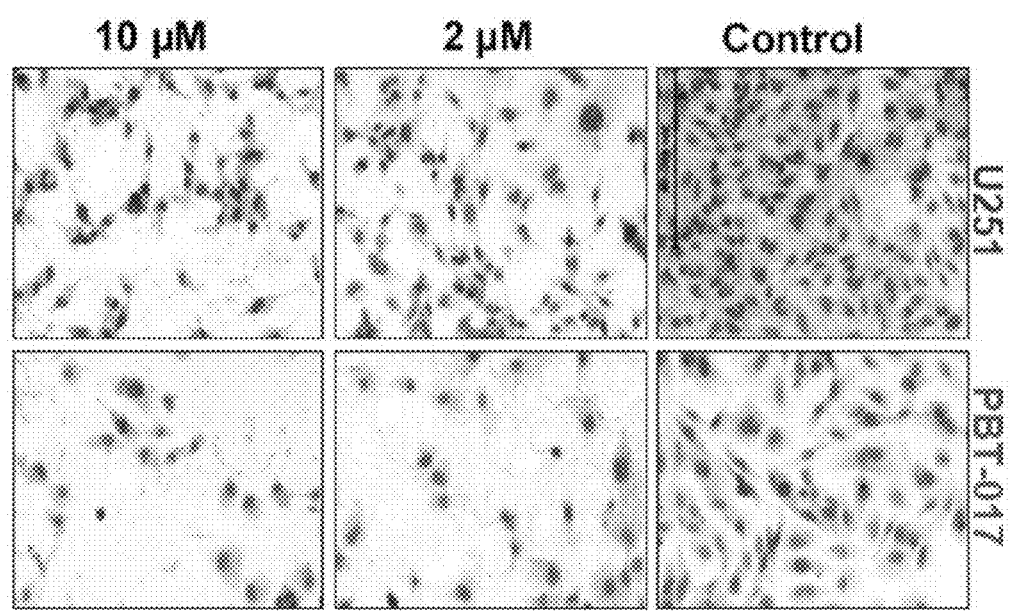
FIG. 34: (A) Effects of COH-SR4 in U251, U87, PBT-017, PBT018, PBT003 and PBT028 glioma cell lines; (B) Effects of COH-SR4 in U251, U87, PBT-017, and PBT003 glioma cell lines; and (C) COH-SR4 was cytotoxic to U251, and PBT-017 glioma cell lines, wherein scale bar applies to all images (uM also represents μM in the figures).

(A) COH-SR4 Showed Toxicity Against Glioma Cell Lines (e.g. U251, U87, PBT-017, PBT018, PBT003 and PBT028) (FIG. 34A and FIG. 34B).

Cells of each cell line (U251, U87, PBT-017, PBT018, PBT003 and PBT028) were treated with various concentrations (0~100 μM) of COH-SR4 for 72 hours. Cell viabilities were determined by ATP viability assays. Data were represented as a ratio to vehicle (DMSO) control, and plotted as mean±SEM (n=12) obtained from 2-3 experiments (FIG. 34A).

Cells of each cell line (U87, U251, PBT003 and PVT-017) were treated with various concentrations (0~100 μM) of COH-SR4 for 72 hours. Cell viabilities were determined by ATP viability assays. Data were represented as a ratio to vehicle (DMSO) control, and plotted as mean±SEM (n=12) obtained from 2~3 experiments (FIG. 34B).

The $IC_{50}$ of killing each glioma cancer cell lines are summarized in Table 1:

TABLE 1

$IC_{50}$ of COH-SR4 on Glioma Cancer Cell Lines U251, U87, PBT-017, PBT018, PBT028 and PBT003

| | Glioma Cell Line | | | | | |
|---|---|---|---|---|---|---|
| | U251 | U87 | PBT-017 | PBT018 | PBT028 | PBT003 |
| $IC_{50}$ (μM) | 2.1 | 2.8 | 2.0 | 6.5 | 2.0 | 1.5 |

(B) COH-SR4 was Cytotoxic to Glioma Cells U251 and PBT-017 (FIG. 34C).

Cells of glioma U251 cell line or PBT-017 cell line were incubated with COH-SR4 of 2 μM or 10 μM, or without any treatment for 48 hours, and then examined for morphologic changes by Giemsa-Wright stain. The results were observed microscopically and shown in FIG. 34C. All pictures in FIG. 34C were shown with the same magnification. The cell numbers in glioma cells treated with COH-SR4 decreased compared to cells not treated (FIG. 34C).

(C) Higher Doses of COH-SR4 Showed Faster Killing in Glioma Cells (FIG. 35).

Glioma cells U251 (FIG. 35A) and PBT-017 (FIG. 35B) were treated with COH-SR4 having a concentration of 0 μM, 2 μM, 3 μM, or 4 μM and analyzed by the same protocol described supra. Cell viabilities were determined by ATP viability assays. Data were represented as a ratio to untreated control, and plotted as mean±SEM (n=12) obtained from 2~3 experiments. The results showed that higher doses of COH-SR4 killed the glioma cells faster.

Figure 36:
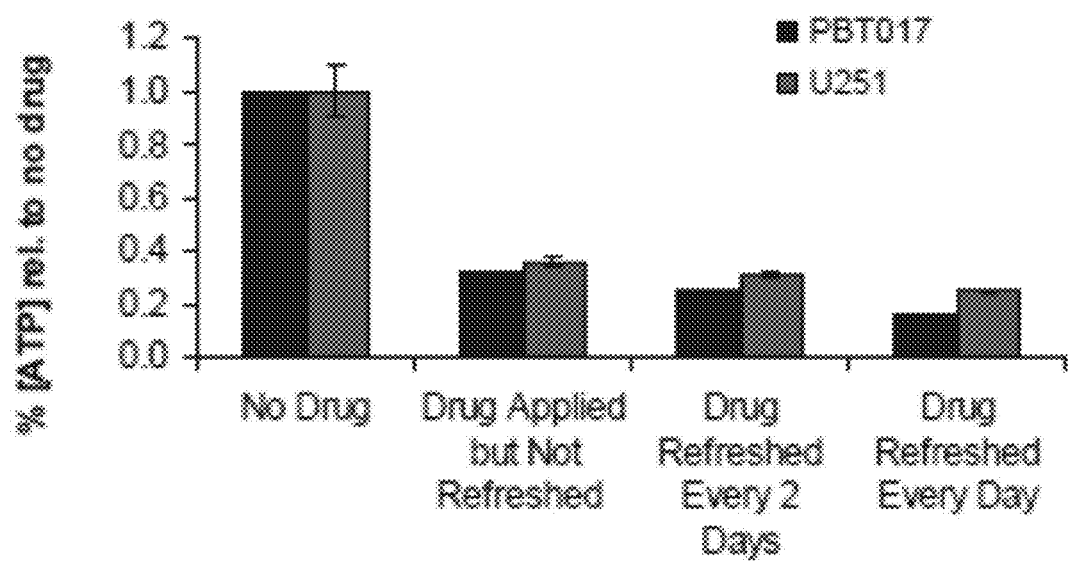
FIG. 36: Treatments of COH-SR4 showed improved killing in glioma cells U251 and PBT-017 when the drugs applied were refreshed.

(D) Treatments of COH-SR4 Showed Improved Killing in Glioma Cells U251 and PBT-017 when the Drugs Applied were Refreshed. (FIG. 36).

Glioma cells U251 and PBT-017 were treated with COH-SR4 with no refreshment of the drug, with refreshment of the drug every 2 days or with refreshment of the drug every day, or without any treatment. The resulting cells were analyzed by the same protocol described supra after treatment of. Data were represented as a ratio to untreated control, and plotted as mean±SEM (n=12) obtained from 2~3 experiments. The results showed that refreshment of the COH-SR4 applied killed the glioma cells faster.

(E) COH-SR4 Induced Apoptosis of Glioma Cells (FIG. 37).

PBT-017 glioma cells were incubated with nothing (control), DMSO, and COH-SR4 at 2 μM or 10 μM for 4 days. The absolute cell number of the healthy cells, apoptotic cells and necrotic cells were measured and summarized in FIG. 37.

Treatment of COH-SR4 decreased absolute cell numbers of PBT-017 glioma cells (FIG. 37A). Furthermore, treatment of COH-SR4 increased the fraction of apoptotic cells in the remaining PBT-017 glioma cells (FIG. 37B).

Figure 38:
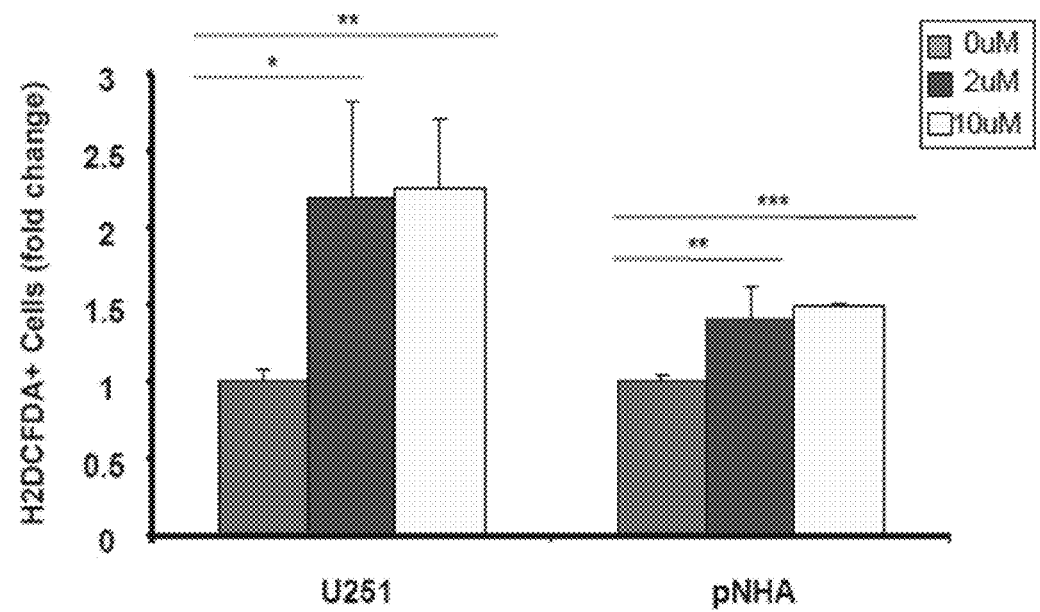
FIG. 38: Effects of COH-SR4 on H2DCFDA+ cells in glioma cells U251 compared to normal human astrocytes (pNHA) cells (uM also represents μM in the figures, "*"

(F) Treatment of COH-SR4 Generated Intracellular ROS in Glioma Cells (FIG. 38).

Cells of U251 glioma cells or pNHA cell lines were treated with COH-SR4 at a concentration of 0 μM, 2 μM or 10 μM for 24 hours before intracellular ROS was assessed by flow cytometry (representative of 3 runs and samples in triplicate). ROS increased in the glioma cells treated with COH-SR4 as indicated by the increased amounts of H2DCFDA+ cells (FIG. 38).

(G) Effects of Dosages of COH-SR4 on CD133 Sorted PBT-017 Glioma Cell Line (FIG. 39A).

CD133 positive glioma stem cells were sorted by FACS. Unsorted cells, CD133 positive cells, and CD133 negative PBT-017 glioma cells were treated with COH-SR4 at various concentrations (0~100 µM) for 4 days, respectively. Data were represented as a ratio to untreated control, and plotted as mean±SEM (n=12) obtained from 2~3 experiments (FIG. 39A). The results showed that COH-SR4 was effective in killing the CD133 positive glioma stem cells as well as the unsorted and CD133 negative glioma cells.

(H) Effects of Dosages of COH-SR4 on PI Positive Cells in U251 Glioma Cell Line (FIG. 39B).

Cells of U251 glioma cells or pNHA cell lines were treated with COH-SR4 at a concentration of 2 µM or 10 µM for four days. The amounts of PI positive (dead) cells were assessed by flow cytometry (representative of 3 runs and samples in triplicate) (FIG. 39B). There was no significant difference in PI positive cells between pNHA and glioma cells without treatment.

(I) COH-SR4 Inhibited HIF-1α Protein Expression in U251 Cells (FIG. 40)

U251 cells were incubated with various concentrations of COH-SR4 (1~10 µM). Whole-cell lysates were analyzed by immunoblotting with antibodies against HIF-1α. GAPDH was used as a loading control. The results showed that COH-SR4 inhibited HIF-1α protein expression in U251 cells (FIG. 40).

(J) COH-SR4 Inhibited Luciferase Expression of VEGF Protein in U251 Cells (FIG. 41).

U251 cells expressing luciferase reporter containing human VEGF promoter were incubated with various concentrations of COH-SR4 (0, 1, or 3 µM) for 24 hours. Luciferase activity was determined and normalized to the cell number for each treatment. Data were represented as a ratio to vehicle control that was treated by DMSO. The results showed that COH-SR4 inhibited luciferase expression of VEGF protein in U251 cells (FIG. 41).

(K) COH-SR4 Inhibited Luciferase Expression Driven by HRE Promoter in U251 Cells Under Both Normoxic and Hypoxic Conditions (FIG. 42).

U251 cells were transfected with plasmids expressing luciferase reporter genes driven by a HRE reporter plasmid containing five copies of the HRE site (5×HRE). Transfected cells were then incubated with COH-SR4 at various concentrations (0, 1, or 3 µM) for 24 hours and assayed for luciferase activities. Data were represented as a ratio to vehicle control that was treated by DMSO. The results showed that COH-SR4 inhibited luciferase expression driven by HRE promoter in U251 cells under both normoxic and hypoxic conditions (FIG. 42).

Example 9

Effects of COH-SR4 and TMZ on Glioma Cells PBT-017 and U251 (FIG. 43)

Cells of each cell line were treated with various concentrations (0~100 µM) of COH-SR4 or various concentrations (0~1000 µM) of TMZ for 72 hours. Cell viabilities were determined by ATP viability assays. Data were represented as a ratio to untreated cells as control, and plotted as mean±SEM (n=12) obtained from 2-3 experiments (FIG. 43).

The $IC_{50}$ of TMZ and COH-SR4 for each glioma cancer cell lines are summarized in Table 2: Table 2 also includes $IC_{50}$ of other chemotherapy drugs such as 5-FU, CPT-11 and 7-ethyl-10-hydroxy-camptothecin (SN-38, an active metabolite of CPT-11) for glioma cancer cell obtained using the protocol described supra.

TABLE 2

| $IC_{50}$ of COH-SR4 and TMZ on Glioma Cancer Cell Lines U251, and PBT-017 | | |
|---|---|---|
| Glioma Cell Line | U251 | PBT-017 |
| $IC_{50}$ of TMZ (µM) | 371 | 13 |
| $IC_{50}$ of COH-SR4 (µM) | 2 | 2.1 |
| $IC_{50}$ of 5-FU (µM) | 61 | — |
| $IC_{50}$ of CPT-11 (µM) | 41.1 | — |
| $IC_{50}$ of SN-38 (µM) | 0.04 | — |

Thus, COH-SR4 showed higher cytotoxicity potency toward glioma cells compared to TMZ and other chemotherapy drugs 5-FU and CPT-11.

Example 10

COH-SR4 Showed Synergism with a Chemotherapy Drug (e.g. TMZ, SN38, CPT-11, or 5-FU) in Treating Glioma Cells PBT-017 and/or U251 (FIGS. 44~47)

Effects of combination of COH-SR4 and a chemotherapy drug such as TMZ, SN38, CPT-11, and 5-FU were studied by combination index (CI) theorem and plot using the method described in Chou ("Experimental Design, and Computerized Simulation of Synergism and Antagonism in Drug Combination Studies," Pharmacological Reviews, Vol. 58, No. 3), which is incorporated herein by reference in its entirety. For a two-drug combination, a CI of less than 1 showed a synergistic effect of the two drugs, a CI of 1 showed an additive effect of the two drugs, and a CI of more than 1 showed an antagonistic effect.

COH-SR4 and a chemotherapy drug (TMZ, SN38, CPT-11, or 5-FU) were dissolved in DMSO individually, and then diluted to the appropriate concentration in the same cell culture media before applying to cells of each cell line. After 4 days, the amount of ATP present in the cell lysates were assessed using Progema's CellGlo kit. The CI of each combination of COH-SR4 and the chemotherapy drug was calculated and plotted against the concentration of COH-SR4 for each concentration of the chemotherapy drug used.

The combination indexes of combinations of COH-SR4 and TMZ, SN38, or CPT-11 in U251 glioma cells are shown in FIG. 44A, FIG. 45A, and FIG. 46, respectively. Synergism were observed for COH-SR4 at a concentration of less than 0.5 µM and low concentration of TMZ (12.5 µM), SN-38 (<0.001 µM), or CPT-11 (<0.125 µM). Additive effects were observed for COH-SR4 at a concentration of higher than 0.65 µM and TMZ at a concentration of 100 µM, for COH-SR4 at a concentration of higher than 0.5 µM and SN-38 at a concentration of less than 0.003 µM, and for COH-SR4 at a concentration of higher than 0.675 µM and CPT-11 at a concentration of higher than 0.5 µM.

The combination index of COH-SR4 and TMZ, SN38, or CPT-11 in PBT-017 glioma cells are shown in FIG. 44B, FIG. 45B, FIG. 47, respectively. Synergism were observed for COH-SR4 at a concentration of less than 0.5 µM and low concentration of TMZ (25 µM), SN-38 (<0.0004 µM), or CPT-11 (<0.0625 µM). Additive effects were observed for COH-SR4 at a concentration of less than 1.0 µM and TMZ at a concentration of higher than 100 µM, for COH-SR4 at a concentration of higher than 0.5 µM and SN-38 at a concentration of less than 0.001 µM, for COH-SR4 at a concentration of higher than 1.0 µM and CPT-11 at a concentration of less than 0.5 µM, and for COH-SR4 at a concentration of less than 0.05 µM and 5-FU at a concentration of higher than 250 µM.

CI studies of COH-SR4 and 5-FU showed synergism for COH-SR4 at concentration of less than 0.5 µM and 5-FU at a concentration of less than 125 µM.

Thus, the results showed that small amounts of COH-SR4 may be useful to increase the therapeutic effect of another anticancer drug such as TMZ, SN38, CPT-11 and 5-FU.

Example 11

COH-SR4 is a Substrate for GSTP

Prokaryotic Expression of GSTP The cDNA of GSTP was cloned into the prokaryotic expression plasmid vector, pET30a(+) (Novagen), creating the GSTP-pET30a(+) plasmid free of extraneous sequences. Bam H1 and XhoI restriction sites were used for cloning. This plasmid was transfected into E. coli BL21 (DE3). Protein was expressed in E. coli BL21 (DE3) grown at 37° C. Once the $OD_{600}$ reached 0.6 protein was induced with 0.4 mM IPTG.

Purification of Recombinant GSTP All purification steps were carried out at 4° C. unless otherwise specified. All buffers were prepared fresh and filter sterilized. Briefly, bacteria was lysed in 10 mM K-$PO_4$ buffer pH 7.0 containing 1.4 mM β-mercaptoethanol (Buffer A) and 100 µM PMSF followed by sonication at 50 rpm for 3 times at 30 sec each. After incubation in the above buffer for 4 hours with gentle shaking lysate was centrifuges at 28,000×g for 45 min at 4° C. and the supernatant was collected for GSH-affinity chromatography. GSH-affinity resin (i.e., epoxy-activated Sepharose 6B) was equilibrated with 22 nM K-$PO_4$ buffer, pH 7.0 containing 1.4 mM β-mercaptoethanol (Buffer B). The supernatant was mixed with GSH-affinity resin for coupling for overnight at 4° C. The unbound proteins were washed with Buffer B until OD at 280 nm is zero. Bound protein (purified GSTP) was eluted with 50 mM Tris-HCl, pH 9.6 containing 1.4 mM β-mercaptoethanol. Elutes protein was dialyzed against Buffer A for overnight and the GSTP protein concentration was checked by Bradford's assay.

FIG. 48 shows the formation of COH-SR4 and GSH conjugate (GSR4) in the presence of GSTs.

1-Chloro-2,4-dinitrobenzene (CDNB) is a known substrate of GST-P. Reaction of CDNB and GSH in the presence of GST-P forms a conjugate S-(2,4-dinitrophenol)-glutathione (DNP-SG) (Awasthi, Y. C. et al., Blood, 58: 733-738, 1981, incorporated herein by reference in its entirety).

15 mM GSH in 5 ml of 100 mM K-$PO_4$, pH 7.0 was prepared, degassed by bubbling with nitrogen for about 30 seconds, and added 5 U purified GSTP to provide a GSH-GSTP solution. CDNB (400 mM in 250 µL ethyl alcohol) was added slowly drop-by-drop into the GSH-GSTP solution with stirring in dark to provide a reaction mixture. The reaction mixture was degassed by bubbling with nitrogen for about 30 seconds, and stirred at room temperature in dark for about 12 hours. The reaction mixture was then lyophilized into reaction pellet. The reaction pellet (about 95% DNP-SG, with traces of oxidized glutathione (GSSG)) was washed twice with ethyl alcohol and reconstituted in $dH_2O$ (about 100~200 µL).

The similar protocol was used in preparing GSR4 by replacing CDNB with COH-SR4 (2 mM/250 µL ethanol solution prepared from 20 mM COH-SR4 in DMSO).

The TLC was run in a TLC silica plate (Whatman, 250 µm) in a TLC solvent of 7 part acetonitrile and 2 part $dH_2O$ for about 60 minutes. The TLC was visualized by spraying the TLC plate with ninhydrin (FIG. 49).

Lane 1 in the figure showed GSH; lane 2 showed CDNB; lane 3 showed COH-SR4; lane 4 showed DNP-SG as an example of GSH conjugate; and lane 5 showed that the GST-P catalyzed reaction of COH-SR4 and GSH formed a conjugate, GSR4.

UV-VIS spectrums of COH-SR4 and GSR4 were obtained in the wavelength of 800-200 nm. The peaks at the 340 nm were characteristics of GSR4 (at 10, 20 or 50 µM in 10 mM phosphate buffer) compared to COH-SR4 (10 µM in 10 mM phosphate buffer) (FIG. 50).

Furthermore, COH-SR4 significantly decreased the amount of GSH, which coincided with the formation of the conjugate GSR4 in a cell-free system (FIG. 51). A reaction system having 50 µM GSH, 50 µM COH-SR4 and 10 µL GSTP was prepared (Thangasamy, T. et al., Nutrition and Cancer, 59(2), 258-268, which is incorporated herein by reference). Aliquots were removed from the reaction system after certain reaction time (0~10 min) and added into 5,5' dithiobis 2-nitrobenzoic acid (DTNB). Then UV-VIS spectrophotometers of the reaction aliquots were obtained. Visible absorption spectrum showed consumption of COH-SR4 (~415 nm, COH-SR4 with DTNB) and increased amount of GSR4 (~340 nm) as reaction time increased from about 0 min (the first spectrum from the top) to about 10 min (the first spectrum above the buffer spectrum, the spectrums in between (from the top to the bottom) were reaction mixtures having increasing reaction times).

FIG. 52 showed kinetics of GST-P using COH-SR4 as a substrate, and the $K_m$ is 40 µM. Reaction systems were prepared by mixing COH-SR4 (50 µL, various final concentrations of 0~10 µM), 100 µL of 10 mM GSH (GSH solution in GST assay buffer, pH 6.5), 10 µL of GSTP enzyme (0.52 mg/mL) and having 840 µL GST assay buffer (100 mM K-$PO_4$ buffer, pH 6.5). Kinetics at 340 nm for 5 min at room temperature using Varian spectrophotometer was obtained.

Furthermore, GSTP activities towards CDNB were assessed in the presence of various concentration of GSR4. The GSTP activities decreased when the concentration of GSR4 increased (Table 3). Thus, COH-SR4 was a product inhibitor of GSTP with an estimated $K_i$ of less than 5 µM.

TABLE 3

| GSTP activity towards CDNB in the presence of GSR4 | |
|---|---|
| [GSR4] (µM) | GSTP activity towards CDNB ($K_{cat}$ [s-1]) |
| 0 | 93977 |
| 5 | 36385 |
| 10 | 16115 |

Example 12

Effects of COH-SR4, COH-SR9 and COH-SR18 on Melanoma Cell Line B16F10 (FIG. 53)

Cells of highly aggressive mouse melanoma cell line B16F10 were incubated with various doses of COH-SR4, COH-SR9 and COH-SR18 (1, 3, 5 or 10 µM) for 48 hours. The cell viabilities were measured and summarized in FIG. 53A. COH-SR4 showed the best potency in killing B16F10 cells among the drugs tested.

HUVEC were treated with COH-SR4 at a concentration from 0.1~100 μM for 48 hours. COH-SR4 showed significant lower cytotoxicity to HUVEC cells compared to the melanoma cells. COH-SR4 showed almost no cytotoxicity to HUVEC cells at a concentration of up to 10 μM.

Data presented were representative of at least 4 replicates and the standard deviations were also presented.

Example 13

Effects of COH-SR4 on Mouse Melanoma Cell Line B16-F0 and Human Melanoma Cell Line Hs600T (FIGS. 54 and 55)

Cells of highly aggressive mouse melanoma cell line B16-F0 or human melanoma cell line Hs600T were incubated with various doses of COH-SR4 (1, 2.5, 5, 10, 25, 50, or 100 μM). The cell viabilities after treatment of 48 hours and 96 hours were measured and summarized in FIGS. 54A and 55A, respectively. The $IC_{50}$ of COH-SR4 in B16-F0 and Hs600T after treatment of 48 hours and 96 hours were measured respectively (FIGS. 54B and 55B). Data were presented as mean±Standard Deviation from two separate determinations with eight replicate each (n=16). The $IC_{50}$ of COH-SR4 in B16-F0 after treatment of 48 hours was about 14 μM; the $IC_{50}$ of COH-SR4 in Hs600T after treatment of 48 hours was about 10 μM; the $IC_{50}$ of COH—SR4 in B16-F0 after treatment of 96 hours was about 5 μM; and the $IC_{50}$ of COH-SR4 in Hs600T after treatment of 96 hours was about 6 μM. COH-SR4 showed cytotoxicities in both cell lines.

Example 14

Effects of COH-SR4 on Apoptosis in Melanoma Cells (FIG. 56)

B1-F0 mouse melanoma cells were grown on cover slips and treated with 10 μmol/L COH-SR4 for 24 hours. TUNEL assay was carried out using Promega Fluorescence Detection Kit. Apoptotic cells showed green fluorescence. The data showed that treatment of COH-SR4 increased apoptosis in melanoma cells (FIG. 56). The pictures shown in the top panels were obtained from one sample, and the pictures shown in the bottom panels were obtained from another sample (FIG. 56).

Example 15

Effects of COH-SR4 on Apoptosis in B16 Mouse Melanoma Tumor Section (FIGS. 57 and 58)

B16 melanoma bearing C57B mice tumor sections were treated without or with COH-SR4, and used for histopathologic analyses.

H&E stain, or hematoxylin and eosin stain, a general gross morphology stain were used. Hematoxylin had a deep blue-purple color and stained nucleic acids. Eosin was pink and stained proteins nonspecifically. In a typical tissue, nuclei were stained blue, whereas the cytoplasm and extracellular matrix had varying degrees of pink staining. The pink coloration in the control tumor cells indicated cell proliferation (FIG. 57)

IHC analyses for Ki-67 expression (marker of cellular proliferation), CD31 (angiogenesis marker), and pAMPK (cellular regulator of lipid and glucose metabolism) from tumors in mice of control and COH-SR4-treated groups were carried out. Statistical significance of difference was determined by two-tailed Student's t test. When COH-SR4-treated tumor sections were compared with the control, p<0.001. Immuno-reactivity was evident as a dark brown stain, whereas non-reactive areas displayed only the background color. Sections were counterstained with Hematoxylin (blue). Photomicrographs at 40× magnification were acquired using Olympus Provis AX70 microscope. Percent staining was determined by measuring positive immuno-reactivity per unit area. Arrows indicated the areas for positive staining for an antigen. The intensity of antigen staining was quantified by digital image analysis. Bars represented mean±S.E. (n=5); "*" means p<0.001 compared with control.

The results showed that treatment of COH-SR4 lowered cellular proliferation (decreased Ki67), lowered angiogenesis (decreased CD31) and increased cellular regulation of lipid and glucose metabolism (increased pAMPK) in melanoma tumors.

Western-blot analyses of signaling proteins in tumor tissue lysates in control and COH-SR4 treated groups were shown in FIG. 58. Crude fraction (about 50 μg) and WB with various antibodies were used. The densities of the COH-SR4 treated bands were divided by the corresponding bands in the control group, and summarized in Table 4 below.

TABLE 4

| | Ratio of proteins in COH-SR4 treated groups v. control groups | | | | | | | | |
|---|---|---|---|---|---|---|---|---|---|
| | pAkt | Akt | Vimentin | Fibronectin | Bim | Bcl2 | CDK4 | Cyclin B1 | pAMPK |
| COH-SR4 group/ Control Group | 0.32 | 0.84 | 0.39 | 0.22 | 5.8 | 0.39 | 0.29 | 0.32 | 3.1 |

Example 16

Effects of Oral Administration of COH-SR4 in In Vivo Syngeneic Mouse Model (FIGS. 59~61).

C57B mice for syngeneic model were obtained from Harlan, Indianapolis, Ind. All animal experiments were carried out in accordance with a protocol approved by the Institutional Animal Care and Use Committee (IACUC). Ten 10-weeks-old mice were divided into two groups of 5 animals (treated with corn oil (vehicle), and COH-SR4 4 mg/kg body weight). All 10 animals were injected with $1×10^6$ mouse melanoma cells (B16-F0) suspensions in 100 μL of PBS, subcutaneously into one flank of each mouse. At the same time, animals were randomized treatment groups as indicated in the figure. Treatment was started 10 days after the B16 melanoma cells implantation to see palpable tumor growth. Treatment consisted of 0.1 mg of COH-SR4/mice in 200 µL corn oil by oral gavage alternate day. Control groups were treated with 200 µL corn oil by oral gavage alternate day. Animals were examined daily for signs of tumor growth, and body weights were recorded. Tumors were measured in two dimensions using calipers. Photographs of animals were taken at day 1, day 10, day 14, day 18, and day 20 after subcutaneous injection, are shown for all groups. Photographs of tumors were also taken at day 20.

Mice treated with COH-SR4 showed similar weights compared to mice treated with corn oil (FIG. 59A). The tumor cross-section areas in the mice treated with COH-SR4 were significantly smaller than that of the mice treated with corn oil (FIG. 59B). Tumor weights in the mice treated with COH-SR4 were significantly smaller than that of the mice treated with corn oil at day 20 (FIG. 60), "*" means p<0.001 for COH-SR4 treated group when compared to the control group.

Photos of tumor taken during the treatment are shown in FIG. 61, "*" indicates COH-SR4 treatment started alternate day by oral gavage after 10 days of B16-F0 cells implantation. Treatment of COH-SR4 elongated the life of the B16-F0 melanoma mice. Mice treated with corn oil only died on day 20, while mice treated with COH-SR4 at a dosage of 4 mg/kg died on day 48. The tumor size at day 20 in the mice treated with corn oil only was more than twice of that in the mice treated with COH-SR4. Thus, COH-SR4 was effective in treating melanoma in vivo.

Example 17

Treatment of Anti-RLIP76 Polyclonal Antibodies Increased COH-SR4 Cytotoxicities in B16F10 Cells (FIG. 62)

Anti-RLIP76 IgG potentiated the cytotoxicities of COH-SR4 in vitro. B16F10 cells were treated with various fixed doses of anti-RLIP76 polyclonal antibodies for 24 hours followed by treatment of various doses of COH-SR4 and MTT cell proliferation assay was performed after 48 hours. The data plotted in FIG. 62 were representative of at least 4 replicates and the standard deviations were also presented. Anti-RLIP76 IgG showed a dose-related increase of COH-SR4 cytotoxicities in B16F10 cells. The higher concentration of the anti-RLIP76 IgG was used, the more cytotoxic COH-SR4 was to the cells treated. Thus, treatment of COH-SR4 in combination with anti-RLIP76 IgG could be an effective way to treat cancer, and could be more effective compared to treatment with COH-SR4 alone.

The references cited supra and the references listed below are herein incorporated by reference in their entireties:
1. Adler v. Zin Z., et al., regulation of JNK signaling by GSTP. EMBO J. 1999, 18:1321-1324.
2. Al-Hajj M, Wich M S., et al., 2003, PNAS, 100:3983-3498.
3. Ali-Osman F, Brunner J M, et al., Prognostic significance of Glutathione S-transferase P expression and subcellular localization in human gliomas. Clin. Cancer Res., 3:2253-2261, 1997.
4. Auld, C. A., Fernandes, K. M., and Morrison, M. A., J. Cell. Physiol. 211:101-111 (2007).
5. Badva, A., Dabbs, D. J. et al., Modem Pathology, 2011: 24: 157-167.
6. Barwixk M, Wiggins C, The current epidemiology of cutaneous malignant melanoma, Front. Biosci., 11:1244-1254, 2000.
7. Booch, A., Eroles, P. et al., 2010 Cancer Treat Rev. 36:206-215.
8. Boyle J. G., Logan, P J., et al 2011 Diabetologia 54: 1799-1809.
9. Bray, G. and Bellanger, T., Endocrine 29:109-117 (2006).
10. Bray, G. A. and Tartaglia L. A., Nature, 404:672-677 (2000).
11. Bruserud, O., Gjertsen, B. T., Huanga, T., The Oncologist 5:454-462 (2000).
12. Carra, A., De Pasquale, F. et al., 2006, Plant Cell Tissue Organ Culture, 87:41-48.
13. Chao, R W., Wang, X., et al., 2008, Stem Cells 2008, 26:364-371.
14. CHOU, TING-CHAO. Theoretical Basis, Experimental Design, and Computerized Simulation of Synergism and Antagonism in Drug Combination Studies PHARMACOLOGICAL REVIEWS Vol. 58, No. 3, 2006.
15. Cool, B., Tinkler, B., et al; 2005, Cell Metabolism 3:403-416.
16. Davies, G. F., Ross, A. R. et al., Cancer Letters Cancer Lett. 288:236-250 (2010).
17. de Ferranti, S, and Mozaffarian, D., Clinical Chemistry 54:945-955 (2008).
18. DeAngelis L M (2001). Brain tumors. N Engl J Med 344, 114-123.
19. Doyle, B. T., O'Neill, A. J., Fitzpatrick J. M., Wtason R. W. G., Apoptosis 9:345-352 (2004).
20. Fernandes, K. M., Auld, C. A., Hopkins, R. G., and Morrison, R. F., J. Cell. Biochem. 105:913-921.
21. Fischer H, Gottschlich R, Seelig A. Blood-brain barrier permeation molecular parameters governing passive diffusion J Membr Biol 165:201 211 1998.
22. Fogarly S, Hardie D G, 2010 Biochem, Biophys. Acta, 1804: 581-591.
23. Gaspar J. Kitange, et al. Induction of MGMT expression is associated with temozolomide resistance in glioblastoma xenografts. Neuro Oncol (June 2009) 11 (3): 281-291.
24. Grabble, A. D., Dolle, R. E., et al., J. Med. Chem. 39:3569-3584 (1996).
25. Green, C. J. Pederseu, M., et al; 2011, Diabetes 60:2810-2819.
26. Guihua Huanga, Na Zhanga, Xiuli Bia and Mingjin Doub. Solid lipid nanoparticles of temozolomide: Potential reduction of cardial and nephric toxicity. International Journal of Pharmaceutics. volume 355, Issues 1-2, 1 May 2008, Pages 314-320.
27. Gupta P B, Chaffer C L, Weinberg R A. NaT. Med. 15:1010-1012 (2009).
28. Gupta, P B., Onder, T T., Jiang, G., Tao, K., Kuperwasser, C., Weinberg, R A., 2009, Cell, 138: 645-659.
29. Hansen L A, Sigman C C, Andreola F, Ross S A, Kelloff G J, De Luca L M. Carcinogenesis 21:01271-1279 (2000).
30. Hardie D G, 2010, Gene and Development 25:1895-1908.
31. Hatzivassiiiou, G. T., Zhao, F. et al., Cancer Cell 8:311-321 (2005).
32. Hayes J D, and Pulford D J., The glutathione S-transferase superfamily; regulation of GST and the contribution of isoenzymes to cancer chemotherapeutics and drug resistance. Crit. Rev. biochem. Mol. Biol., 30:445-600, 1995.
33. Hayes J D, Flanagan J U, Jowsey I R, Glutathione transferase, Anu. Rev. Pharmacol. Toxicol., 2005, 45:51-88.
34. Heitz, D., Erxleben, et al., 2006, J Proteome Res. 5:2283-2293.

35. Hurt, H. M. and Farrar, W. L., Mol. Interv. 8:140-142 (2008).
36. "Inhibitors Reduce *Staphylococcus aureus* Hemolytic Activity and Protect Cultured Endothelial Cells from Lysis," ANTIMICROBIAL AGENTS AND CHEMOTHERAPY, August 2002, p. 2333-2336 Vol. 46, No. 8.
37. Jacoby W B, the glutathione S-transferase: a group of multi-functional detoxification proteins. Adv. enzymol. Mol. biol., 46: 383-414, 1978.
38. Kim J Y, Mercer S E, et al., the stress activated protein Kinase p38 alpha and JNK1 stabilize p21 (CIP) by phosphorylation. J. Bio. Chem., 277: 29792-22802, 2000.
39. Kim, S., Park, H., Lee, M., et al., Biochem. Biophys. Res. Comm. 327:108-113 (2008).
40. Kim, S. N., Choy, H. Y., Kim, Y. K., Arch. Pharm. Res. 32:535-541 (2009).
41. Laborde E, Glutathione transferases as mediators of signaling pathways involved in cell proliferation and cell death. Cell Death and differentiation 2010, 171373-1380.
42. Lapidot, T., Sirard, C., et al., 1994, Naturi. 367:645-648.
43. Lee G., Fryer D., et al, 2002, J. Brol. Chem., 277:25226-25232.
44. Leszczyniecka M, Roberts T, Dent P, Grant S, Fisher P B. Pharmacol Ther. 9:105-56 (2001).
45. Li Fang Yu, Bei-Ying Qiu, et al., 2010, Current topics in Medicine Chemistry 54:3101-3110.
46. Li, J. J., Wang. H. et al., Bioorganie & Medicinal Letters 17:3208-3211 (2007).
47. Linos E, Swetta, S., et al., increasing burden of melanoma in the United States. J. Invest. Derm., 8: 2009.
48. Liu, H., Patel, M R., et al., 2010, PNAS, 107: 18115-18126.
49. Lopez-bergami P, Huang c., et al., Rewired Erk-JNK signaling pathways in melanoma. Cancer Cell, 11; 447-460, 2007.
50. Lowe S W, Lin A W, Appoptosis in cancer. Carcinogenesis, 21: 485-493, 2000.
51. Lyon R P, Hill J J, atkins W M, Novel class of bivalent glutathione stransferase inhibitors. Biochemistry 2003, 42; 10418-10428.
52. Mannervik g, Castro V M., et al., Expression of class P1 glutathione transferase in human malignant melanoma cells. Carcinogenesis 1987, 8:1929-1932.
53. Mol Cancer Ther 2009; 8(12). December 2009.
54. Nowak, D, Stewart D, Koeffler H P Blood, 113:3655-3665 (2009).
55. Ofra Benny and Pouya Pakneshan. Novel technologies fantiangiogenic drug delivery in the brainCell Adh Migr. 2009 April-June; 3(2): 224-229.
56. Petrie, K., Zellent, A., Waxman, S., Current opinion in Hematology 16:84-91 (2009).
57. Pilch, P. F. and Bergenhem, N., Mol. Pharmacol. 70:779-785 (2006).
58. Pipeline insight: Cancer Overview—gastrointestinal, skin, sarcoma. Data monitor pharmaceutical report; 118-123, 2008.
59. Prat A., Perou, C. M., Molecular Oncology; 2001: (1): 5-23.
60. Proctor, R. A., et al., Two Diarylurea Electron Transport PSA—is expressed on the surface of NSCs: Marina Quartu, #1 Maria Pina Serra, #1 Marianna Boi, 1 Viviana Ibba, 1 Tiziana Melis, 1 and Marina Del Fiacco#1 BMC Neurosci. 2008; 9: 108.
61. Rahbar, S., Lalezari, I. U.S. Pat. No. 6,337,350.
62. Rahbar, S., Lalezari, I. U.S. Pat. No. 6,589,994.
63. Rahbar, S., Lalezari, I. U.S. Pat. No. 6,605,642.
64. Rahbar, S., Lalezari, I. U.S. Pat. No. 6,693,106.
65. Rahbar, S., Lalezari, I. U.S. Pat. No. 6,787,566.
66. Rahbar, S., Lalezari, I. U.S. Pat. No. 7,030,133.
67. Rahbar, S., Figarola, J., U.S. Pat. No. 7,320,988.
68. Rahbar, S., Figarola, J., U.S. Pat. No. 7,652,037.
69. Rathmell, J. C., Newgard, C. B., Science 324:1021-1022 (2009).
70. Ricci, A., Bertoletti, C., 2009, Plant Biology 14:262-272.
71. Ricci, A., Carra, A. et al., 2005 J Plant Growth Regul., 23:261-268.
72. Riester, D., Hildmann, C., Appl. Microbiol. Biotechnol. 75:499-514 (2007).
73. Roy, R., Willan, P., Clarke, R., Farnie, G., Breast Cancer Res. 18:12 Suppl 1:05 (2010).
74. Sell S, Crit. Rev Oncol Hematol 5: 1-28. (2004).
75. Shea T C, Kelley S L, Henner W D, Identification of an anionic form of glutathione transferase present in many human tumors and human tumors cell lines. Cancer Res., 1988, 48:527-533.
76. Steven R, et al. Pharmacokinetic assessment of novel anti-cancer drugs using spectral analysis and positron emission tomography: A feasibility study. Cancer Chemother Pharmacol. 42, 183, 1998.
77. Stupp et al., N Engl J Med 2007; 352:987-996.
78. Tew K D, Monks A, et al., Glutathione associated enzymes in the human cell line of the National Cancer Institute Drug screening Program. Mol. Pharmacol., 1996, 50:149-159.
79. Van Lenten, L. and G. Ashwell, 1 mM Nalo4 selectively oxidizes sialic acid. J. Biol. Chem. 246, 1889 (1971).
80. Wald, D. N., Verraaat, H. M. et al., Cancer Research 68:4369-4376 (2008).
81. Wang W, Guan K L. 2009, Acta Physiol (Oxf). 196:55-63.
82. Waxman D, Glutathione s-transferase: role in alkylating agent resistance and possible target for modulation chemotherapy—a review, Cancer res., 50: 6449-6454, 1990.
83. Wellen, E. K., Hatzivassiliou, G. et al., Science 324: 1076-108 (2009).
84. William M. Pardridge. The Blood-Brain Barrier: Bottleneck in Brain Drug Development. NeuroRx. 2005. 2(1): 3-14.
85. Yu L F, Qiu B Y, Nan F J, Li J. 2010, Curr Top Med. Chem. 10:397-410.
86. Yun H, Ha J. 2011, Expert Opin Ther Pat. 21: 983-1005.
87. Zhuang, Y., Miskimins, W. K., 2008, J. Molecular Signaling 3:18.

The invention claimed is:

1. A method of treating obesity in a subject comprising administering to the subject a pharmaceutical composition comprising a pharmaceutically acceptable carrier and a therapeutically effective amount of a first compound selected from the group consisting of COH-SR1, COH-SR2, COH-SR6, COH-SR7, COH-SR11, LR59:
and the pharmaceutically acceptable salts and stereoisomers thereof, including mixtures thereof in all ratios.

2. The method according to claim 1, wherein the first compound is selected from the group consisting of COH-SR1, COH-SR2, COH-SR7, LR59, and the pharmaceutically acceptable salts and stereoisomers thereof, including mixtures thereof in all ratios.

3. A method of treating a cancer selected from the group consisting of leukemia, acute myeloid leukemia (AML), monocytic leukemia, lung cancer, non-small cell lung cancer, colon cancer, CNS cancer, melanoma, ovarian cancer, renal cancer, brain cancer and breast cancer in a subject comprising administering to the subject a first pharmaceutical composition comprising a pharmaceutically acceptable carrier and a therapeutically effective amount of a first compound selected from the group consisting of COH-SR2, COH-SR6, COH-SR7, and the pharmaceutically acceptable salts and stereoisomers thereof, including mixtures thereof in all ratios.

4. The method according to claim 3, wherein the pharmaceutical composition further comprising a second therapeutic agent selected from the group consisting of TMZ, SN38, CPT-11, and 5-FU.

5. The method according to claim 3, further comprising administering a second pharmaceutical composition comprising a second therapeutic agent.

6. The method according to claim 5, wherein the second therapeutic agent selected from the group consisting of TMZ, SN38, CPT-11, 5-FU and anti-RLIP76 IgG (immunoglobulin).

* * * * *